US011963889B2

(12) United States Patent
Parr

(10) Patent No.: US 11,963,889 B2
(45) Date of Patent: *Apr. 23, 2024

(54) SYSTEM FOR DESIGNING AND FABRICATING A CUSTOMISED DEVICE

(71) Applicant: 3DMorphic Pty Ltd, Tamarama (AU)

(72) Inventor: William C. H. Parr, Tamarama (AU)

(73) Assignee: 3DMorphic Pty Ltd, Tamarama (AU)

(*) Notice: Subject to any disclaimer, the term of this patent is extended or adjusted under 35 U.S.C. 154(b) by 0 days.

This patent is subject to a terminal disclaimer.

(21) Appl. No.: 17/658,030

(22) Filed: Apr. 5, 2022

(65) Prior Publication Data

US 2022/0226130 A1 Jul. 21, 2022

Related U.S. Application Data

(63) Continuation of application No. 16/072,790, filed as application No. PCT/AU2017/050056 on Jan. 25, 2017, now Pat. No. 11,331,205.

(30) Foreign Application Priority Data

Jan. 25, 2016 (AU) ................................ 2016900216

(51) Int. Cl.
*A61F 2/50* (2006.01)
*A61F 2/30* (2006.01)
(Continued)

(52) U.S. Cl.
CPC ........ *A61F 2/5046* (2013.01); *A61F 2/30942* (2013.01); *B29C 64/393* (2017.08);
(Continued)

(58) Field of Classification Search
CPC ................ A61F 2/5046; A61F 2/30942; A61F 2002/30952; A61F 2002/505;
(Continued)

(56) References Cited

U.S. PATENT DOCUMENTS 6,608,631 B1 * 8/2003 Milliron ................. G06T 17/30
345/646
7,702,380 B1    4/2010 Dean
(Continued)

FOREIGN PATENT DOCUMENTS

JP       2012518519 A    8/2012
WO    WO 2004/110309 A2   12/2004
(Continued)

OTHER PUBLICATIONS

International Search Report and Written Opinion as received in PCT/AU2017/050056 dated Mar. 6, 2017.
(Continued)

*Primary Examiner* — Michael Le
(74) *Attorney, Agent, or Firm* — Keller Preece PLLC

(57) ABSTRACT

Disclosed herein are a method and system for producing a digital model of a customised device, comprising the steps of: importing a first digital file of a base part; importing a second digital file of a target shape; determining a warping interpolation function based on source point positions associated with the base part and target point positions associated with the target shape; and applying the warping interpolation function to the points of said base part to generate a model of said customised device.

19 Claims, 54 Drawing Sheets

(51) Int. Cl.
*B29C 64/393* (2017.01)
*B33Y 50/02* (2015.01)
*G06T 3/00* (2006.01)
*G06T 17/20* (2006.01)

(52) U.S. Cl.
CPC ............ *B33Y 50/02* (2014.12); *G06T 3/0093* (2013.01); *G06T 17/20* (2013.01); *A61F 2002/30952* (2013.01); *A61F 2002/505* (2013.01); *G06T 2210/41* (2013.01)

(58) Field of Classification Search
CPC .... A61F 2002/30943; A61F 2002/5049; A61F 5/01; A61F 5/0118; A61F 5/10; B29C 64/393; B33Y 50/02; G06T 3/0093; G06T 17/20; G06T 2210/41; G06T 19/20; G06T 2219/2021; A61B 17/7059; A61B 2017/568; A61B 17/8061; A61B 2034/102; A61B 34/10; Y02P 90/02

See application file for complete search history.

(56) References Cited

U.S. PATENT DOCUMENTS

| | | | | |
|---|---|---|---|---|
| 10,052,206 | B2* | 8/2018 | Mahfouz | ................ A61B 34/10 |
| 2006/0094951 | A1* | 5/2006 | Dean | ........................ G06T 17/10 |
| | | | | 600/407 |
| 2010/0292963 | A1* | 11/2010 | Schroeder | ................ A61F 2/30 |
| | | | | 703/1 |
| 2011/0282473 | A1 | 11/2011 | Pavlovskaia et al. | |
| 2012/0230566 | A1* | 9/2012 | Dean | ........................ G06T 15/00 |
| | | | | 382/128 |
| 2012/0290272 | A1* | 11/2012 | Bryan | ................ A61B 17/1684 |
| | | | | 703/1 |
| 2015/0039089 | A1* | 2/2015 | Balasubramanian | ........................ |
| | | | | A61F 2/4425 |
| | | | | 623/17.15 |
| 2016/0030067 | A1* | 2/2016 | Frey | ........................ A61B 50/33 |
| | | | | 606/86 A |
| 2016/0074048 | A1* | 3/2016 | Pavlovskaia | ............ A61B 6/032 |
| | | | | 606/88 |
| 2017/0000614 | A1* | 1/2017 | Mahfouz | ............. A61F 2/30942 |

FOREIGN PATENT DOCUMENTS

| | | | | |
|---|---|---|---|---|
| WO | WO-2004110309 | A2* | 12/2004 | ......... A61F 2/30942 |
| WO | WO 2010/099359 | A1 | 9/2010 | |
| WO | WO-2010099359 | A1* | 9/2010 | ............. A61B 17/14 |
| WO | WO 2015/057898 | A1 | 4/2015 | |

OTHER PUBLICATIONS

International Preliminary Report on Patentability as received in PCT/AU2017/050056 dated May 8, 2018.
Office Action as received in Japanese application 2018-557165 dated Mar. 16, 2021.
U.S. Appl. No. 16/072,790, May 14, 2021, Office Action.
U.S. Appl. No. 16/072,790, Jan. 12, 2022, Notice of Allowance.

* cited by examiner

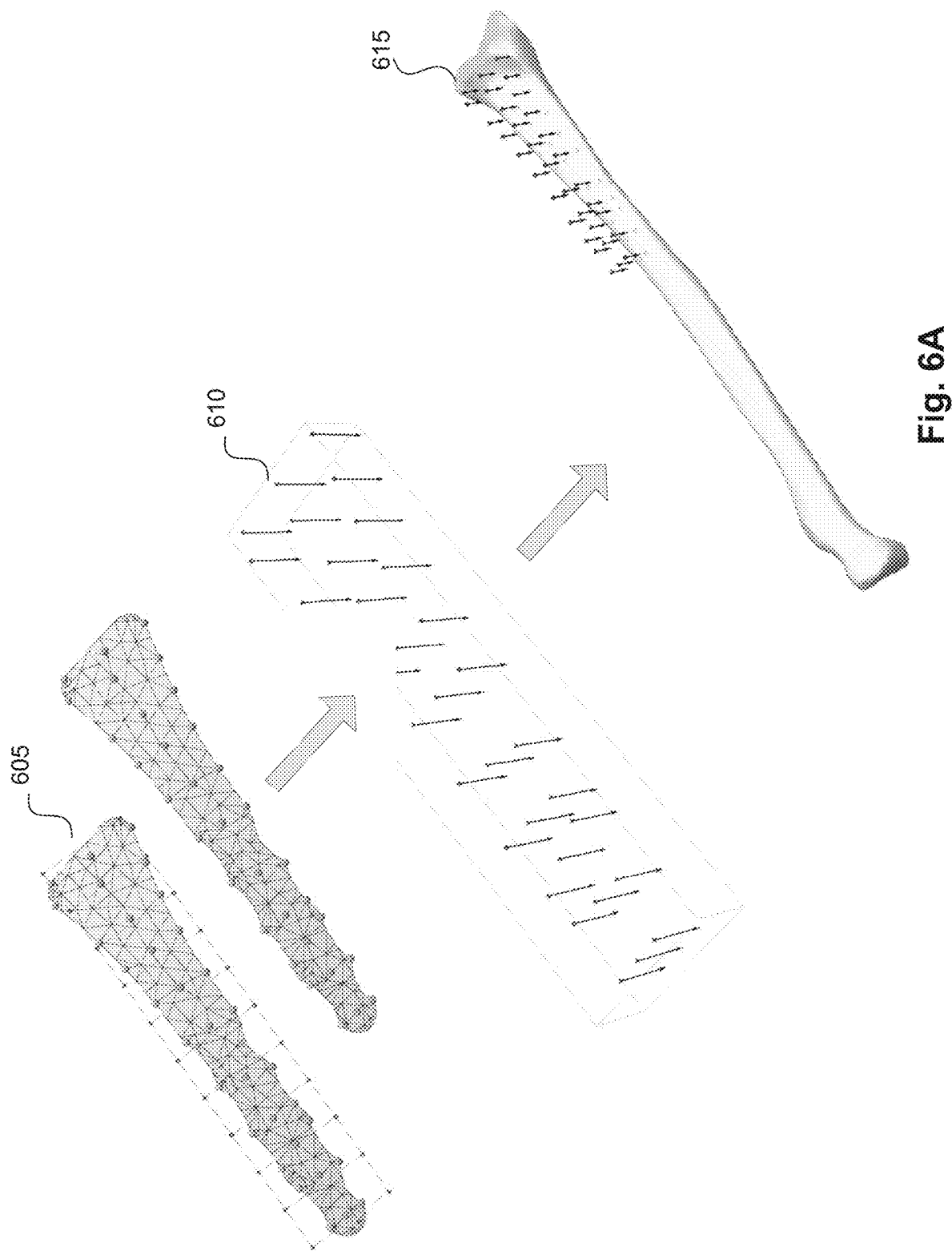

- User interaction: are the target shape and device positioned as you want them? If not press here to adjust them manually (rotation, translation, scale [with a warning] options)
  - NB: please ensure that the device is the correct way round and that the surface you want to face away from the target shape is facing away

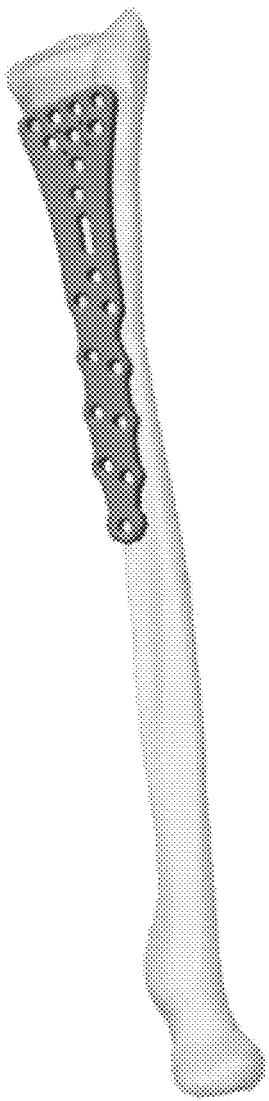

- Are you now happy to proceed?
  - you can come back if you realise something was not how you wanted it...

Fig. 14F

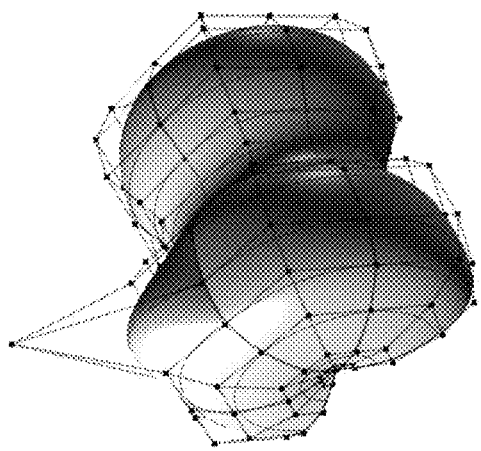 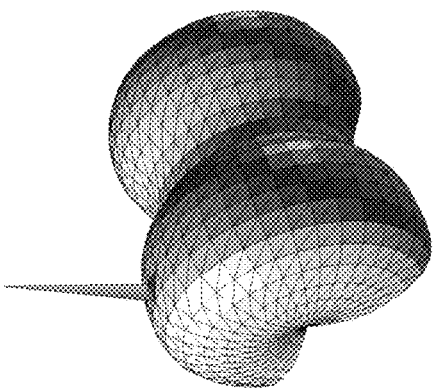
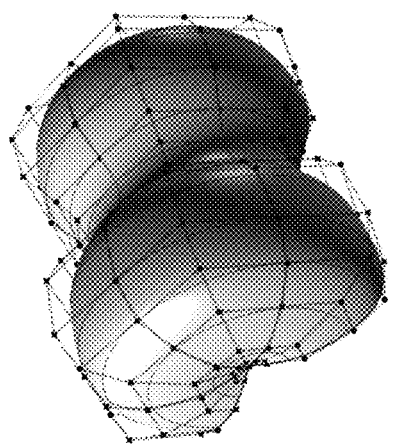 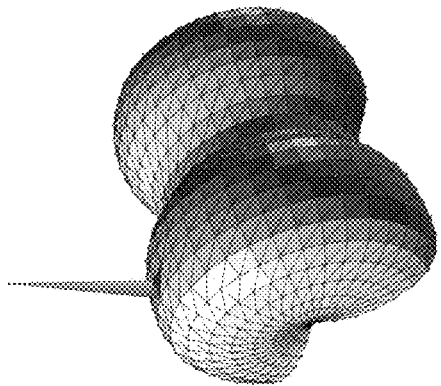
Fig. 16B  Fig. 16C
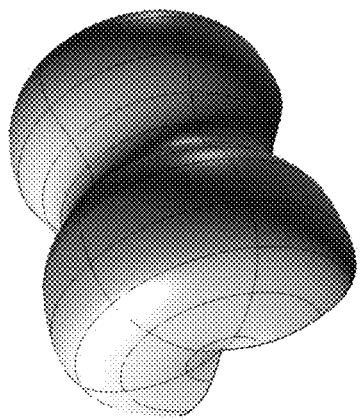 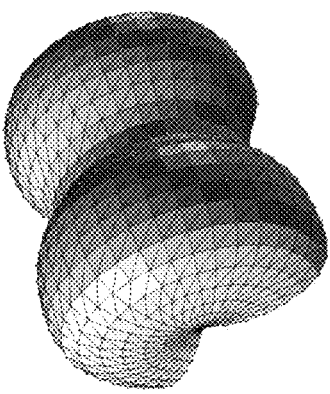
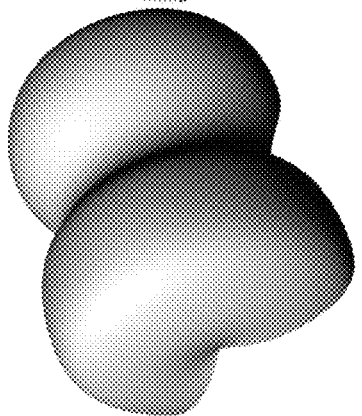 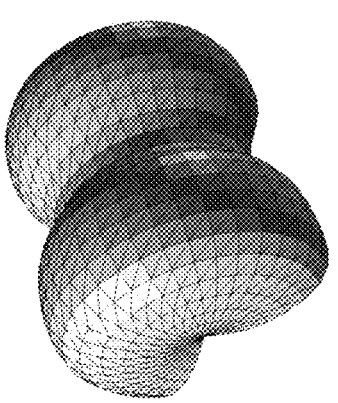

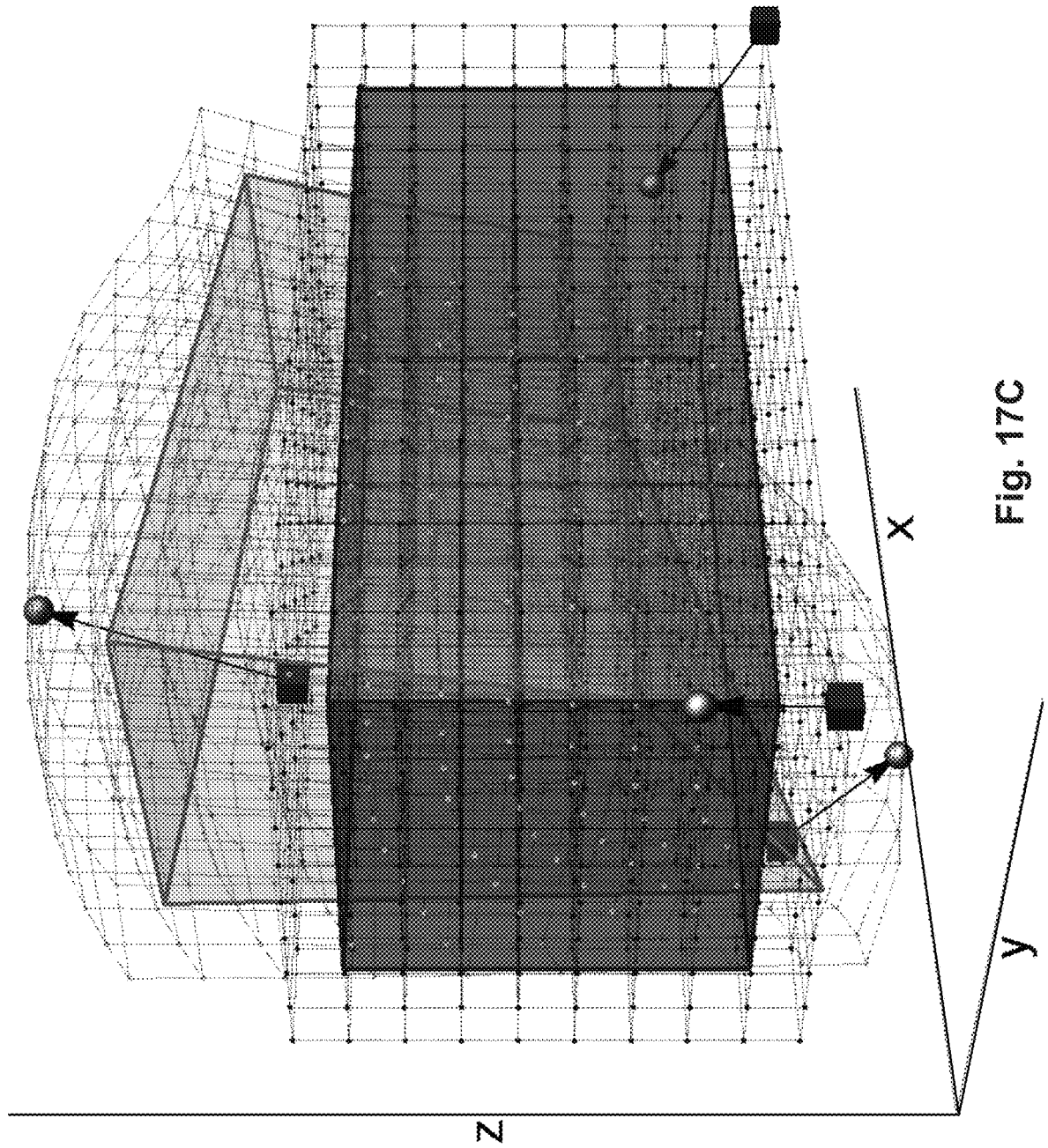

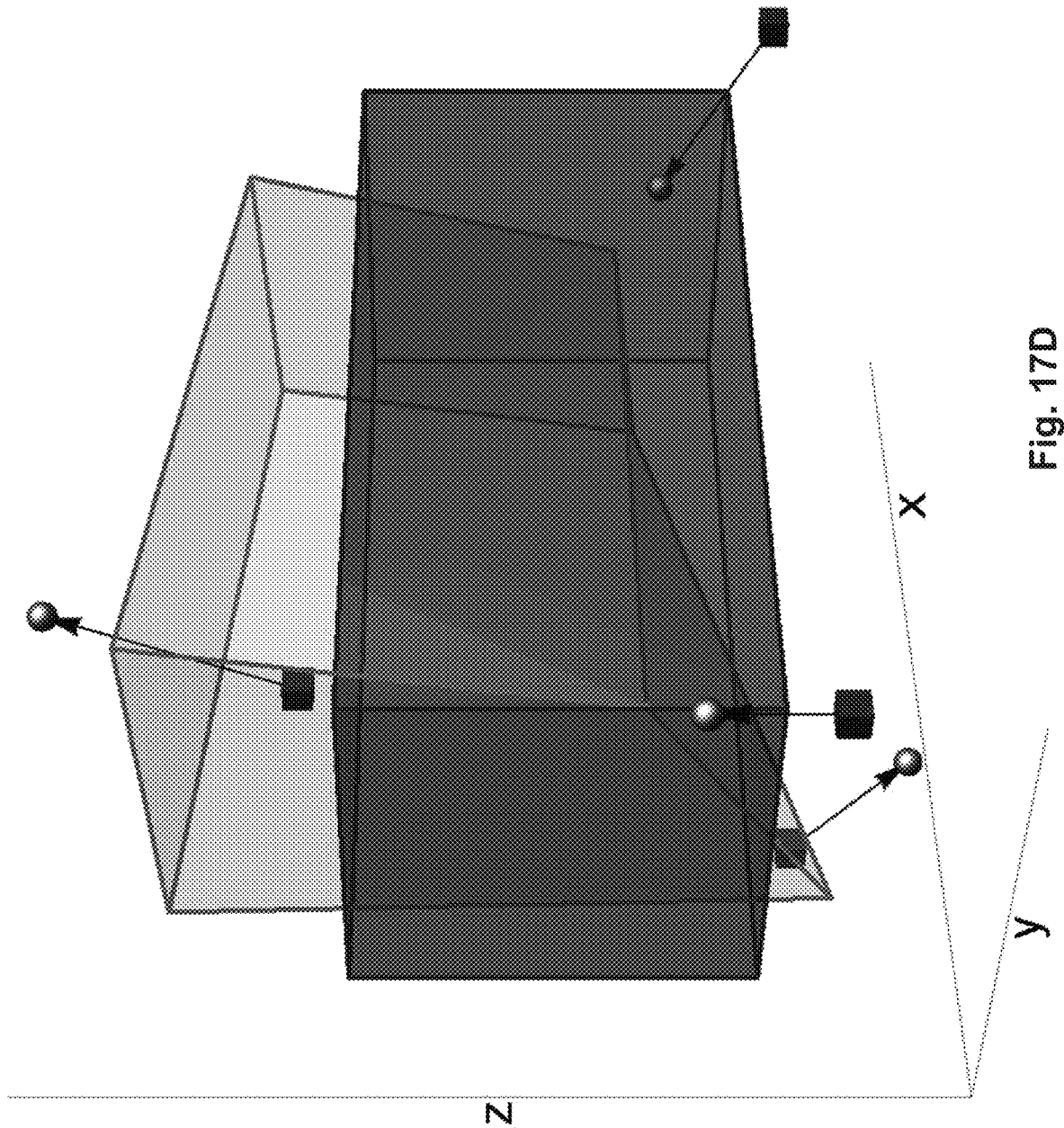

SYSTEM FOR DESIGNING AND FABRICATING A CUSTOMISED DEVICE

CROSS-REFERENCE TO RELATED APPLICATIONS

This application is a continuation of U.S. patent application Ser. No. 16/072,790, filed on Jul. 25, 2018, which is a national phase entry under 35 U.S.C. § 371 of International Application No. PCT/US2017/050056, filed 25 Jan. 2017, which claims the benefit of Australian Provisional Patent Application No. 2016900216 titled "Method and system for designing and fabricating a customised device" and filed on 25 Jan. 2016 in the name of 3DMorphic Pty Ltd. The entire contents of each of the foregoing patent applications are hereby incorporated by reference.

BACKGROUND OF THE INVENTION

1. Field of the Invention

The present disclosure relates to the technical field of Computer Aided Design and Computer Aided Manufacture (CAD/CAM). More particularly, the present disclosure relates to the design and fabrication of customised devices using computer aided manufacturing techniques.

2. Background and Relevant Art

Additive Manufacturing, which is also referred to as three-dimensional (3D) printing and/or rapid prototyping, refers to a process by which a digital file representing a 3D model of an object is used to control the deposition of material in layers to build up a physical instance of the object. Additive Manufacturing is now an established manufacturing process that, in recent years, has received increasing use in medicine for the production of accurate anatomical models for educational, research and surgical training purposes. As 3D printer resolutions have increased, so has the accuracy of manufactured parts, such that the manufactured parts are suitable for use in medicine.

As well as improvements in the accuracy of 3D printing, the range of materials in which 3D printers can manufacture has also increased. Such materials include a range of plastics and metals. Suitable plastics include, for example, acrylonitrile butadiene styrene (ABS), polylactic acid (PLA), soft polylactic acid (SOFT PLA), polyvinyl alcohol (PVA), and polycarbonate (PC). Suitable metals include, for example, steel, stainless steel, titanium, gold, and silver. More recently, the development of biocompatible polymers and biocompatible metal alloys, such as titanium Ti6Al4V-ELI (extra low interstitial) and cobalt chrome, have enabled additive manufacturing to be used for medical applications.

Medical doctors, for example orthopaedic surgeons, use a range of medical devices during the treatment of patients. Such medical devices include surgical instrumentation such as jigs, cutting and drilling guides, as well as implantable devices such as plates, cups and rods used during medical procedures. Further, external devices such as splints, casts, and the like are used to immobilise joints and assist with setting fractured bones. Such medical devices are typically available in a limited range of sizes and the doctor chooses the size that best matches the anatomy of the patient and the problem to be addressed.

Surgical plates used in orthopaedic procedures are typically relatively thin sheets of metal (often titanium or stainless steel) that are designed to be affixed to one or more bones. While such plates are available in a range of shapes and sizes, it is common for surgeons to need to alter the plate to match the particular anatomy of the patient. Such altering of the plate commonly involves the surgeon bending, twisting, hitting, deforming, or otherwise adjusting one or more portions of the plate during the surgical procedure. These alterations are typically quite crude and several iterations may be required in order to alter the plate to fit the patient to the satisfaction of the surgeon. As such alterations may occur during surgical procedures, the length of the surgery is prolonged while the plate is adjusted, leading to longer time under anaesthetic, increased risk of infection, and longer recovery times. The plates are also at increased risk of corrosion and stress fatigue/failure at the point of the bend.

An alternative to altering a physical medical device is to produce a customised medical device. Research has shown that customised planning, guides and implants result in better clinical outcomes for patients. While it is becoming accepted by the medical field that a customised approach does result in better patient outcomes, the technical skill, training and non-automation of current approaches to the design of custom guides and devices means that currently customised approaches are costly and slow. Therefore, the patient specific approaches are mostly used in relatively rare and/or difficult cases in which generic medical devices are not suitable.

Thus, a need exists to provide a method and system for customising medical devices.

SUMMARY

The present disclosure relates to a method and system for designing and fabricating customised objects using computer aided manufacturing methods, such as Additive Manufacturing, controlled robotic bending, and machine milling.

In a first aspect, the present disclosure provides a method for modifying a first digital model of a base generic device, said first digital model being a triangulated vertex boundary representation suitable for 3D printing, the method comprising the steps of:
  importing a second digital model of a target shape;
  modifying said first digital model to create a third digital model of a customised device based on said target shape, said modifying including:
    determining a warping interpolation function based on relative positions of a set of source points associated with the first digital model of the base generic part and relative positions of the same points projected to the target shape; and
    applying the warping interpolation function to all vertices of said base generic part to generate said third digital model of said customised device, wherein said third digital model of said customised device is adapted to fit said target shape.

In a second aspect, the present disclosure provides a method for modifying a digital model of a generic device, comprising the steps of:
  importing a first digital file of a base generic part;
  importing a second digital file of a target shape;
  modifying said first digital file to create a digital model of a customised device based on said target shape, said modifying including:
    determining a warping interpolation function based on a projection between said base generic part and said target shape, said projection determining relative positions of a set of points associated with the base generic part and relative positions of the same points associated with the target shape, the set of points associated with the base generic part having corresponding source point positions and the same points associated with the target shape having corresponding target point positions; and applying the warping interpolation function to all of the points of said base generic part to generate said digital model of said customised device, wherein said digital model of said customised device is adapted to fit said target shape.

In a third aspect, the present disclosure provides a method of producing a customised medical device for a patient, comprising the steps of:

importing a first digital file of a base generic part, said first digital file being a triangulated vertex boundary representation suitable for 3D printing;

importing a set of patient parameters relating to the patient;

warping all vertices of said base generic part, based on said patient parameters, to generate a digital model of a customised medical device;

exporting said digital model of said customised device to a computer aided manufacturing (CAM) device; and manufacturing said customised device, by said CAM device.

In a fourth aspect, the present disclosure provides a system for modifying a digital model of a generic device to produce a digital model of a customised device, said system comprising:

a processor; and a memory for storing a computer program for execution on said processor, said computer program including instructions for:

importing a first digital file of a base generic part;

importing a second digital file of a target shape;

modifying said first digital file to create a digital model of a customised device based on said target shape, said modifying including:

determining a warping interpolation function based on a projection between said base generic part and said target shape, said projection determining relative positions of a set of points associated with the base generic part and relative positions of the same points associated with the target shape, the set of points associated with the base generic part having corresponding source point positions and the same points projected to the target shape having corresponding target point positions; and applying the warping interpolation function to said points of said base generic part to generate said digital model of said customised device, wherein said digital model of said customised device is adapted to fit said target shape.

In a fifth aspect, the present disclosure provides a system for modifying a generic medical device to produce a customised medical device for a patient, said system comprising:

a computer aided manufacturing (CAM) device;

a processor; and a memory for storing a computer program for execution on said processor, said computer program including instructions for:

importing a first digital file of a base generic part, said first digital file being a triangulated vertex boundary representation suitable for 3D printing;

importing a set of patient parameters relating to the patient;

warping all vertices of said base generic part, based on said patient parameters, to generate a digital model of a customised medical device;

exporting said digital model of said customised device to said CAM device;

wherein said CAM device is adapted to manufacture said customised device, based on said exported digital model.

According to another aspect, the present disclosure provides an apparatus for implementing any one of the aforementioned methods.

According to another aspect, the present disclosure provides a computer program product including a computer readable medium having recorded thereon a computer program for implementing any one of the methods described above.

Other aspects of the present disclosure are also provided.

BRIEF DESCRIPTION OF THE DRAWINGS

One or more embodiments of the present disclosure will now be described by way of specific example(s) with reference to the accompanying drawings, in which:

FIGS. 6A to 6C illustrate warping of a model of a generic surgical plate;

FIGS. 14A to 14H show screenshots from a graphical user interface for receiving user input to customise a base model;

FIGS. 16A to 16E illustrate the differences in Computer Aided Design (CAD) boundary representations of surfaces between Parametric surfaces (for example a Non-Uniform Rational B-Spline surface as shown here) and tessellated surfaces (for example a triangulated point surface as shown here), demonstrated using a shape similar to the femoral condyle part of a total knee replacement (TKA) device;

FIGS. 17A to 17H illustrate the warping of 3D space and the results of inserting different base part shapes into this space, as well as the effects of inserting these base parts into different areas of the warped space.

DETAILED DESCRIPTION

Figure 1:
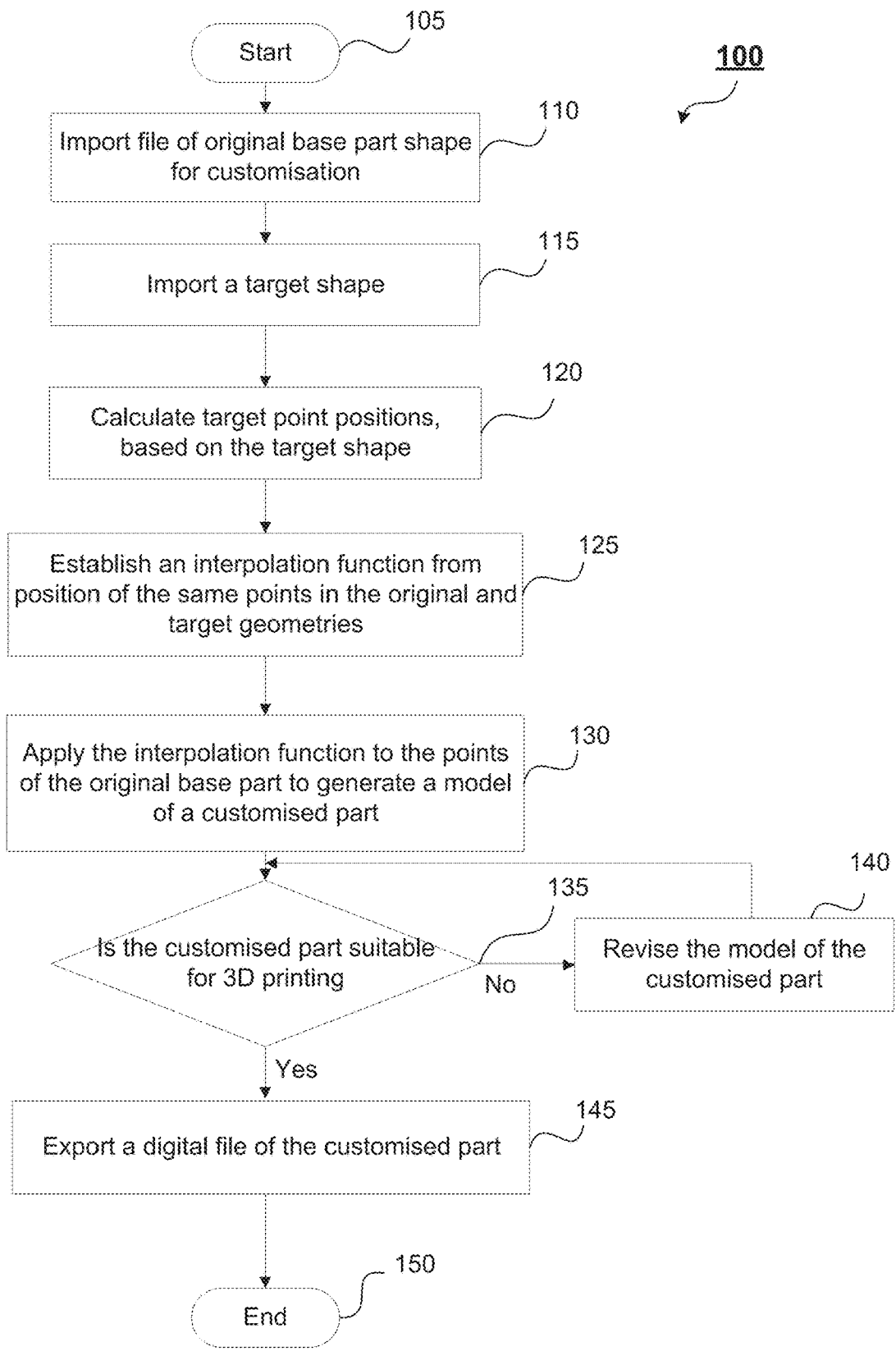
FIG. 1 is a flow diagram of a method for customising a digital model of a base part in accordance with the present disclosure.

Method steps or features in the accompanying drawings that have the same reference numerals are to be considered to have the same function(s) or operation(s), unless the contrary intention is expressed or implied.

The present disclosure provides a computer aided design (CAD) method and system for customising a shape of a designed device, based on a digital model of the designed device. A digital model of a designed device may be, for example, a digital file representing a 3D model of the designed device. The method warps, or distorts the shape of, the digital model of the designed device, based on a set of input parameters, to produce a digital file for a customised device. The set of input parameters may include, for example, but are not limited to, one or more dimensions, scaling factors, and points or dimensions of a space within which the customised device must fit. The digital file may then be used as an input to a computer aided manufacturing device to fabricate the customised device. Such computer aided manufacturing (CAM) devices may include, for example, 3D printers and computer numerical control (CNC) machines, including, mills, lathes, bending, hole-punching, routing, sawing, hydraulic presses, and the like. The method thus enables customised devices to be readily manufactured from one or more base models.

The method of the present disclosure modifies a base model using warping/customisation algorithms to produce a customised model. The method minimises the potential for inter and intra user differences in warping results by using, where possible, predefined source points and projecting these in an automated way to create target points to guide the warping of the device. In an alternative implementation, target points from a target shape are projected onto a source device to determine source points, with the projection from the target points to the source points determining the warping.

During the customisation process, the method described here:

1) maintains design features of a base model;
2) maintains critical dimensions (e.g., thickness for plates);
3) standardises the results by having automated systems (stored source point files with the generic/base device files), thereby taking out or lessening the potential of user influence/error; and
4) intentionally produces output files optimised specifically for the new enabling technology of additive manufacturing (3D printing) and CNC machining.

Thus, the method of the present disclosure enables custom designed devices to be produced in an efficient, controllable (in terms of design control), standardised and cost-effective way that current bottom-up customised device design methods cannot.

Throughout this specification, the method will be described in relation to medical devices, such as splints, plates, rods, cups, prostheses, implants, cages, and the like. However, such descriptions are illustrative and not restrictive. It will be readily understood by a person skilled in the art that the method of the present disclosure may be used to customise a digital model of any designed device and may be readily applied to any designed device, including building components, mechanical parts, and the like. For example, in building applications, individual components can be customised for a particular site.

In relation to medical devices, the method and system of the present disclosure enable the production of a device that is customised for a particular patient. Such customised devices are particularly useful in orthopaedic surgeries and may also be used for external splints, braces, orthotics, and the like.

In orthopaedic surgeries, such as attaching a plate to a bone, there is a need for the best fit possible between the device and bone. A well fitted, customised, plate can aid a surgeon during the procedure by guiding the two bone fragments (resulting from a planned osteotomy, or a trauma fracture) into the desired/correct alignment. A good fit also reduces lever arms, for example in a plate that is offset from the bone surface. Increased lever arms may result in increased stress being transmitted to/from device/bone, which increases the likelihood of failure of one or the other. In some applications, good fit of the device to the patient anatomy can reduce off axis moments, which reduces the chances of device failure and stress hotspots in unexpected/desired areas of the contacting bone. Good fit also reduces the occurrence of impingement of device/device-anatomy, as can occur in shoulder and hip arthroplasty (joint resurfacing or replacement). Impingement can also occur at the anterior distal bone of the femur in an intermedullary (IM) long nail, which can lead to patient pain or the distal portion of the IM nail breaking through the bone (particularly in older osteoporotic patients). Thus, customising devices to provide a better fit at the device-bone interface results in better patient outcomes.

Currently, custom devices are generally designed using a 'bottom' up approach, in which the surface of the patient's (3D reconstructed) anatomy is offset outwards from the bone surface. The offset distance is that of the desired device thickness (+/−manufacturing/modelling tolerances). This forms the basis for the device, with other features, such as screw holes, edge filleting, and the like having to be added subsequently.

Where generic devices, for example instrumentation such as cutting or drilling guides, are customised, currently the methods typically involve a Boolean subtraction of the bone/patient anatomy from a contacting surface of the generic device. Boolean subtraction of the bone anatomy from the contacting surface of the device in this way effectively leaves an imprint, or negative, of the bone shape in the contacting surface of the device. This method is suitable for some applications, for example designing patient anatomy fitting cutting or drilling guides, where the thickness of the device is inconsequential. However, because patient anatomy, and particularly pathological anatomy, is variable, the thickness of a device customised to fit a patient's specific anatomy in this way will be variable throughout the device, variable between the same device customised for different patient anatomies and, essentially, uncontrolled. For devices that must withstand loading, such uncontrolled variation in device thickness leads to changes in the load magnitudes that the device can withstand.

In one arrangement, the method and system of the present disclosure customise devices that already exist in the itinerary of medical device companies. These devices, as well as existing physical objects, are associated with a number of computer stored design files. These include the design master file, from which the device can be made. Such devices are typically associated with a design history file, which catalogues the development of all aspects of the device design, giving reasons for the inclusion of specific design features and detailing the functions of those features within the device as a whole. In other words, the design master file utilises the understanding of device geometry through purposeful design, testing, and re-design that is present in the design history of the device.

Additive manufacturing (3D printing) is currently not cost effective for mass production, but can create a one-off device for less cost than using a traditional production line process to produce the same one-off device. Although the manufacture of one device design can be achieved as easily as another device design through the use of additive manufacturing technology, the time, cost and labour is now transferred 'up-stream' to the design stage. In this scenario, the burden is on the design of the custom device, rather than the manufacture. The method of the present disclosure provides a way by which to (at least semi, if not fully) automate and standardise a design process that enables customised devices to be efficiently produced via additive (3D printing) or other computer aided manufacturing technologies (e.g., CNC machining, automated presses, and the like). The method is adapted to use existing design master files, as much prior design, research, testing and redesign has gone into the geometry of these design master files.

In accordance with the present disclosure, a method is defined for customising a shape of a designed device. In a biomedical setting, the designed device may be, for example, but is not limited to, a plate, cup with flanges, inter-body cage (or spacer), inter medullary nail, or total joint replacement. The method warps the geometry of the device, or aspects of the geometry, so that the customised device is patient specific. The method allows for maintenance of true geometric parts of the design, for example hemi-spherical cup geometry, locking screw threads, planar slits, or cylindrical drill guide holes (in the case of cutting guide design), as well as controlling other aspects of the geometry of a device (such as plate thickness), to ensure design parameters are maintained in the customised devices.

Further, the method controls the number of points, as well as the connectivity of these points, in the 3D model (which is a surface/boundary representation) of the device. In one arrangement, the boundary representation of the device is represented using tessellated (usually triangulated) polygons, but other representations, such as Non-Uniform Rational B-Spline (NURBS) parametric surfaces, as well as geometric shapes (sphere, cuboid, ellipsoid, torus, etc.), may equally be practised.

In addition, the method may be implemented as an automated or semi-automated process, resulting in a reduced time taken to produce a customised device, increased standardisation of customised device results, as well as reducing the requisite operator skill level and training to perform the customisation. Consequently, the method can be applied to a wide range of applications to produce customised devices wherever suitable additive or other computer aided manufacturing methods are available.

In some cases, a customised device may be created to fit an individual's body. Such customised devices may include, for example, splints, braces, supports, clothing, helmets, and shoes. In other cases, a customised device may be created to fit within a particular space or set of dimensions, such as mechanical parts like those used in motor racing or the aeronautical industry. In other cases, such as with customised plates used in osteotomy surgeries in conjunction with surgical planning and customised cutting guides, a patient specific plate may be customised to guide bone fragments into a desired post-operative alignment relative to one another.

In one application, the model is a medical device and the method customises an existing base model of the medical device to fit a specific patient. In such an application, the method customises the existing base model to fit the specific patient by using a 3D surface model of the bone to which the device is to be attached. The 3D model may be selected from a set of bone models, generated from serial Digital Imaging and Communications in Medicine (DICOM) data from a non-invasive CT or MRI scan, in conjunction with statistical normal bone models, and/or derived from an anatomical database, in order to plan surgical saw cut and drill-hole angles and subsequently customise pre-existing guide and device geometries. The resulting patient specific customised surgical guides and devices are optimised for fabrication using additive manufacturing (3D printing) methods.

FIG. 1 is a flow diagram of a method 100 for customising a digital model of a base part in accordance with the present disclosure. The method 100 begins at a Start step 105 and proceeds to step 110, which imports a file of an original base part shape for customisation. This file may be, for example, a triangulated point file in any one of the .stl, .ply, .obj, or .wrl formats, or other appropriate file format including geometry files such as .step and .igs files. The original base part shape for customisation may be any object. In one example, the original base part shape is an ankle brace or an orthopaedic surgical plate.

Control passes from step 110 to step 115, which imports a target shape. The imported target shape may be a triangulated point file of a target shape/anatomical morphology. In the example in which the base part shape is an ankle brace, the target shape may be a surface scan of a patient's foot and ankle. The surface scan may be obtained, for example, using surface laser or structured light scans. Alternatively, the target morphology may be chosen from an anatomical database, based on characteristics of the patient (e.g., age and height). In the example in which the base part shape is an orthopaedic plate, the triangulated point file of the target morphology may be derived from a CT scan or MRI data relating to a surface morphology of a patient's bone.

In another example, the triangulated point file of the target morphology may be a planned post-operative bone shape, such as may be extracted from a database of bone shapes. In such an example, a stored database of statistical bone shapes may be used and, from this, a target bone shape is selected or generated that provides a best match to the normal region of anatomy of the patient and as a guide for the correction of the non-normal/pathological region of the anatomy. Alternatively, the planned post-operative bone morphology may be derived from a scan of a "good" anatomical feature of the patient, such as the opposite foot and ankle to those which are damaged.

In an alternative arrangement, the target shape is a set of one or more parameters, such as linear dimensions, scaling factors, or a combination thereof. In the example in which the generic part shape is an ankle brace, the target shape may be a set of linear measurements taken from the target shape, such as the length, width, and height of the foot and ankle of the patient.

Figure 2A:
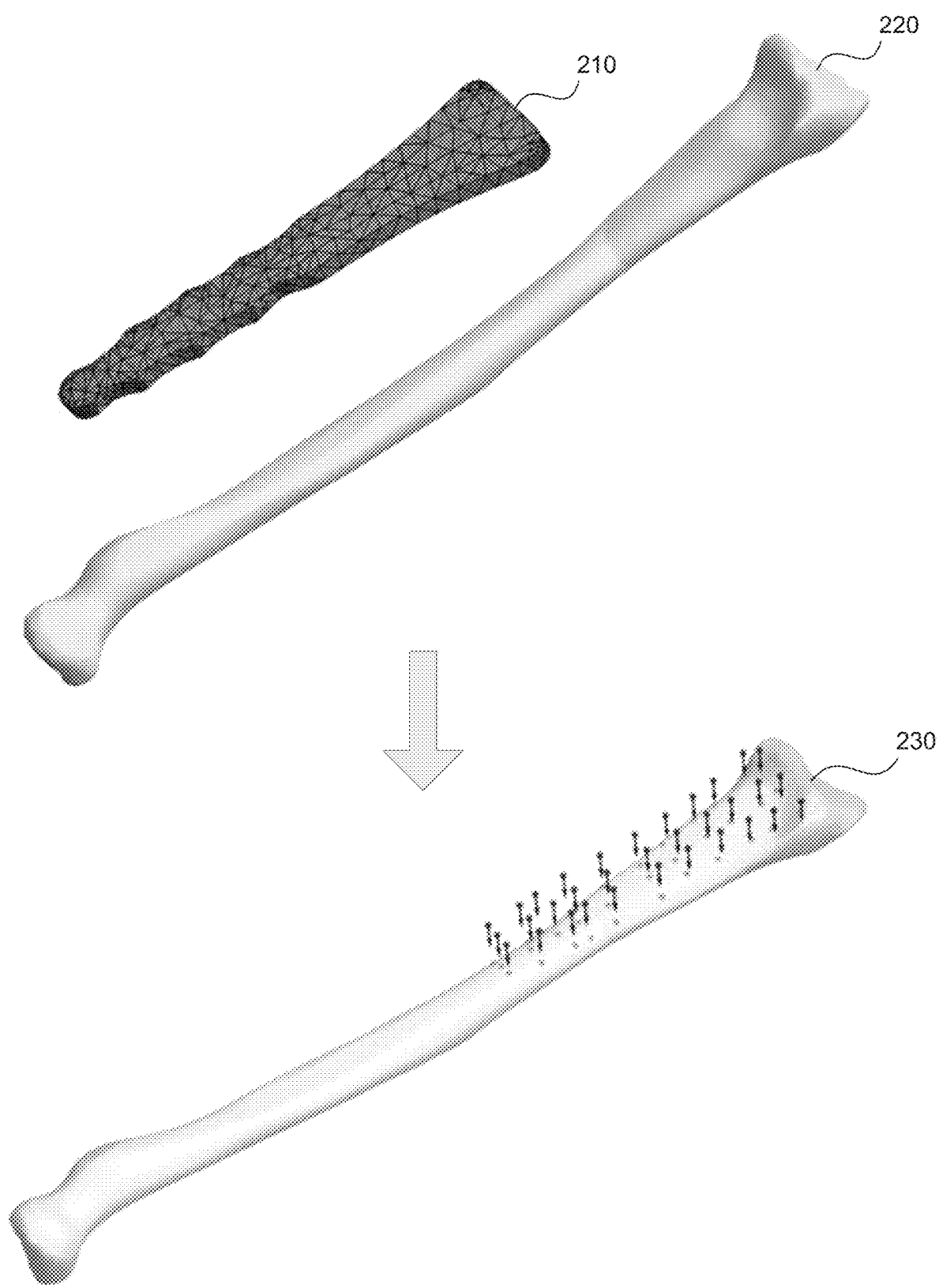
FIGS. 2A and 2B are schematic representations illustrating customisation of a digital model of a mock surgical plate.
Figure 2B:
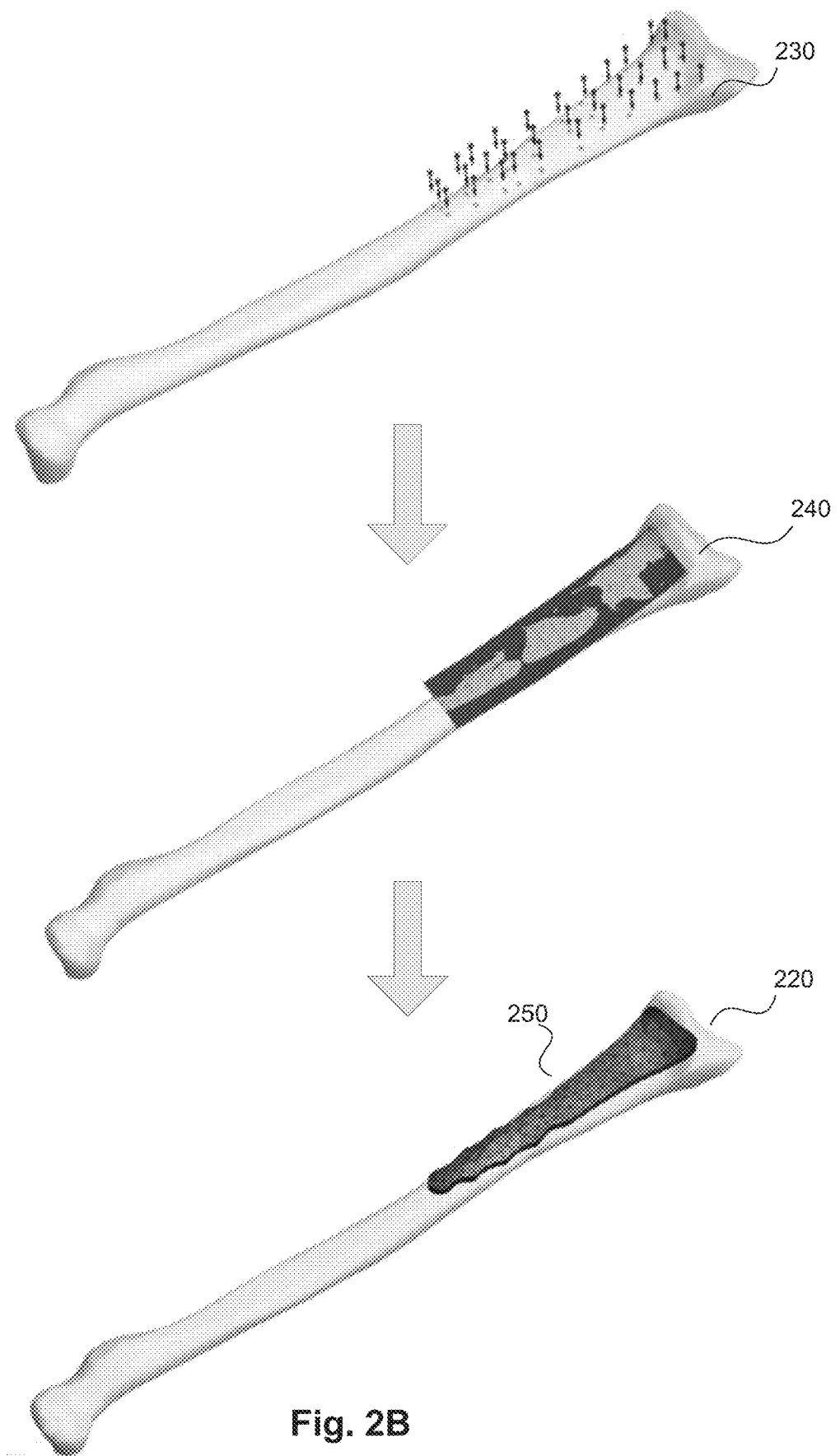

FIG. 2A shows a graphic representation of a triangulated file of an original base part shape 210, such as may be imported in step 110 of FIG. 1, alongside a target shape 220. In the example of FIGS. 2A and 2B, the base part shape is an orthopaedic plate and the target shape is a bone of a patient.

Returning to FIG. 1, control passes from step 115 to step 120, which calculates target point positions. Step 125 establishes a warping, or shape distorting, interpolation function based on positions of the same points in the original (source) point configuration and the target point configuration. Calculation of the target points is illustrated in FIG. 2A as a set of points 230, with the warping interpolation function being illustrated as a mapping 240 in FIG. 2B. Returning to FIG. 1, control then passes to step 130, which applies the warping interpolation function to the points of the original base part geometry to generate a model of a customised part.

Control passes from step 130 to decision step 135, which determines whether the model of the customised part is suitable for printing. If the model is not suitable for printing, No, control passes to step 140, which revises the model of the customised part. Such revisions may include, for example, tweaks or adjustments to the geometry of the customised part, adding colour or texture to a surface of the customised part, and the like, as well as checking that the triangulation of the part is suitable for entry into additive manufacturing or other computer-controlled manufacturing software (e.g., there are no floating shells, intersecting triangles, or holes in the surface). Control returns from step 140 to step 135. If at step 135 the model of the customised part is determined to be suitable for printing, Yes, control passes to step 145, which exports a digital file of the customised part. The digital file may then be uploaded to a suitable 3D printer or other CAM device (e.g., a 3D printer, robotic bending machine, hydraulic press, or the like) to fabricate an instance of the customised part. Control passes from step 145 to an End step 150 and the method 100 terminates.

FIG. 2B shows a customised part 250 that has been modified to fit the bone 220. In this particular example, the base model of a generic surgical plate has been warped based on the parameters of the target shape (i.e., the bone of the patient), so that a surgical plate of the appropriate dimensions can be securely fastened to the bone in the correct orientation and guide the distal region of the bone (post osteotomy) into the correct (planned) position.

Figure 3:
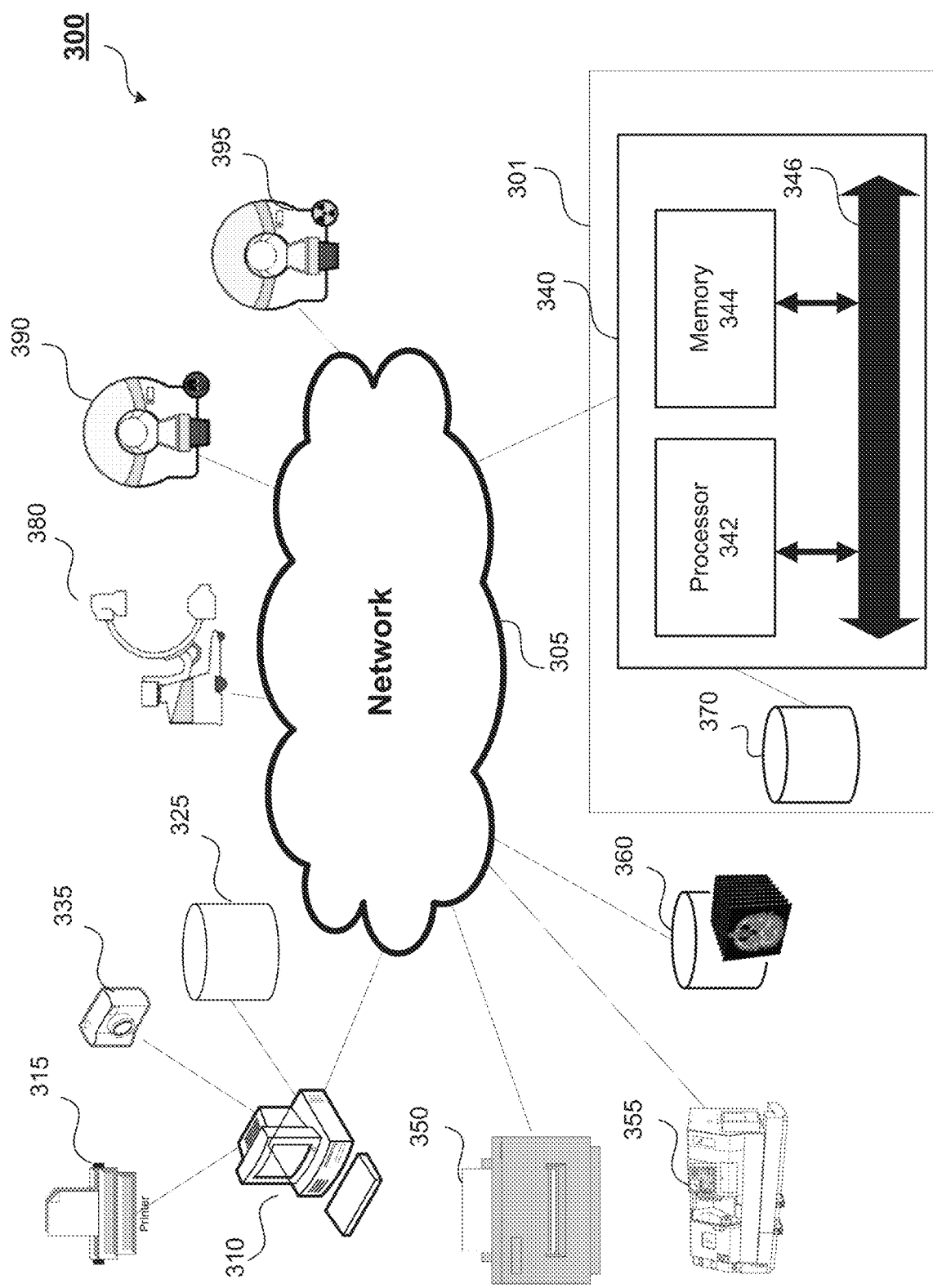
FIG. 3 is a schematic representation of a system on which one or more embodiments of the present disclosure may be practised.

FIG. 3 is a schematic block diagram representation of a system 300 on which an embodiment of the present disclosure may be practised. The system 300 relates to a medical or biomedical application, in which surgical plates, splints, braces, supports, and the like may be customised to produce patient specific devices. The system 300 includes a computing device 310 that may be operated by a user. The computing device is coupled to a 3D printer 315, a camera 335, and a first database 325.

The 3D printer 315 is able to receive an output file of a customised device from the computing device 310 and produce an instance of that customised device. The camera 335 may be implemented as a traditional camera with a lens for capturing an image of a patient. The image can then be processed using software executing on the computing device 310 to calculate parameters pertaining to that patient. Alternatively, the camera 335 may be implemented as a laser or structured light scanner to generate a surface scan of a region of a patient.

The first database 325 stores models of base parts that may be customised to fit a patient. As noted above, such base parts may include splints, braces, surgical plates, cups, rods, cutting guides, and the like. The first database 325 may also store predefined sets of 'source' points for each of the base parts. These source point files are associated with the base part files and are loaded into the software contemporaneously with the base part. The first database 325 may also store sets of target shapes. In the case in which the system is used for customising surgical guides, the sets of target shapes may relate to normal bones for a range of different body shapes and sizes, in which case the user can choose a normal bone to represent a desired post-operative state, or this step can be automated so that the bone model most suited to the patient bone is used.

In the system 300, the computing device 310 is coupled to a communication network 305, which enables communication between the computing device 310 and other computing devices. The communications network 305 may be implemented using one or more wired or wireless transmission links and may include, for example, a cellular telephony network, a dedicated communications link, a local area network (LAN), a wide area network (WAN), the Internet, a telecommunications network, or any combination thereof. A telecommunications network may include, but is not limited to, a telephony network, such as a Public Switch Telephony Network (PSTN), a cellular (mobile) telephone cellular network, a short message service (SMS) network, or any combination thereof.

In the example of FIG. 3, the system 300 includes an x-ray machine 380, a magnetic resonance imaging (MRI scanner) 390, and a CT scanner 395, each of which can capture images relating to portions of a patient and upload those images to the computing device 310 via the communications network 305.

The user is able to access the computing device 310 to select a model of a base device from the database 325, import a set of parameters for customising the device, based on information input by the user or derived from images captured by the camera 335 or the x-ray machine 380 or the MRI scanner 390 or CT 395 scanner or derived from the first database 325, and then generate a digital model of a customised device derived from the base device, in accordance with the method of FIG. 1 implemented as a computer program executing on one or more processors of the computing device 310. The generated digital model is available for output as a computer file suitable for use by a 3D printer, such as the 3D printer 315 or an external 3D printer 350 coupled to the communications network, or other computer numerical control (CNC-CAM) device 355, such as a milling machine, bending machine, router, saw, hole-punch, lathe, hydraulic press, and the like.

In the example of FIG. 3, the system 300 further includes an external database 360 coupled to the communications network 305, wherein the external database 360 stores one or more digital models, available for selection by the user accessing the computing device 310. In some circumstances, the digital models may be derived from CT, MRI or X-Ray data. In an alternative implementation, the digital models may be derived from other sources, such as computer programming, scanning, or the like. The external database 360 also stores predefined sets of 'source' points for each of the base parts. These source point files are associated with the base part files and are loaded into the software simultaneously with the base part. The external database 360 optionally stores sets of target shapes, such as the set of normal bones described above in relation to the first database 325. Such target shapes may optionally be stored with associated sets of 'target points'.

The system 300 further includes a central server 301, which in this implementation has a processor 342 and a memory 344 coupled to a bus 346 to enable communication therebetween. The central server 301 also includes a server database 370 for storing models of base device geometries, sets of target shapes, or a combination thereof. The server 301 is coupled to the communications network 305.

In one arrangement, the server 301 hosts a webpage that is accessible by the user of the computing device 310, via a web browser executing on the computing device 310. The user is able to navigate a user interface presented by the server 301 to the computing device 310, in order to select a desired application, such as a particular operation or procedure or condition, and then select from one or more options relating to the selected application in order to select a model of an existing base device. The user is then able to input or upload parameters to govern the customisation of the base device, whereupon a computer program stored in memory 344 executes on the processor 342 to implement the method of FIG. 1 to transform the base shape in accordance with the parameters to generate a model of a customised device. The user can then select to 3D print or CNC machine the customised device using a selected material on either one of the 3D printer 315 and the external 3D printer 350 or other CAM machine, such as the CNC machine 355.

Figure 4:
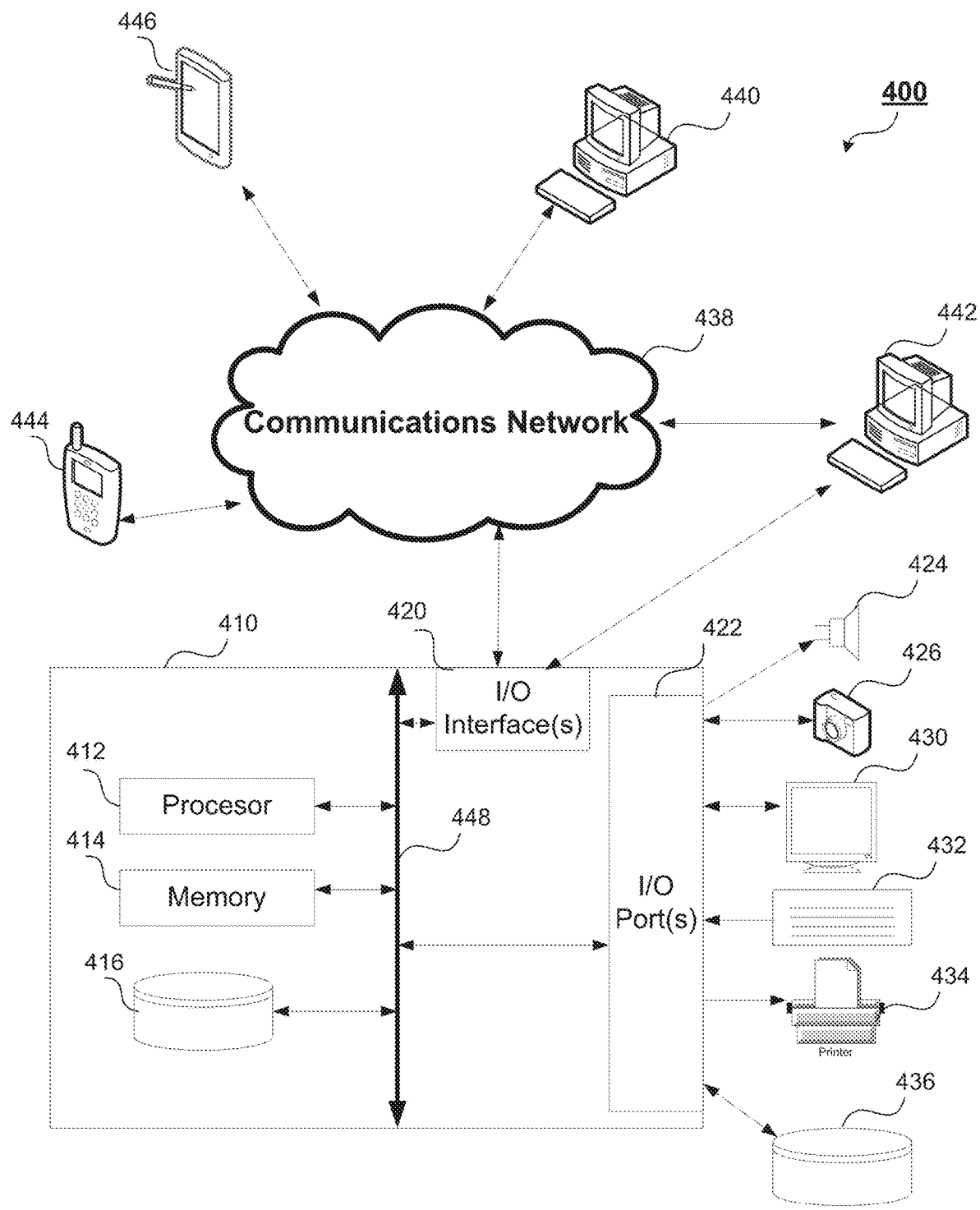
FIG. 4 is a schematic block diagram representation of a system that includes a general purpose computer on which one or more embodiments of the present disclosure may be practised.

The customisation system of the present disclosure may be practised using a computing device, such as a general purpose computer or computer server. FIG. 4 is a schematic block diagram of a system 400 that includes a general purpose computer 410. The general purpose computer 410 includes a plurality of components, including: a processor 412, a memory 414, a storage medium 416, input/output (I/O) interfaces 420, and input/output (I/O) ports 422. Components of the general purpose computer 410 generally communicate using one or more buses 448.

The memory 414 may be implemented using Random Access Memory (RAM), Read Only Memory (ROM), or a combination thereof. The storage medium 416 may be implemented as one or more of a hard disk drive, a solid state "flash" drive, an optical disk drive, or other storage means. The storage medium 416 may be utilised to store one or more computer programs, including an operating system, software applications, and data. In one mode of operation, instructions from one or more computer programs stored in the storage medium 416 are loaded into the memory 414 via the bus 448. Instructions loaded into the memory 414 are then made available via the bus 448 or other means for execution by the processor 412 to implement a mode of operation in accordance with the executed instructions.

One or more peripheral devices may be coupled to the general purpose computer 410 via the I/O ports 422. In the example of FIG. 4, the general purpose computer 410 is coupled to each of a speaker 424, a camera 426, a display device 430, an input device 432, a printer 434, and an external storage medium 436. The speaker 424 may be implemented using one or more speakers, such as in a stereo or surround sound system. In the example in which the general purpose computer 410 is utilised to implement the computing device 310 of FIG. 3, one or more peripheral devices may relate to a 3D printer, a CNC milling machine, a CNC lathe, a CNC router or saw, a camera, an external storage medium, an x-ray machine, a CT scanner, or an MRI scanner connected to the I/O ports 422.

The camera 426 may be a webcam, or other still or video digital camera, and may download and upload information to and from the general purpose computer 410 via the I/O ports 422, dependent upon the particular implementation. For example, images recorded by the camera 426 may be uploaded to the storage medium 416 of the general purpose computer 410. Similarly, images stored on the storage medium 416 may be downloaded to a memory or storage medium of the camera 426. The camera 426 may include a lens system, a sensor unit, and a recording medium. The camera 426 may be a digital camera, an x-ray machine, an MRI scanner, a CT scanner, or other imaging device.

The display device 430 may be a computer monitor, such as a cathode ray tube screen, plasma screen, or liquid crystal display (LCD) screen. The display 430 may receive information from the computer 410 in a conventional manner, wherein the information is presented on the display device 430 for viewing by a user. The display device 430 may optionally be implemented using a touch screen to enable a user to provide input to the general purpose computer 410. The touch screen may be, for example, a capacitive touch screen, a resistive touchscreen, a surface acoustic wave touchscreen, or the like.

The input device 432 may be a keyboard, a mouse, a stylus, drawing tablet, or any combination thereof, for receiving input from a user. The external storage medium 436 may include an external hard disk drive (HDD), an optical drive, a floppy disk drive, a flash drive, or any combination thereof and may be implemented as a single instance or multiple instances of any one or more of those devices. For example, the external storage medium 436 may be implemented as an array of hard disk drives.

The I/O interfaces 420 facilitate the exchange of information between the general purpose computing device 410 and other computing devices. The I/O interfaces may be implemented using an internal or external modem, an Ethernet connection, or the like, to enable coupling to a transmission medium. In the example of FIG. 4, the I/O interfaces 420 are coupled to a communications network 438 and directly to a computing device 442. The computing device 442 is shown as a personal computer, but may be equally be practised using a smartphone, laptop, or a tablet device. Direct communication between the general purpose computer 410 and the computing device 442 may be implemented using a wireless or wired transmission link.

The communications network 438 may be implemented using one or more wired or wireless transmission links and may include, for example, a dedicated communications link, a local area network (LAN), a wide area network (WAN), the Internet, a telecommunications network, or any combination thereof. A telecommunications network may include, but is not limited to, a telephony network, such as a Public Switch Telephony Network (PSTN), a mobile telephone cellular network, a short message service (SMS) network, or any combination thereof. The general purpose computer 410 is able to communicate via the communications network 438 to other computing devices connected to the communications network 438, such as the mobile telephone handset 444, the touchscreen smartphone 446, the personal computer 440, and the computing device 442.

One or more instances of the general purpose computer 410 may be utilised to implement a server acting as a networked computing device to implement a device customisation method in accordance with the present disclosure. In such an embodiment, the memory 414 and storage 416 are utilised to store data relating to warping of base devices based on input parameters. Software for implementing the device customisation system is stored in one or both of the memory 414 and storage 416 for execution on the processor 412. The software includes computer program code for implementing method steps in accordance with the method of FIG. 1 described herein.

Two aspects of 3D printing make it particularly appealing for use in the production of patient specific devices:
1) The method of manufacture means that increased geometric complexity costs no extra to produce than simple geometries. In cases where increased geometric complexity is employed, for example, to reduce part weight whilst maintaining suitable device stiffness, such as through optimised internal lattice design, then printing the complex part is cheaper than printing a geometrically simple solid part, as less raw material is used to create the part. In this way, 3D printing enables increased design complexity.
2) It is time consuming, and thereby costly, in traditional robotic construction line manufacturing processes to set the production line for the manufacture of a new design. In the case of moulding and casting manufacturing processes, it is costly to produce the initial mould of the device design. Once the production line or mould is set up, it becomes much cheaper to produce each individual device. This is not the case for the additive manufacturing process, where it costs the same per unit (CAD time considerations aside) to manufacture, for example, 100 customised versions of a device as 100 copies of the same (master) design. This pre-disposes the additive manufacturing process to be applied to manufacturing devices where there are demonstrable benefits to device customisation. One such field is the biomedical device industry, where numerous studies have shown that patient specific planning, guide and device use improves clinical outcomes for the patient.

Representation in CAD of 3D Surfaces

Currently, there are two predominant ways in which 3D surfaces are represented in CAD: parametric surfaces and isosurfaces (polygon tessellated, often triangulated, points). Both describe different types of boundary representations (i.e., surfaces that enclose a volume) and both are made up of 3D coordinate points. Boundary representations are different from volumetric image data, which are obtained by thresholding greyscale values from DICOM images acquired by CT or MRI scanning.

Parametric Surfaces

Figure 16A:
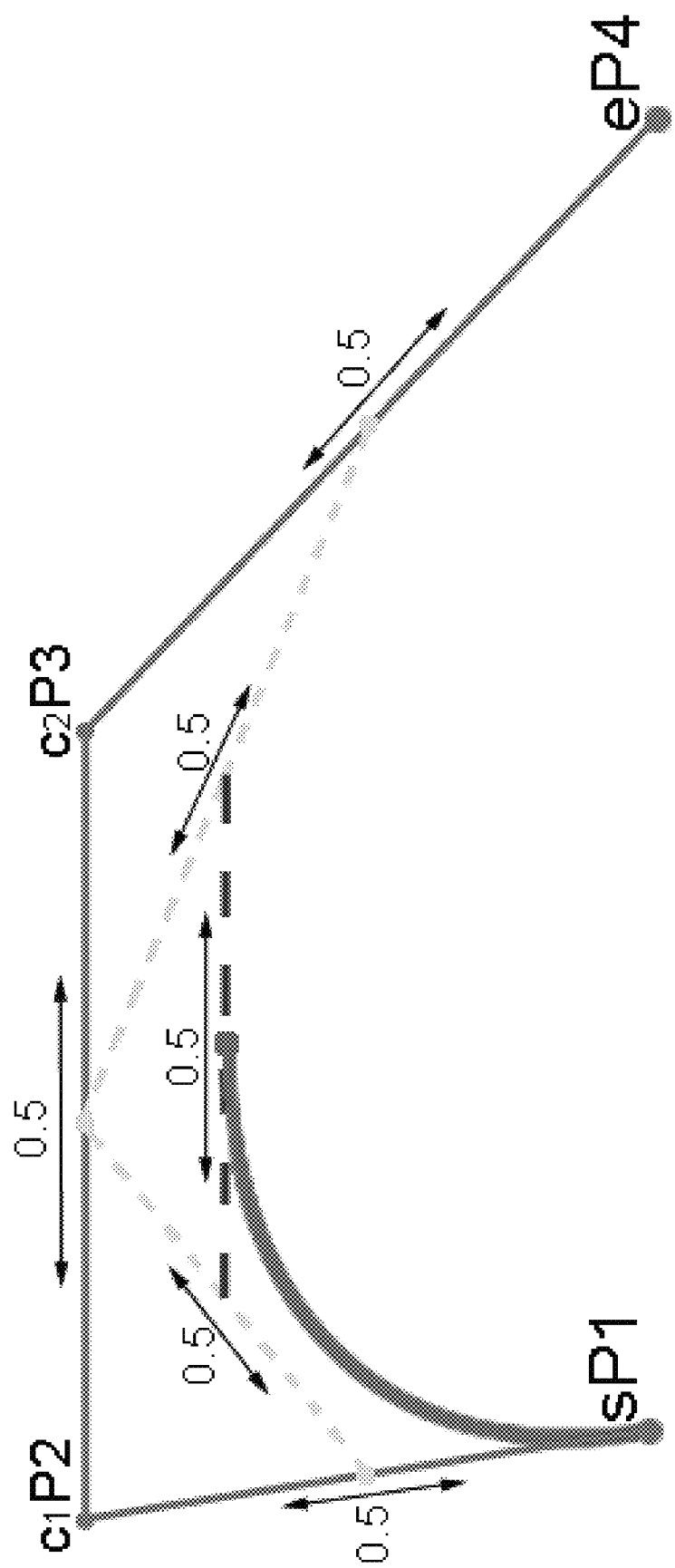

Parametric surfaces can be built from curves and/or surfaces, such as Bezier, B-spline, and non-uniform rational B-spline (NURBS) curves/surfaces. Curves and surfaces in these cases are determined by three different types of points:
a) points (sometimes, in biological cases, landmarks) that define the boundary perimeter (surfaces) or ends (curves); surfaces/curves are constrained to meet these points in 3D space (see FIG. 16A for an example of construction of a NURBS curve, in which points 1 (sP1) and 4 (eP4) are boundary defining points, where s stands for start and e stands for end);
b) (weighted) control points (weighted to determine the level of control over the surface curvature each of the control points has); the curvature of the surface/curve within the boundary defining points is determined by the positioning, number and relative weighting of the weighted control points (FIG. 16A shows c1P2 and c2P3 as control points in between the boundary defining start (sP1) and end (eP4) points. The (dark grey solid line) curve's path is dictated by the inter-relation between the boundary defining points and the control points. FIG. 16A shows the curve at the 0.5 point between sP1 and eP4. The curve's position at 0.5 is given by the 0.5 position along the (larger) dashed line, which is defined as the connection between the points 0.5 of the way along both dotted lines, which are (in turn) defined as the connections between the points 0.5 of the distance between sP1→c1P2 and c1P2→c2P3 (resulting in the left hand dotted line) and 0.5 of the distance between c1P2→c2P3 and c2P3→eP4 (resulting in the right hand dotted line).); and
c) in some surfaces/curves, the curvature is also controlled by 'knots', which constrain the curvature of the surface when close to a knot point (This branch of mathematics, and its associated terminology, that describes surfaces in this fashion comes from wooden boat building, where the curvature of each of the beams that go to make up the ribs of a boat's hull, and give the boat its external hull shape, was created by fixing each wetted beam at either end and hanging weights to control how the beam bows, whilst accounting for stiff areas in the beam created by knots in the wood).

Bezier, B-spline surface and NURBS surfaces take the same spline (polynomial) curvature maths and extend it to surfaces. Thus, the exact position of a surface is calculated by resolving a set of polynomial equations incorporating the boundary points, weighted control points, and knot points (if present). Therefore, a surface represented parametrically is a mathematical function, with curves being infinitely divisible (see FIG. 16B for an example of a CAD NURBS surface representation).

Common computer 3D file formats that spline curves, Bezier and NURBS surfaces can be stored in include IGES and STEP files. To be made suitable for 3D printing, these file formats must be converted to triangulated point formats, such as .wrl or .stl. However, generic/existing base parts described by these surfaces can still be customised by adjusting and/or adding control points, knot weights, and the like. This is currently how altered, or customised, parametric CAD devices are made. Such methods can, indirectly, use points taken from a patient's anatomy (see below).

Isosurfaces

Isosurfaces are surfaces made by 3D points, or vertices, with associated connectivity lists. The connectivity lists tell software which points and in what order these points can be used to construct polygon surfaces. Polygon surfaces can be constructed of three or more vertices, but only when polygon surfaces are constructed of three vertices alone, in other words as triangles, is it assured that all polygons are planar (see FIGS. 16C-E for a triangulated representation of the surface shown in FIG. 16B).

T. Rado (1925) showed that, with small enough triangles, every surface geometry has a triangulation, in that a surface can be accurately represented using a triangulated vertex approach. This is not the case for polygons constructed of higher numbers of vertices.

Figure 16D:
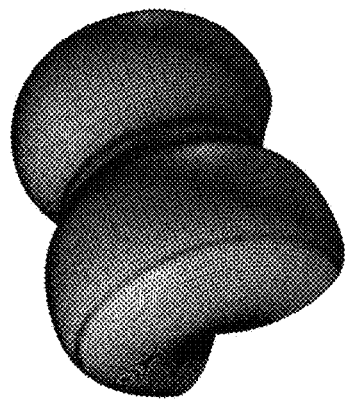
Figure 16D:
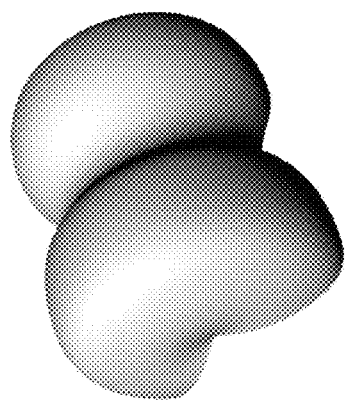
Figure 16D:
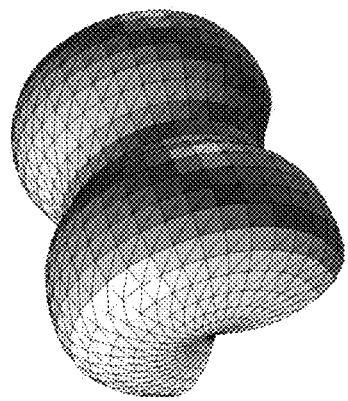
Figure 16D:
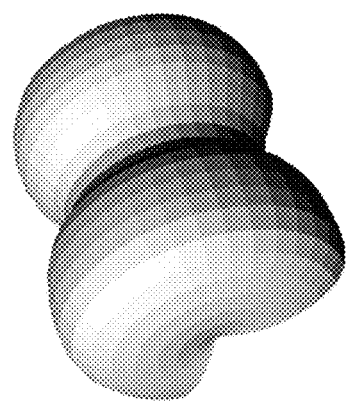
Figure 16E:
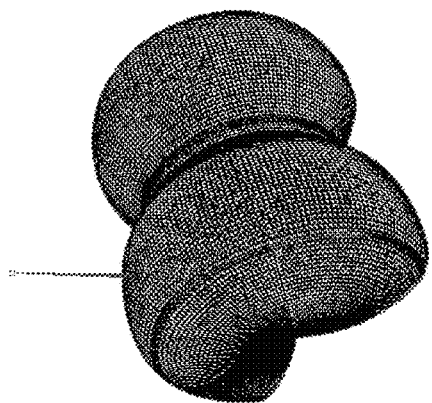
Figure 16E:
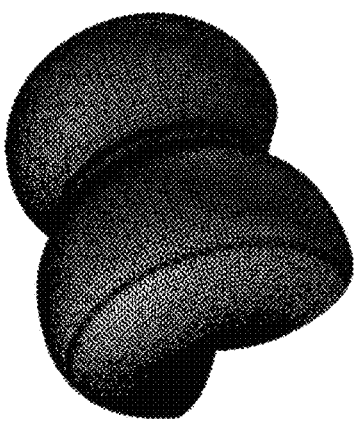
Figure 16E:
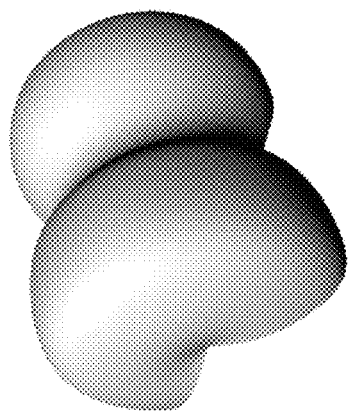

The Significance of Differences Between Parametric and Triangulated Surface CAD Files The differences between surfaces modelled parametrically compared to triangulated surfaces represented in CAD models are not trivial, but are fundamental to how a surface is represented in a 3D model, and what movement of a point will do to the model. If a single point is moved in a parametric surface, such as a NURBS surface, a very different result is achieved than moving a single point on a triangulated surface of the same shape (see FIG. 16 B compared to FIGS. 16C and E). FIG. 16E shows a high resolution triangulated surface representation that is comparable in shape to the parametric (NURBS) surface in FIG. 16B. FIG. 16C is a low resolution triangulated surface of the same shape (as shown in FIGS. 16D and E) in which the effects on the device's surface of moving a single point are more easily observed than in the high resolution triangulated surface shown in FIGS. 16D and E (the effects of surface discontinuity, potential surface hole creation, and spiked morphology are the same in the high resolution triangulated surface).

As the curvature of a NURBS surface is governed by the position of the control points, movement of a single (control) point results in a smooth deformation of the surface (FIG. 16B). Importantly, the structure (the combination of a number of surfaces) as a whole remains intact and no holes, surface discontinuities or disruptions are introduced by the movement of the control point and the deformation of the surface.

Another important point to note about this method of shape change is that only the surface that the control point is linked to changes shape as the control point is moved. In other words, parametric modelling using control points does not affect the whole shape of the device. In FIG. 16A, only the surface associated with the moved control point alters shape, but this has consequences for the device as a whole, for example on the thickness, surface area, and volume of the device.

The control points in a parametric surface file have a specific structure (ordering, or template) within the CAD file and are integral to the CAD file itself. FIG. 16A shows that not all points within a parametric CAD file have the same effect on a parametric curve. This extends to parametric surfaces as well. Some parametric points are boundary defining points, whereas other points control the curve/surface curvature. The ordering and labelling of these different types of points within a parametric curve/surface file is specific and non-interchangeable.

Although points from a target shape, for example a patient, can be used to guide the parametric surface point positions, this is achieved by moving the parametric surface control points to match point positions of/on the target shape. The control points that define the parametric curve/surface curvature itself (i.e., within the parametric file) are part of the parametric file.

This is different to the present disclosure, wherein the control points (source and target points) are separate from the base device file. The source and target (control) points in the present disclosure effectively determine the warping of the space the base device is in to achieve the warped device. As these control points are separate from the base device itself, different base devices can be warped by the same source and target (control) points (see below and FIGS. 17A-H).

Another typical way in which a parametric curve/surface file, such as a NURBS curve/surface, can be customised to fit patient anatomy is to fit geometric shapes, such as a circle, sphere or cylinder, to patient data points and determine parameters, such as curve radius, from these fitted shapes. For example, the curve radius of the femoral condyle can be measured from a planar x-ray, via a fitted circles, CT or MRI slice, or 3D reconstruction based on CT or MRI data, via fitted spheres or cylinders. These parameters can then be used to adjust the control point positions of the parametric file, so that the parametric curve/surface matches the patient parameter.

This method cannot, typically, be applied to alter the shape of other forms of boundary representation surfaces, such as the triangulated point surfaces obtained from 3D reconstructions of CT, MRI slice data, by moving the surface points in the same way (see FIG. 16B, for the results of a parametric surface adjustment via a point, compared to FIG. 16C, for the results of a triangulated surface adjustment via a point).

Triangulated surface files are the type of CAD files that are used by 3D printers.

The same shape that is represented by a parametric CAD surface can be represented by the triangulated vertex CAD method (See FIG. 16B for a parametric representation of the surface, compared to FIGS. 16D and 16E for a low and high resolution triangulated representation of the same surface).

The points making up the triangulated surface affect the surface in different ways to the points governing the parametric surface. If a single point in FIG. 16C (or E), which is in a similar position to the point in FIG. 16B, is moved by a similar magnitude in a similar direction to the point in FIG. 16B, the resulting effect on the triangulated representation of the surface is very different, both visually and structurally, to the effects on the parametric surface. In the triangulated surface, only the triangle, or triangles (depending on how the surface is constructed in the CAD software), in which the moved point is a member alter their shape. The remainder of triangles making up the structure's shape remain unaltered. This leads to an un-smooth change in the device shape (a spike in FIGS. 16C and E). This can also lead to the creation of holes, surface discontinuities or disruptions that could result in the triangulated representation of the structure being unsuitable for 3D printing (as visible in the two right-hand images of FIG. 16C).

Currently, the majority of medical 3D surface models are created from serial DICOM data (CT and MRI). The 3D surface models created in this way are most frequently tessellated surface models, made using the marching cubes or wrapper algorithms, or variations of these. There is a natural workflow from these models to 3D printing, as the 3D printing files are always represented as these same triangulated surfaces. It is not possible to create parametric surface models directly from CT data, except by secondarily fitting parametric surface 'patches' to the tessellated surface. This is an imperfect solution, the results of which need user intervention, manipulation and checking. Further, it is very difficult, or near impossible, to 'reverse engineer' the true CAD surface structure, for example of a hierarchical parametric CAD model, from a triangulated file in a single, automated step without considerable user intervention.

Boundary representation models, both parametric and triangulated surfaces, can be 'solid filled' to create volume meshes suitable for entry into Finite Element Analysis (FEA). One approach that is commonly employed by engineers, when working with anatomical data acquired via medical scanning, is to use the corner points of each voxel (CT or MRI, a voxel is a 3D pixel) to construct hexagonal elements. This allows data in a CT or MRI scan, such as greyscales that can be correlated with material properties of different parts of the scan, to be translated directly into engineering models without the necessity of constructing boundary representations of the different structures. However, the resulting models do not capture the shape of the structures accurately. This is because the true outline of the structure that was originally scanned will naturally transect voxels. Boundary representation using triangulated polygons can capture this true shape much more accurately than voxel representations. This becomes important when accurate shape of the scanned structure is desired.

Additionally, a triangulated boundary representation can be solid meshed using the simplest solid geometry: the 4 noded tetrahedron. Hence, FEA models constructed from 4 noded tetrahedrons that use as their base the triangulated polygon boundary representation (or surface triangles) will more accurately represent the true geometry of the structure being modelled, and will be computationally lighter than the eight noded hex elements derived directly from DICOM voxel data.

Accuracy is defined by high precision and high trueness. Precision is akin to a design/engineering tolerance, a screen/computer monitor resolution, or the pixel count in a digital camera. Trueness is how closely the representation of the underlying structure is represented by the technology capturing it. For example, a fish eye lens may give a highly precise photo with low trueness of the real life geometry captured in the photo.

Hence, many 3D software programs represent boundary isosurfaces obtained through either surface scanning (laser, structured light, photogrammetry) or volumetric scanning (CT, MRI, or ultra sound) as triangulated point surfaces. For the volumetric scanning methods, these are the boundary representation surfaces that are constructed from thresholding DICOM image data, often through the Marching cubes or Wrapper algorithms, or variants thereof.

Currently, all additive manufacturing machines accept triangulated vertex files for additive manufacturing. These files are usually in the STereo Lithography (.stl) file format, but more recently some manufacturers of additive manufacturing machines (e.g., Stratasys) are also including Virtual Reality Modelling Language (VRML, .wrl) to allow for surface colour information to be conveyed to the additive manufacturing machines.

Currently, additive manufacturing machines do not accept parametric surface (e.g., IGES and STEP) files. Conversely, Computer Numerical Control (CNC) milling machines accept parametric surface files, such as IGES and STEP files, but generally not triangulated vertex files such as STLs. Parametric surface files can be converted to triangulated vertex files relatively easily, so devices designed using hierarchical parametric modelling methods, such as those designed in Rhino, Pro/Engineer or SolidWorks, can be 3D printed. However, it is not possible to convert triangulated vertex files to parametric surface files easily. Instead, B-spline curves, Bezier or NURBS surfaces are fitted to the triangulated isosurfaces to convert to the CNC machinable file formats. This process does not always give satisfactory results, often necessitating user interaction to define surface boundaries or particularly when attempting to fit parametric surfaces to a design device geometry, which often include sharp edges.

Warping by Interpolation Functions Using Source and Target Points, Including, but not Limited to: Thin Plate Splines, Bessel Functions, Radial Basis Interpolation, Moving Frames Linear Optimisation and Other 'As Rigid As Possible' Deformation Methods The present disclosure provides a method of altering an original base shape to match a target shape. There are several ways to achieve this, including the Finite Element Method and multivariate spline methods, as well as the warping interpolation function methods detailed here. Both the Finite Element Method and the multivariate spline method are usually based on resolving simultaneous equations for the points making up each of the triangles in a mesh to calculate the overall distortion of the mesh. This rapidly becomes computationally heavy and, therefore, slow when meshes have large numbers of points, such as in geometrically accurate anatomical or biomedical device models. In contrast, the warping interpolation function methods do not require triangulation and so are much faster to calculate.

The interpolation functions (including, but not limited to polynomial functions, such as thin plate splines), Bessel functions, radial basis functions, moving frames linear optimisation and other 'as rigid as possible' (ARAP) deformation functions can all be calculated from fewer than the total points in a model. The triangulation and connectivity of the model's points are not needed, only the correspondence between original (source) and target positions and so the method is mesh free and independent. In each method, an interpolation function is calculated that transforms the original point positions to their corresponding target positions. The radial basis (multivariate) functions are approximated as a linear combination of the univariate functions that are radialised so as to be applicable in more than one dimension (3 in this case). The univariate radial basis functions can be Thin Plate Spline function, but other polynomial functions may equally be used, such as Bessel functions, and simple distance based functions such as $1/(distance^2)$, often written as $1/r^2$. In the case presented here, the radial basis functions form an interpolation, or warping, function between known source and target points. This interpolation function can subsequently be used to alter the position of any point on the original shape to that of the warped/customised shape according to the relative positioning of the points in source and target positions.

The method presented here effectively adjusts, or warps, the dimensions of uniform Euclidean space using different interpolation functions, which allows control of the degree of smoothing and the range of influence of a control point, to create warped space. The triangulated surface model is then entered into this warped space and the functions controlling the warping of the space control the warping of the triangulated surface model (FIGS. 17A-H).

The method presented here is not an affine adjustment of shape, which is a shear of Euclidean space. An affine adjustment of shape can be achieved by scaling the axes of the Euclidean space in which the model resides by different ratios to achieve a different shaped object.

Radial basis functions (with some exceptions) usually require source and target points to be organised into grids. This is not always convenient or even possible, depending on the original device geometry.

The moving frames linear optimisation and other rigid deformation methods, such as 'As Rigid As Possible' (ARAP), on the other hand, do not require this grid level of organisation of original (source) and target points, and so can be used to customise complex geometries using disorganised source and target points.

As the functions used to warp/customise the original base geometry are all meshless and their construction depends only on source and target points, the warped/customised geometry can be calculated very fast compared to other mesh based warping methods.

Figure 17A:
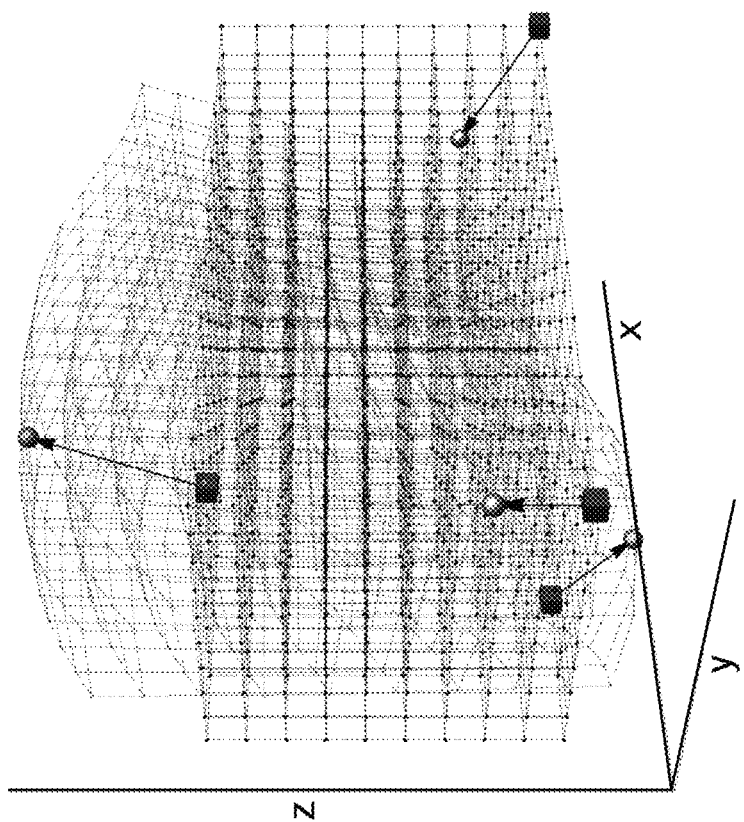
Figure 17A:
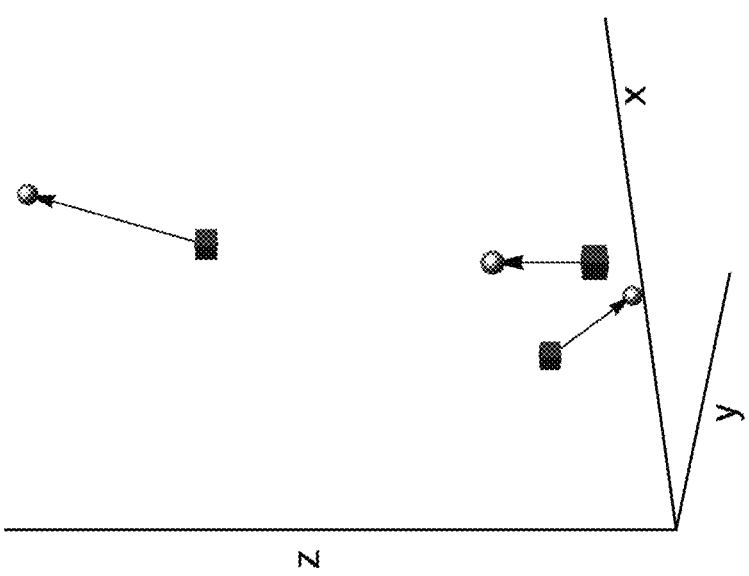
Figure 17B:
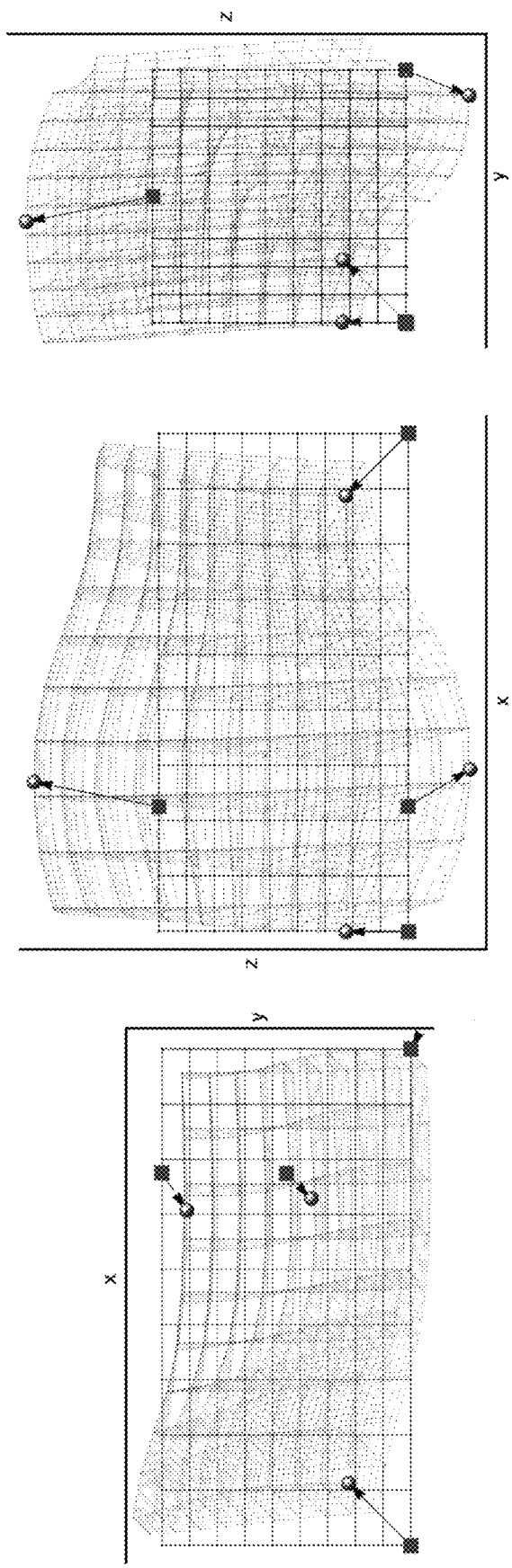
Figure 17E:
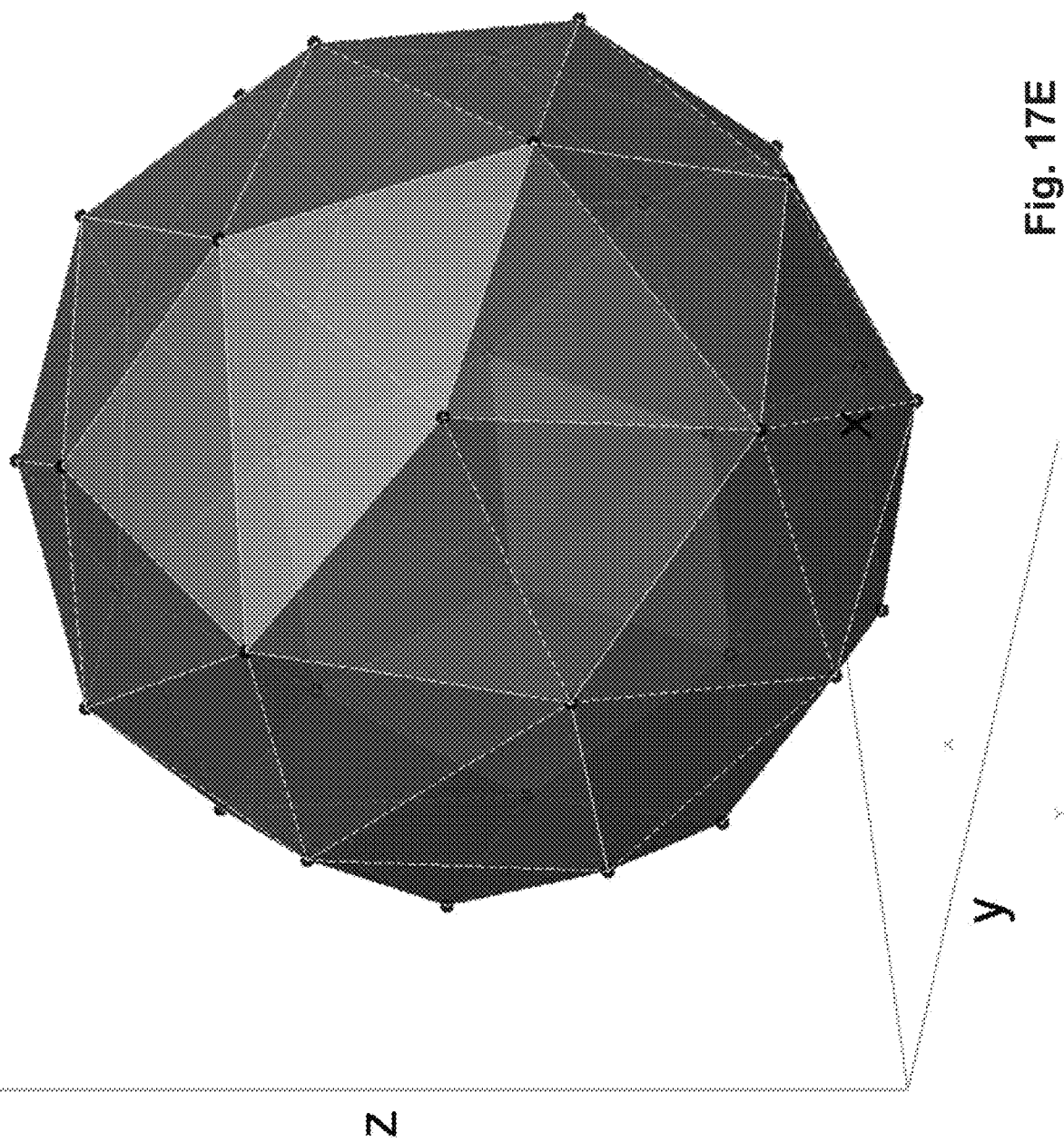
Figure 17F:
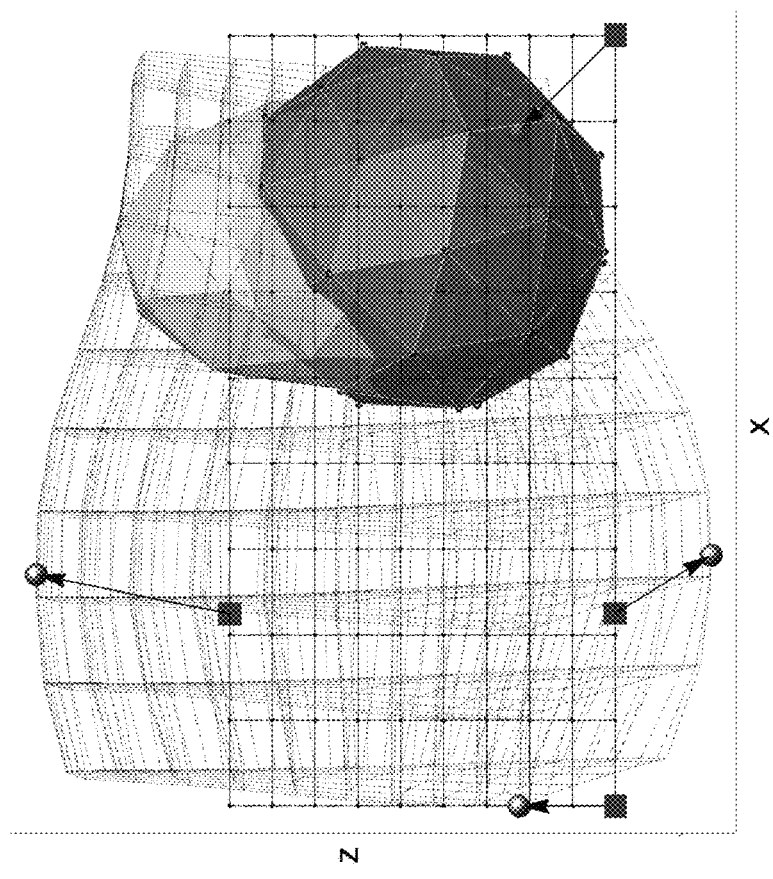
Figure 17F:
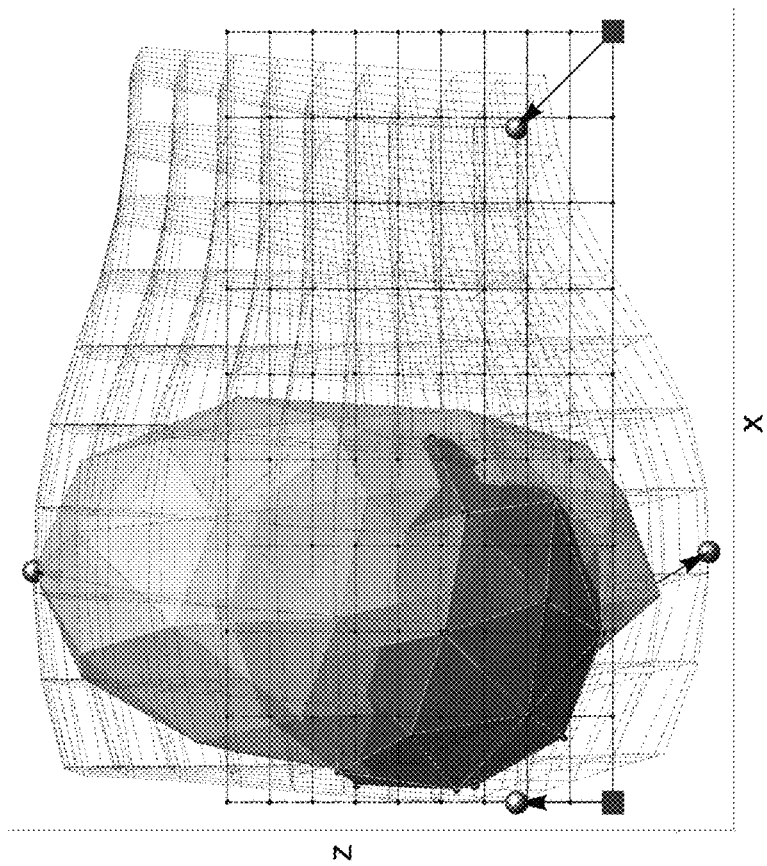
Figure 17G:
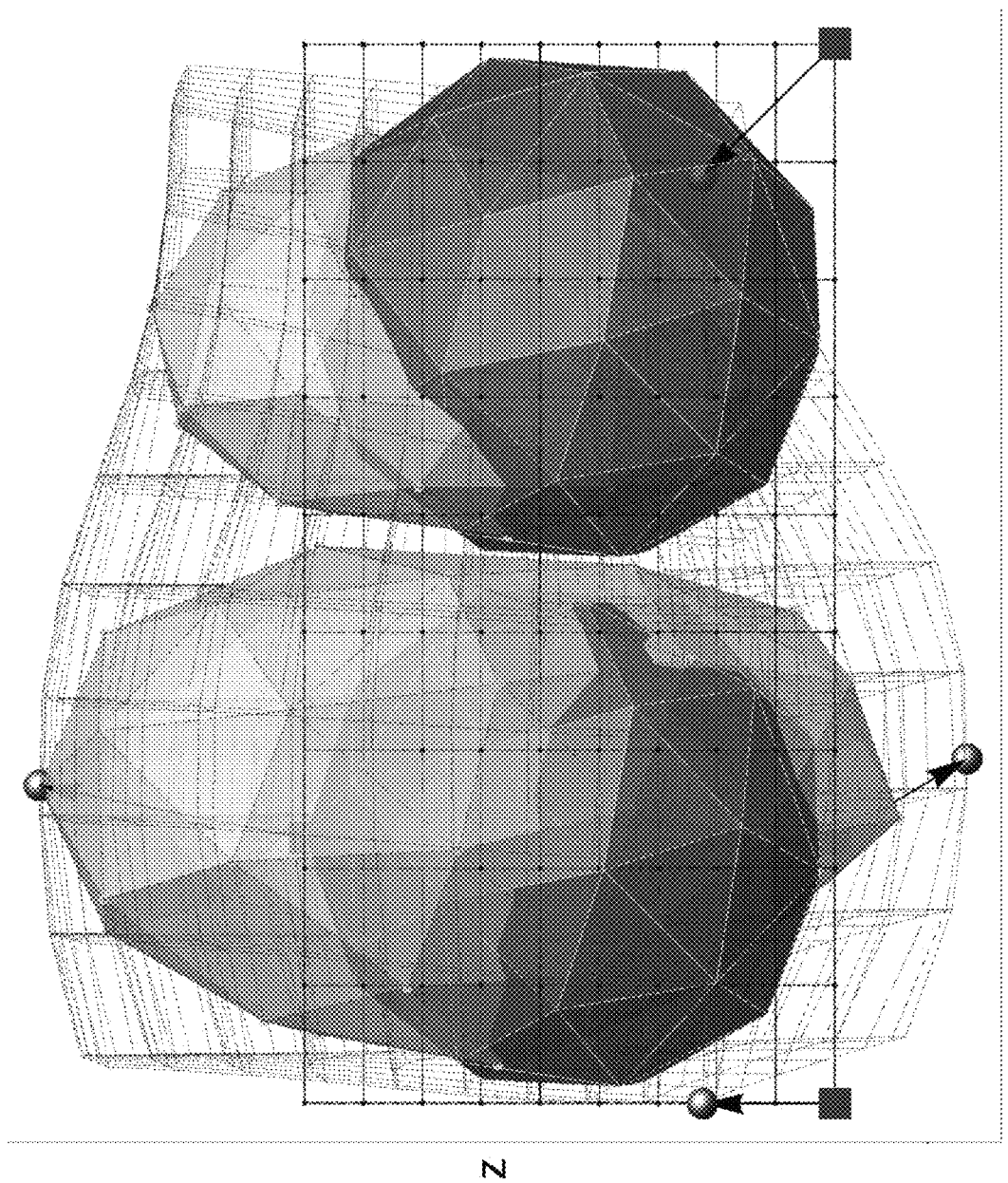
Figure 17H:
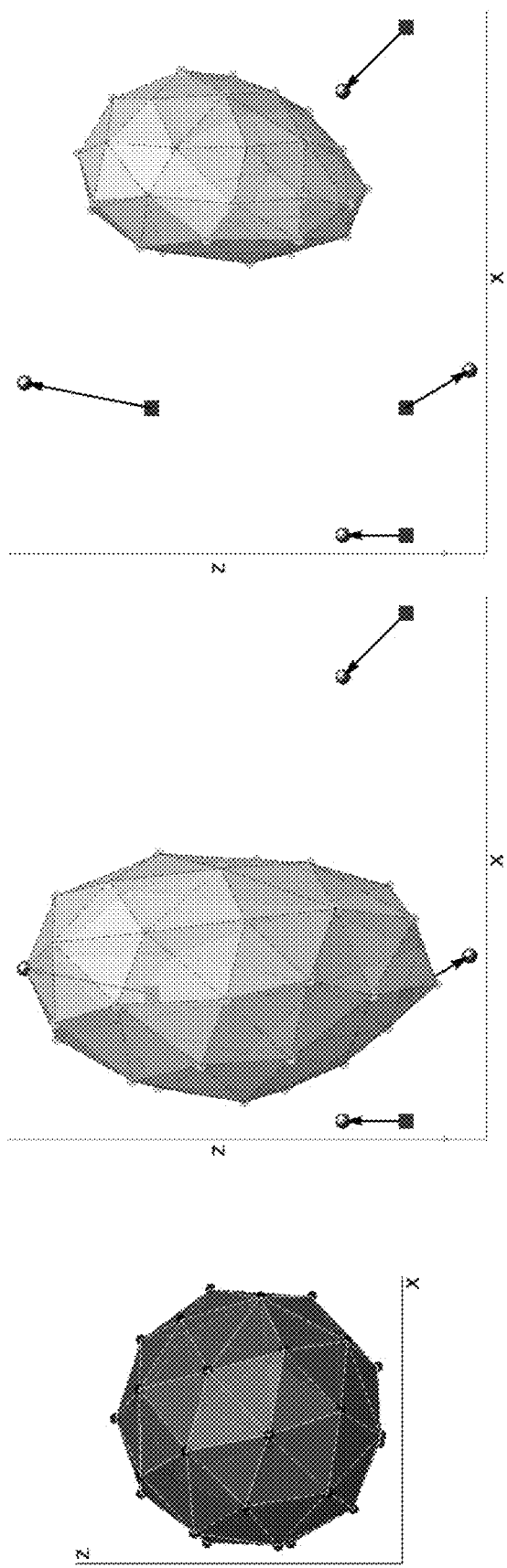

The method described here does not identify homologous points between bone and device/bone and bone or at all during the work flow. Instead, the method defines 'source' points associated with, but not necessarily part of, the base device, then projects these same points until they contact, or intersect, the surface of the target bone/structure. The points in this end position are termed the 'target points'. The warping part of the function is determined by the change in positions (relative to one another) of these source points, with the interpolation part of the function determining how the distance of the base device points from the source points affects the relative influence of each of the source points on the device points (FIGS. 17A and B). In an alternative arrangement, the method of the present disclosure is used to project target points from a target device, such as a target bone or structure, back to source points on a generic device. In such an arrangement, one can imagine the target device as the "source" and the generic device as the "target".

The warping function is interpolative, as the precise effect on the base device's shape depends on the proximity of the different regions of the base device to the different source points. This is illustrated by the warped grids in FIGS. 17A-C, F and G. The 'source', or start, positions of the points are shown by small black cubes. The target positions are shown by grey spheres with black arrows showing the desired movement of the cubes. The dark cuboid grid illustrates the Euclidean 3D space that the source points are in. The lighter grey curved grid illustrates how this uniform Euclidean space must bend, or warp, in order to move the source points to their target positions. Note that this warping of space is non-uniform along each axis and between the axes. This means that the resulting shape of a device warped using this method depends on where in the warped space the device is placed (FIGS. 17E-H). The same base part, or shape, can result in a different warped shape of this base part if it is entered into the warped space at a different point (FIGS. 17E-H). FIGS. 17E-H show how the end warped result of a base part, a sphere shape (FIG. 17E), can depend on where in the warped space the base part is entered (compare the left and right hand side results of FIGS. 17F-H).

How the space bends in between the control points is determined by the interpolative function (e.g., Thin Plate Spline, polynomial function, Bessel function, $1/r^2$). In this way, part of the interpolative function's effect is to determine how smooth the geometry of the final warped part is. As Rigid As Possible and other rigid warping functions generally result in smoother and more intuitive warped geometries than functions such as simple distance (from source point) functions (e.g., $1/r^2$).

This use of the term 'interpolation' as used here differs from another use of the same term in the field where interpolation describes the generation of additional points in between a designated start point and endpoint. This type of interpolation can be used to subdivide meshes, resulting in the same geometry being represented by more points and triangles. This second use of interpolation can also be used to fill holes, for example in 'lofting' between a first hole's edge points and a second, adjacent, hole's edge points.

The method described herein uses source and target points to control warping of the space that the device is in. This is different to the method of adjusting a control point in the CAD file, which other methods that customise parametric CAD models currently use. The method described herein is abstracted from the device file and so the same warped space can have any device 'dropped into it' (see FIGS. 17C and D compared to FIGS. 17F-H for the results of warping different base shapes into the same warped space). The points controlling the warping of the space, via a function, are completely separate from the device and/or bone files, which is not the case for the control points in a parametric CAD model. In a parametric CAD model, the control points are an integral part of the model.

Once the warping interpolation function is established, it can then be applied to the points making up the original device's triangulated mesh to achieve their warped/customised positions. As long as triangulated point ID correspondence between the base part and warped part is maintained, then the points in the warped part have the same connectivity (triangulation) as the original device. In this way, the method described herein is accurate, but also computationally fast and with relatively low memory requirements, and can be used to customise a triangulated surface geometry in a smooth manner. Additionally, the method allows original design features of the device, such as device thicknesses, edge fillets and the like, to be maintained during the customisation process. This is not possible with either bottom-up custom design processes, where each feature has to be created for every new custom device, or with subtractive customisation of a device, where the patient anatomy is Boolean subtracted from the surface of the device that will contact the patient anatomy to leave a 'negative' of the anatomy in the device, but which does not control device thickness, or prevent design features from being disrupted by the subtraction process.

The source point positions can be either defined in relation to the base part, or extracted from features of the base device, or they can be predefined and stored in a separate file linked to the base part file that is imported at the same time as the base part file is imported into the computer program. In another embodiment, the source point positions can be manually controlled/placed via user interaction with the GUI, or they can be parametrically controlled, with the parameters being derived from dimensions of the base part geometry.

Although the source points can be placed by the user via interaction with the GUI, this method is discouraged as there is less control over the customisation process. This may lead to potential differences in the resulting customised device according to which user created the device, which leads to more issues with standardising the customisation approach. Therefore, the approach favoured here is for a predefined set of points to be stored with base part geometry and for these source points to be loaded into the computer program at the same time as the base part file is loaded. If this is not possible, then instructions on how and/or where to the source points for the base part may be stored with the base part and made accessible, such as via a pop up window, when the base part is loaded into the computer program.

The source points are projected using a projection vector until the projected source points intersect the surface of the 3D representation of the (target) patient anatomy. The points of intersection of the projected points with the patient anatomy define the new target point positions.

For cases where parameters, for example linear measurements, are used to create the target point positions, source points are stored with the original base part/device in corresponding positions to where the measurements are taken from the target geometry. These source points are then adjusted so that the distance between the points matches the measurement. These adjusted points are now in the target positions.

The method of the present disclosure aims to maintain precise control on the resulting dimensions and structure of the boundary representation, namely triangulated polygon surfaces, of the warped/customised device. The method maintains the original (base) device design's thickness, in the case of plate customisation, as well as maintaining the 3D vertex number and connectivity between the generic and customised device design, for all customisations. The reason for this is to maintain design features/parameters of the original base device in the resulting customised device, as these features are likely critical to the mechanical performance of the device.

The method also allows for the geometry of certain design features/areas of a device to remain unwarped. Maintaining the original geometry of certain aspects of a device's geometry can be vital for the device to function correctly. For example, in a device designed to be used with screws, for example a locking plate, it is essential that the geometry of the thread for the screws remains unadjusted to ensure that the screw will still work with the threaded hole in the plate. In one arrangement, the method stores lists of points making up the design features that must not be warped with the geometry file, in a similar fashion to the file storing the source points that is stored in conjunction with each device geometry file. In an alternative arrangement, the points of the design feature that must remain unchanged can be selected by the user via interaction with a graphical user interface (GUI) presented to a computing device accessed by the user. Again, the approach in which a separate file is used in conjunction with the geometry file is favoured, as this will result in a more standardised customised result.

Although aspects of the device geometry can be set to remain un-warped, in that their shape is not altered, those aspects will still be rotated and translated according to the rotations and translations applied through the warping process of the neighbouring points. In this way, the device as a whole maintains a continuous geometry.

Figure 5:
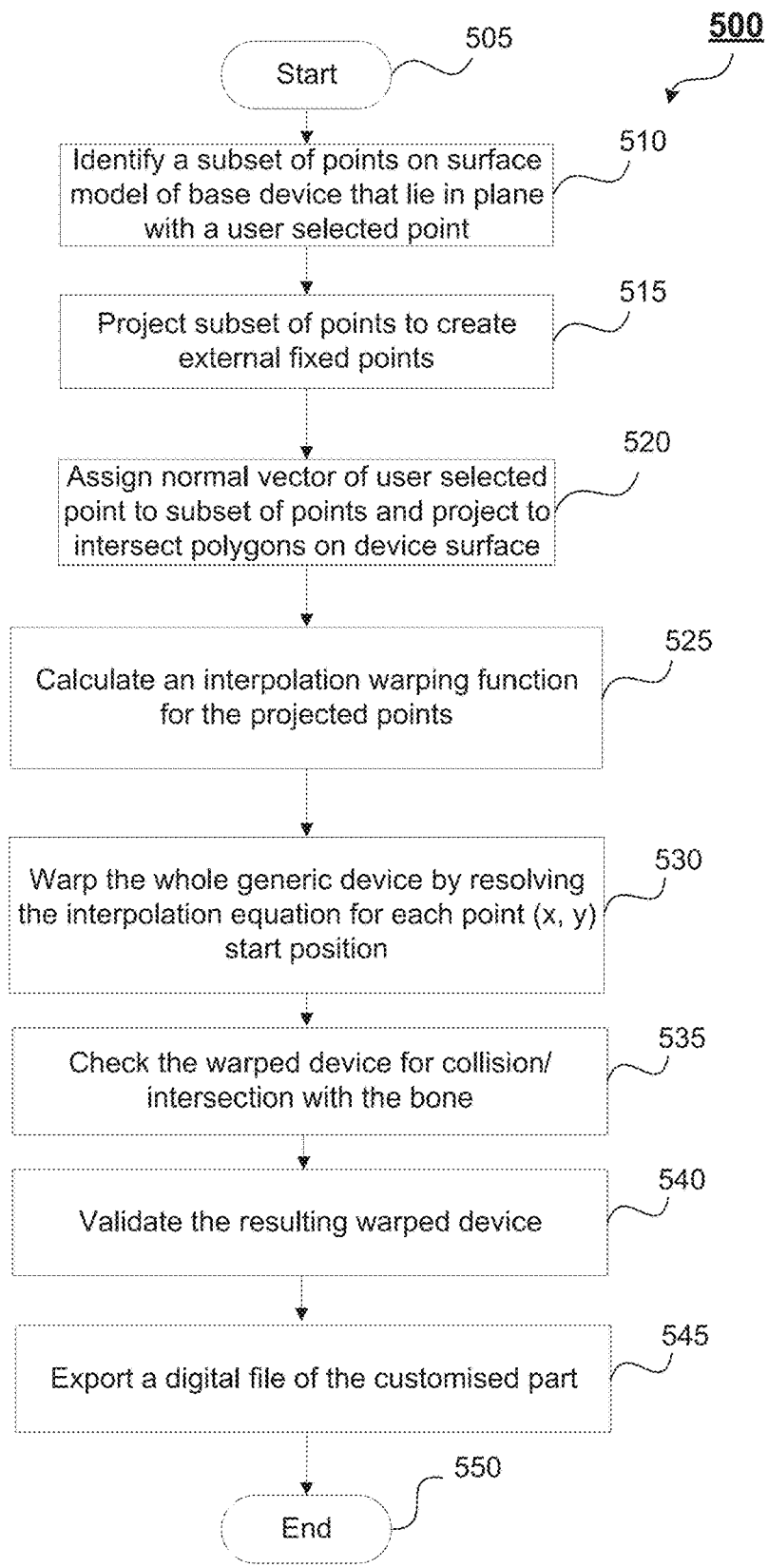
FIG. 5 is a flow diagram 500 of a method for customising a generic surgical plate using warping of a model of that surgical plate.
Figure 6B:
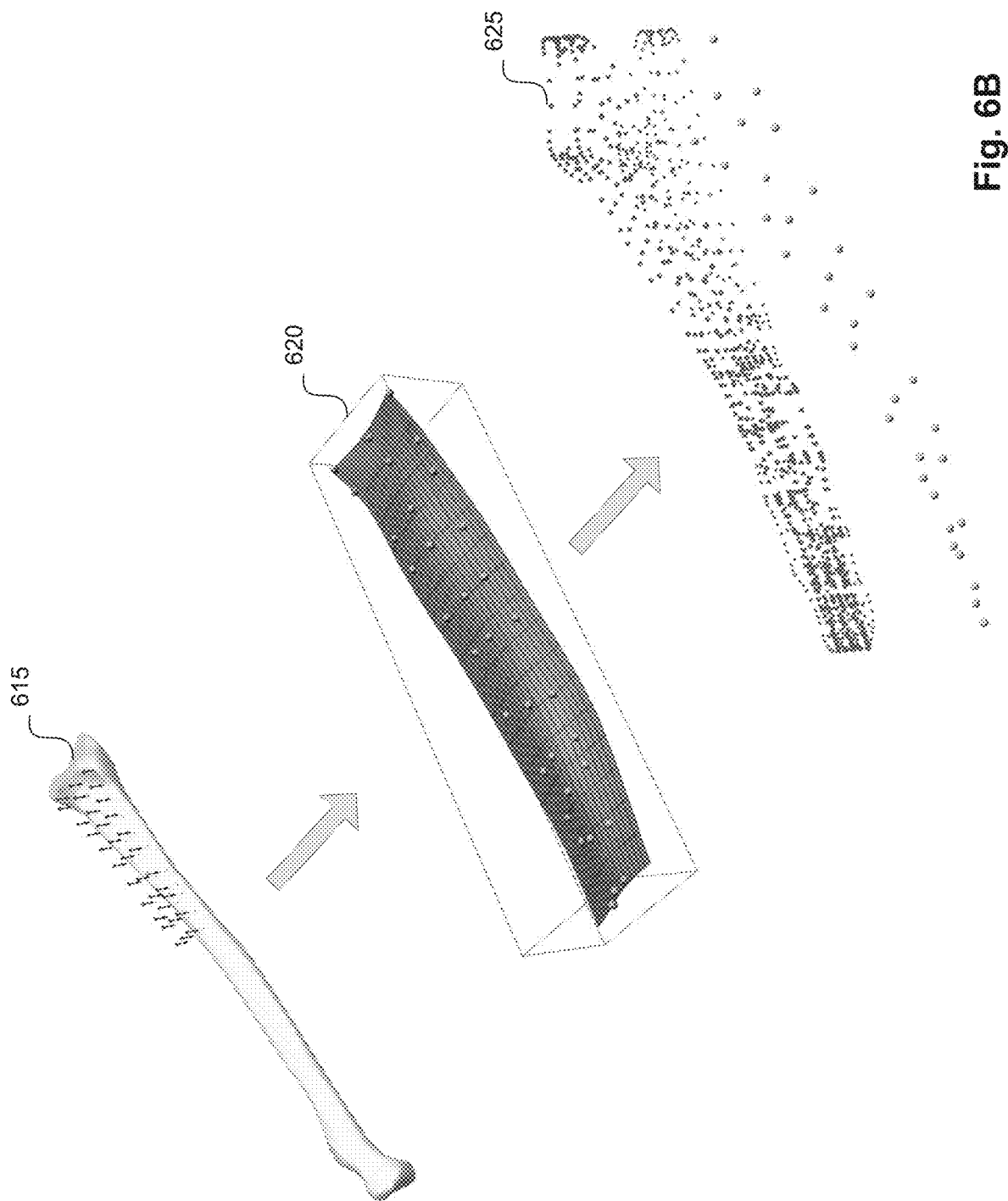

FIG. 5 is a flow diagram illustrating a method 500 for performing core warping of surgical plates and the like. In this example, the method 500 is described with reference to the surgical plate 210 shown in FIGS. 2A and 2B that is to be affixed to a bone. The method 500 begins with a Start step 505 and proceeds to step 510, which identifies a subset of points that lie in a plane with a user-selected point on a surface of the plate that is to contact a bone or loads the predefined points that are stored in connection with the original base device geometry file (also see FIG. 6A, part 605). These points are the source points. In this example, the user selects point (3) (also see FIG. 14E). The source points include points at the extreme dimensions of the device, being the maximum length and width. In step 515, using inertial axes of the device, the source points are projected outwards to form external fixed points outside of a warping area (also see FIG. 6A, part 610). The warping area defines a region within which the warping interpolation function will be largely constrained.

FIG. 6 shows a model 605 of the base device, with the identified source points, which are then projected (away from the plate surface) using the point (3) normal vector 610.

Returning to FIG. 5, control passes to step 520, which assigns the normal vector of the user-selected point (3) on the surface of the device that faces the bone to all of the source points and projects those points (610 in FIG. 6) until those points intersect with polygons on the bone surface. For those vectors that miss the bone, the algorithm assigns the magnitude of their closest neighbour. Intersection of the points with polygons on the bone surface is illustrated in 615 of FIG. 6. These are the target points.

Returning to FIG. 5, step 525 calculates a warping function, shown in this case as a thin plate spline, that warps the original source points to the positions of the target points. This is illustrated as 620 of FIG. 6.

The method then, in step 530, warps the whole generic device by resolving the warping interpolation equation for each point start position of the points making up the original device. This is illustrated as 625 of FIG. 6. Step 535 checks the warped devices for collision/intersection with the bone. The warped model is then adjusted, by translation away from the bone surface, until any collisions have been resolved, shown as 630, 635, and 640 of FIG. 6. Control passes to step 540, which checks the resulting warped device to ensure that all triangles are valid and to prompt the user to confirm that the result is satisfactory. The user can check the warped device for shape, distance from bone, amount and regions of contact between the device and bone, and the like. Control then passes to step 545, which exports an output file of the warped device. Control passes to an End step 550 and the method 500 terminates.

Figure 6C:
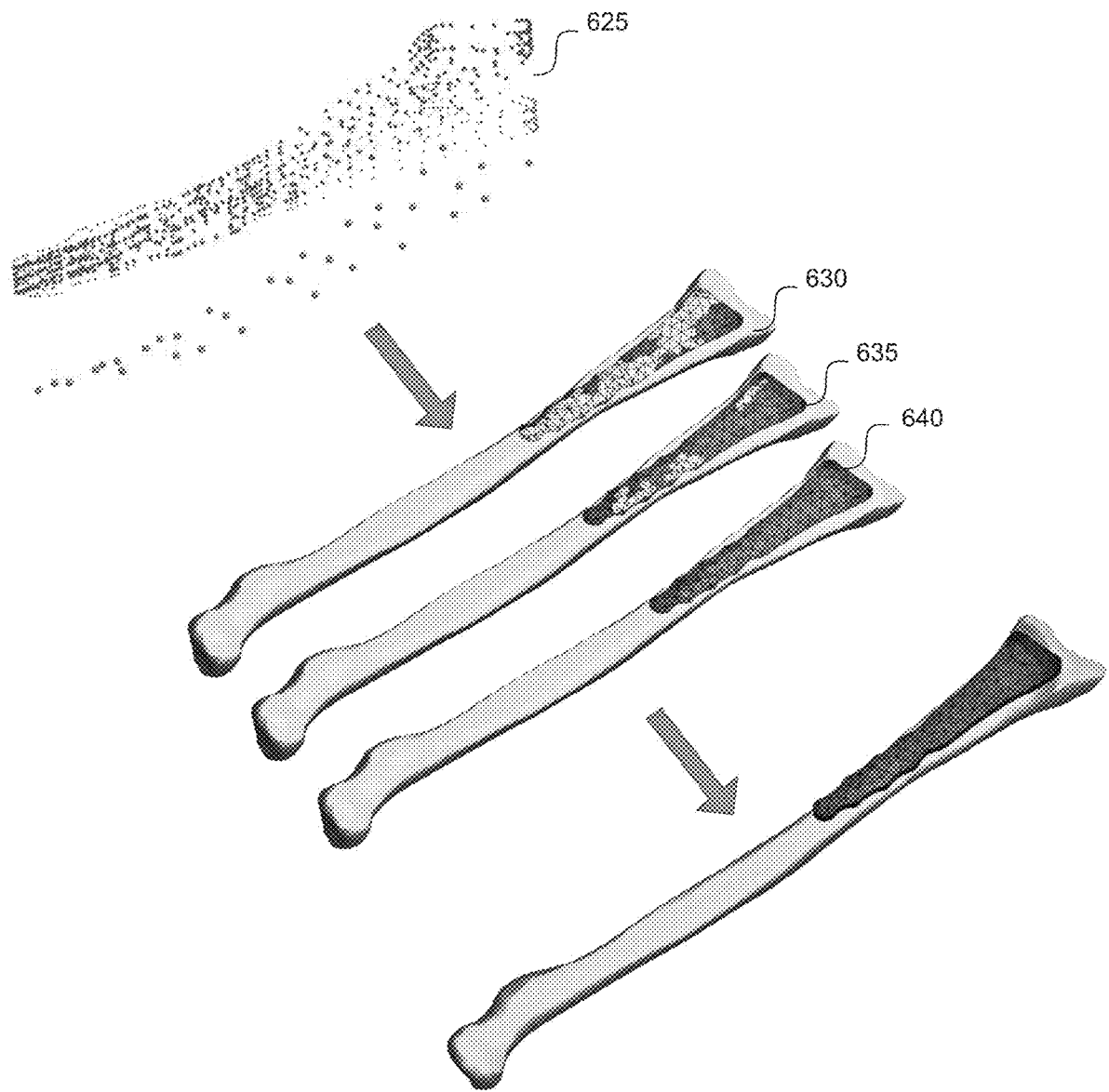
Figure 7:
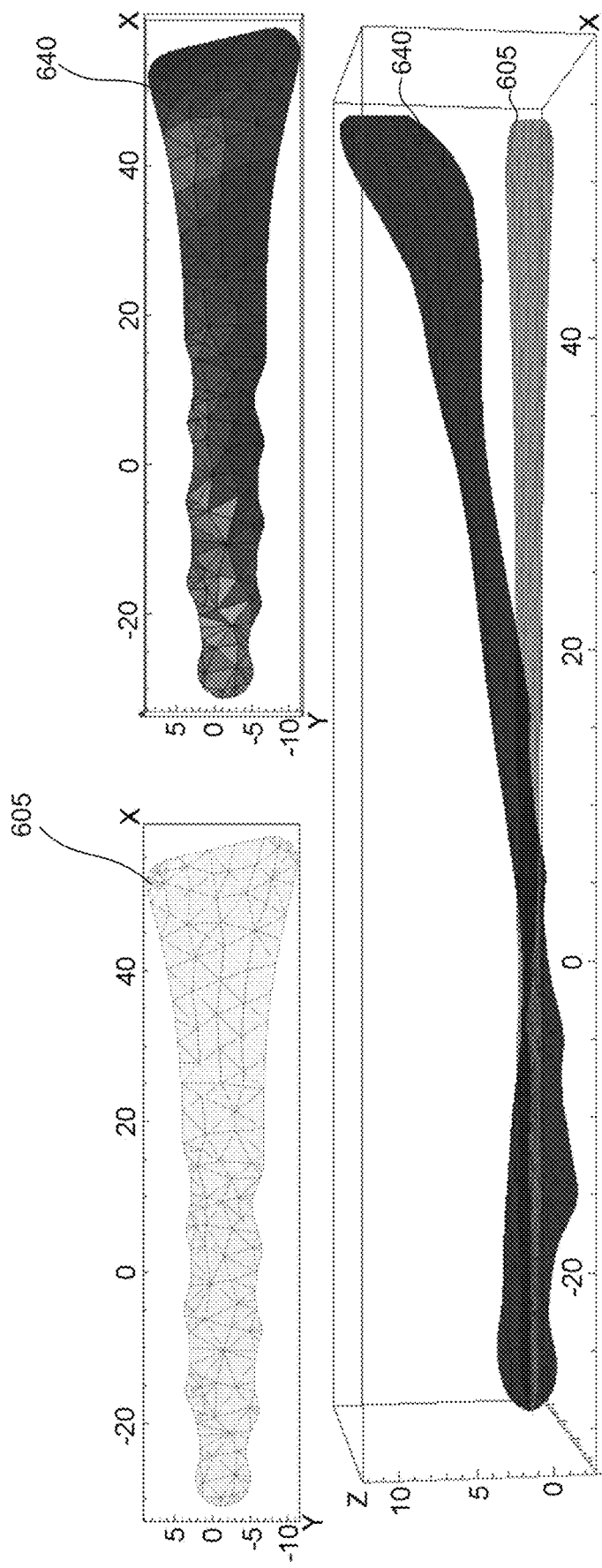
FIG. 7 shows one surface of the original base plate of FIG. 6A overlayed with the customised surface that results from the warping process of FIGS. 5 and 6A to 6C.

FIG. 7 shows, for illustration purposes only, one surface of the original plate 605 overlayed with the customised plate surface 640 that results from the warping process described above with reference to FIGS. 5 and 6. It is evident that the flat structure of the original base plate surface 605 has been warped to produce the customised plate surface 640 that is better able to match the surface of the bone to which the plate 640 is to be attached.

Figure 8:
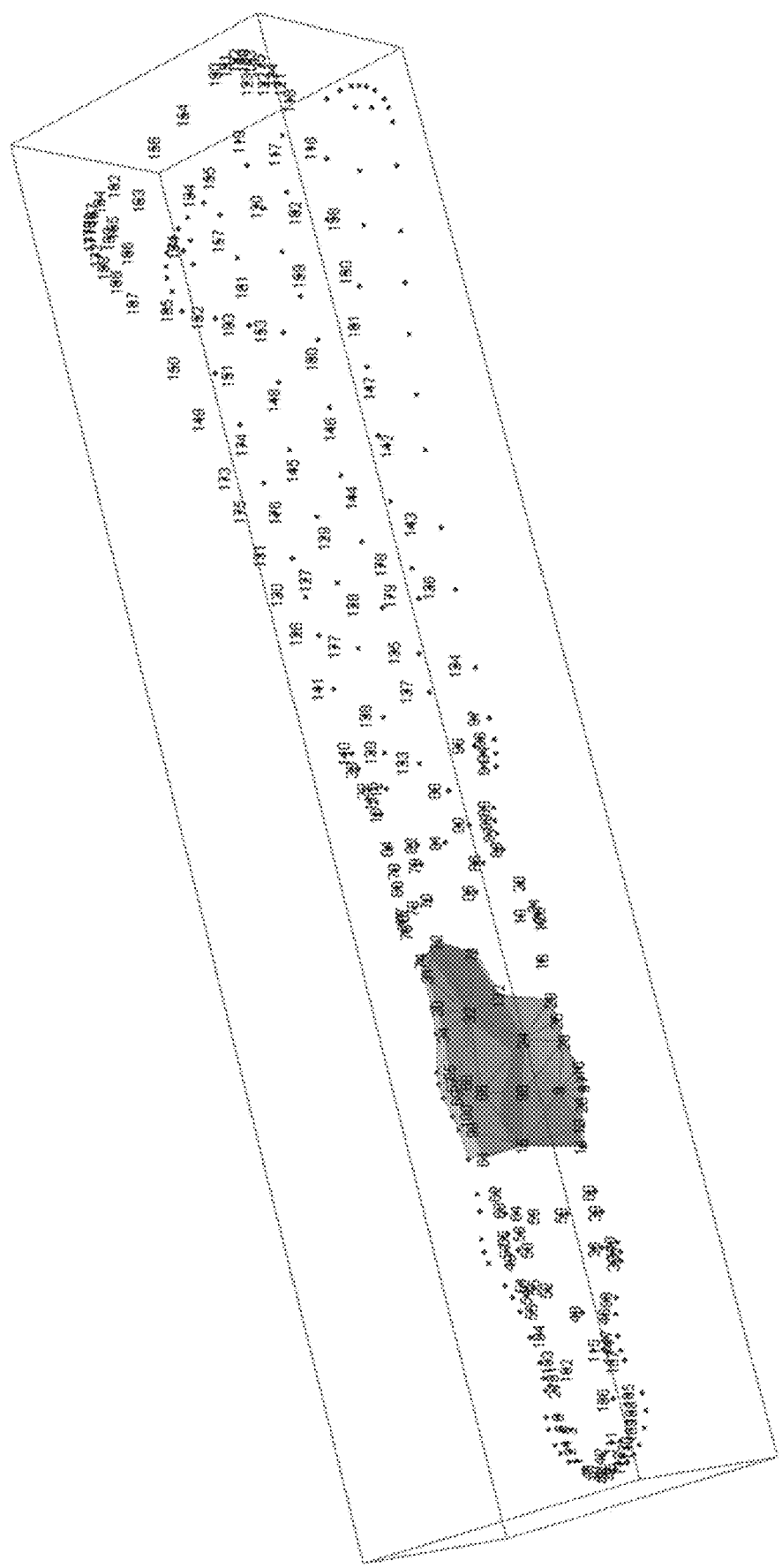
FIG. 8 illustrates the warped surface points (numbered) from FIG. 7 overlaid on the corresponding original surface points.

FIG. 8 illustrates the warped surface points from FIG. 6 overlaid on the corresponding original surface points. FIG. 8 also shows a subset of triangles in the original plate surface and the warped plate surface.

Figure 9:
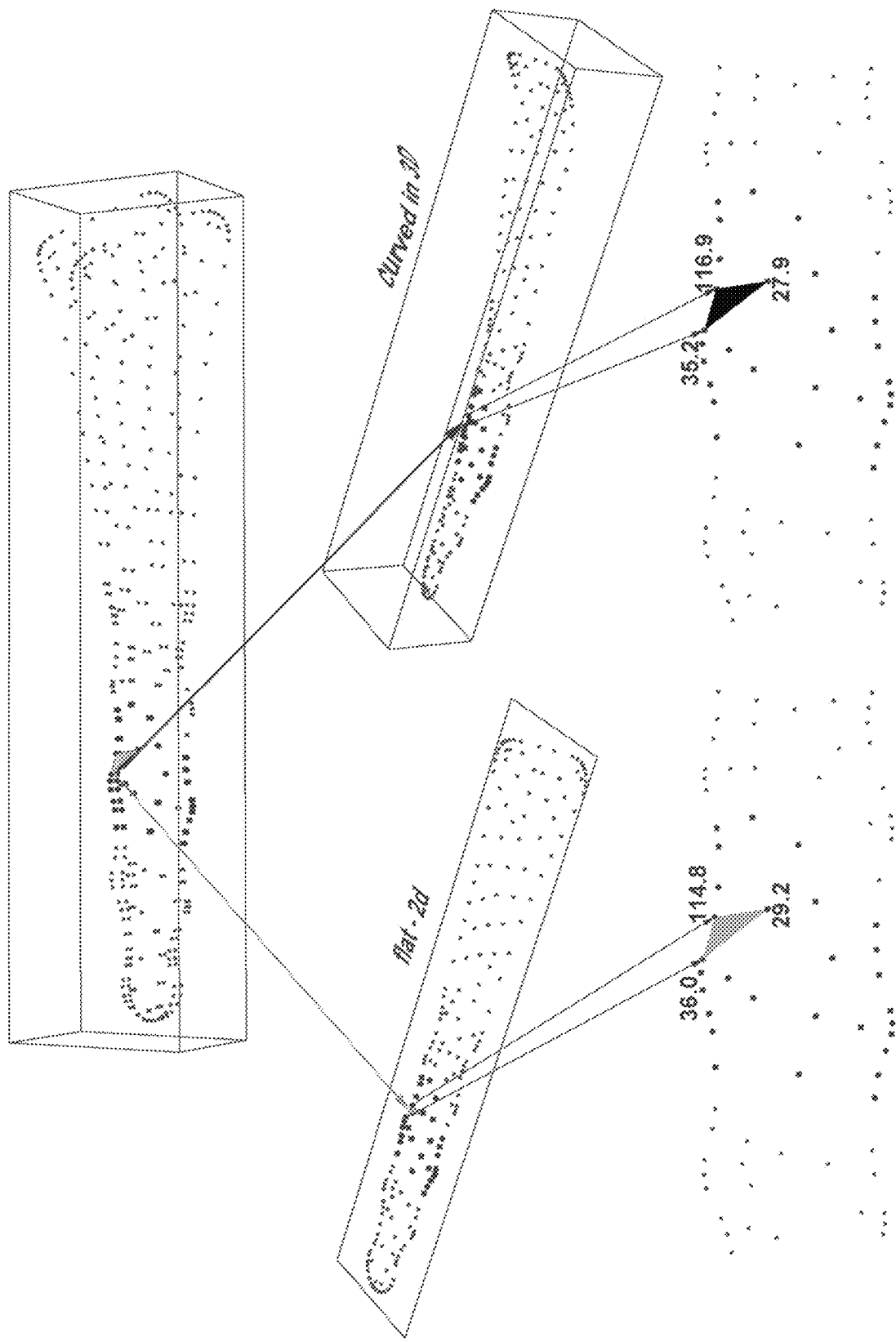
FIG. 9 illustrates a mapping of points from the generic plate to the customised plate showing that subtle variations in the angles of the triangle corners lead to an overall difference in shape between generic and customised device.

FIG. 9 illustrates a mapping of points from the base plate 605 to the customised plate 640. FIG. 9 illustrates that the difference in shape between the original base and warped plate/surface geometry is the result of slight differences in the angles in the corners of the triangular polygons (triangles) of the warped part compared to the original base part.

Figure 10:
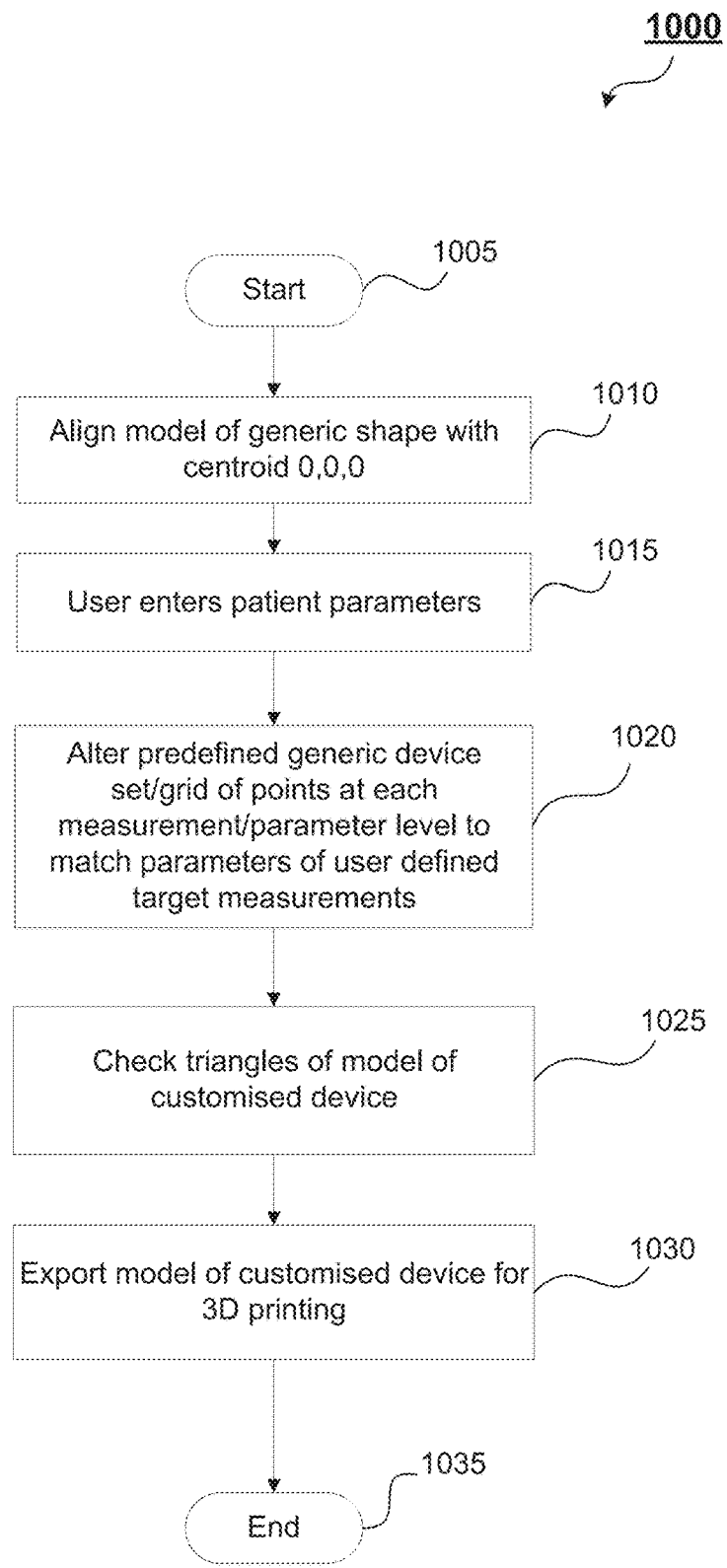
FIG. 10 is a flow diagram illustrating a method for customising a generic device based on patient parameters derived from a patient.

FIG. 10 is a flow diagram illustrating a method 1000 for customising a base device based on patient parameters derived from a patient. Such patient parameters may relate, for example, to measurements of a patient from a scan, x-ray, callipers, or other measurement device. The method 1000 may be applied, for example, to customising splints, orthotics, braces, and other devices.

The method 1000 begins at a Start step 1005 and proceeds to step 1010 in which a model of a base device is (automatically) translated and rotated to be aligned with the device's centroid at global x,y,z=0,0,0, and with the length, width and depth of the device aligned with the x,y,z global axes. This is different from aligning, for example, the centroids of two parts, or the centroid of a base part with the centroid of a region of a target shape, for example a bone. The alignment presented here is an alignment with respect to the global coordinate system, rather than a rigid registration alignment of an original base part with a target geometry, such as anatomy. Frequently such alignment of parts with anatomy are achieved using iterative registration processes, such as the iterative closest, or corresponding, point methods or variations thereof, which are not used to achieve the alignment described in the current method.

Control passes to step 1015, in which the user enters a set of patient parameters. Control then passes to step 1020, which alters a predefined base device design set, which can be in a grid structure, of points at each measurement/parameter level to match parameters of the user defined target measurements. In one arrangement, the set/grid of points is either predefined and stored with the generic/original device geometry in a database or computer memory (e.g., 325, 360, 370, 344 in FIG. 3), or the set/grid of points can be defined by user interaction via the graphical user interface (GUI) of the software. In this case, the user defines where measurements on the patient representation (photo, 3D representation, planar x-ray) were made, either by manually picking the points where the measurements were taken, or by using an on screen slider to move predefined grid lines into the correct position. These points are used to project a grid (for Radial Basis Interpolation) in 3D at the user defined measurement points.

A following step 1025 then checks the triangles and general viability of the model for 3D printing, before step 1030 exports a model of the customised device, such as a .stl file, for 3D printing or other computer aided manufacturing process. Control passes to an END step 1035 and the method terminates.

Figure 11A:
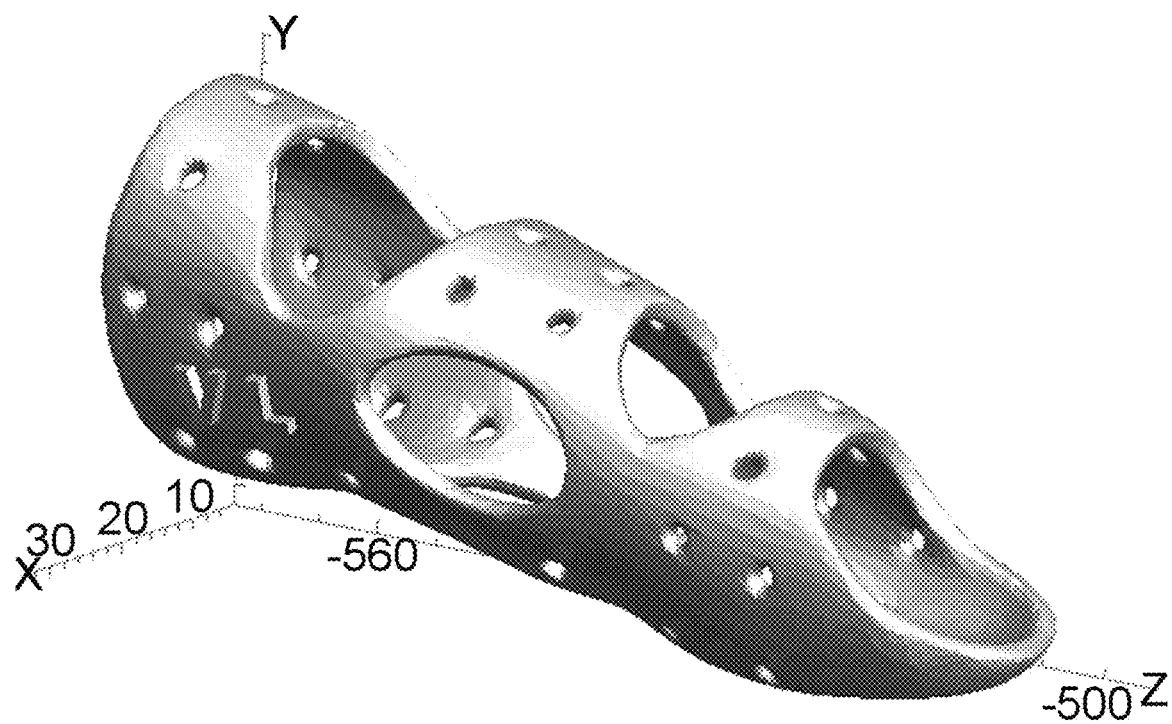
FIGS. 11A to 11G illustrate the application of the method of FIG. 10 to customising a finger splint.
Figure 11A:
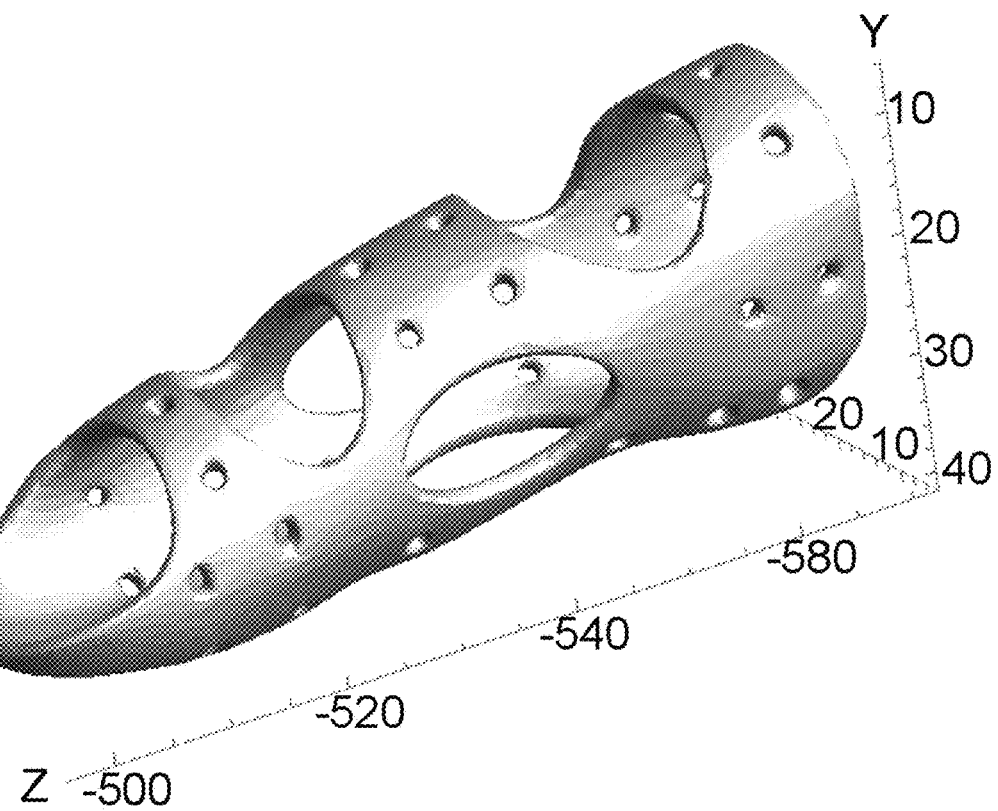
Figure 11B:
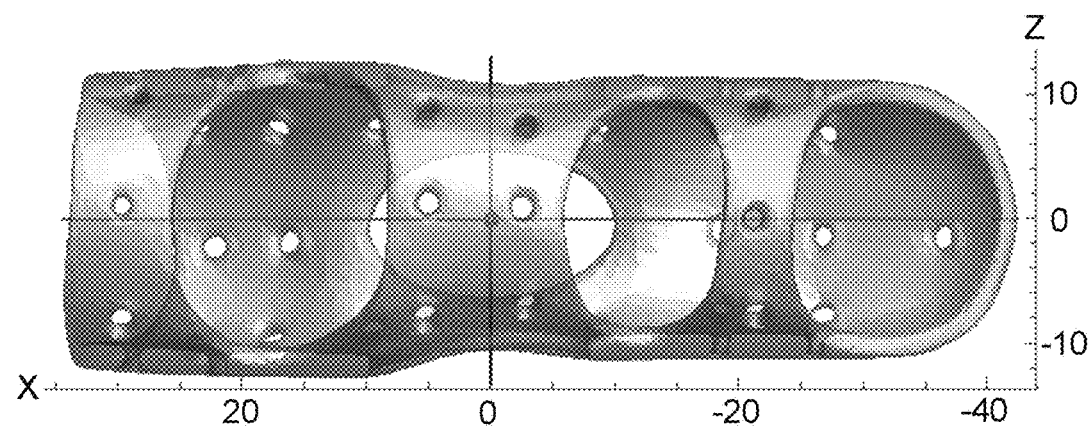
Figure 11B:
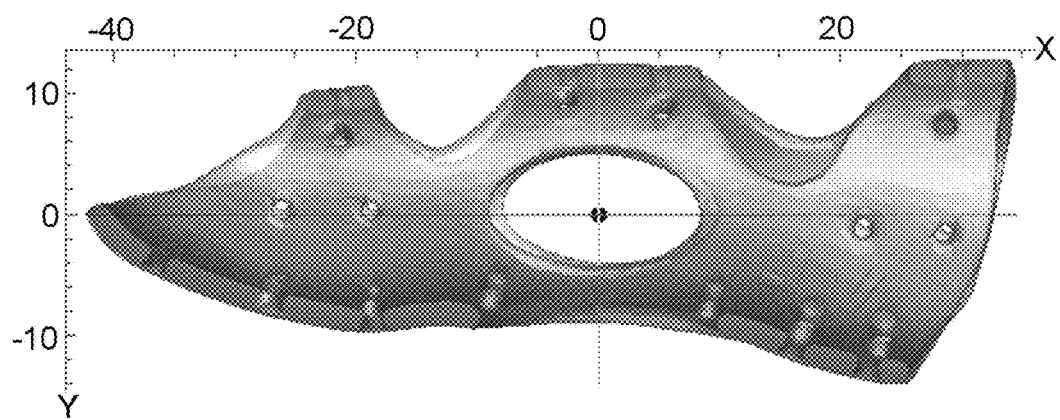

FIGS. 11A to 11G illustrate the application of the method of FIG. 10 to customising a finger splint. FIGS. 11A and 11B show a base model of a generic finger splint that has been rotated and translated from a random place within a global coordinate system so that a centroid of the base model is located at x,y,z 0,0,0, with length positioned along the x-axis, width along the y-axis, and depth along the z-axis.

Figure 11C:
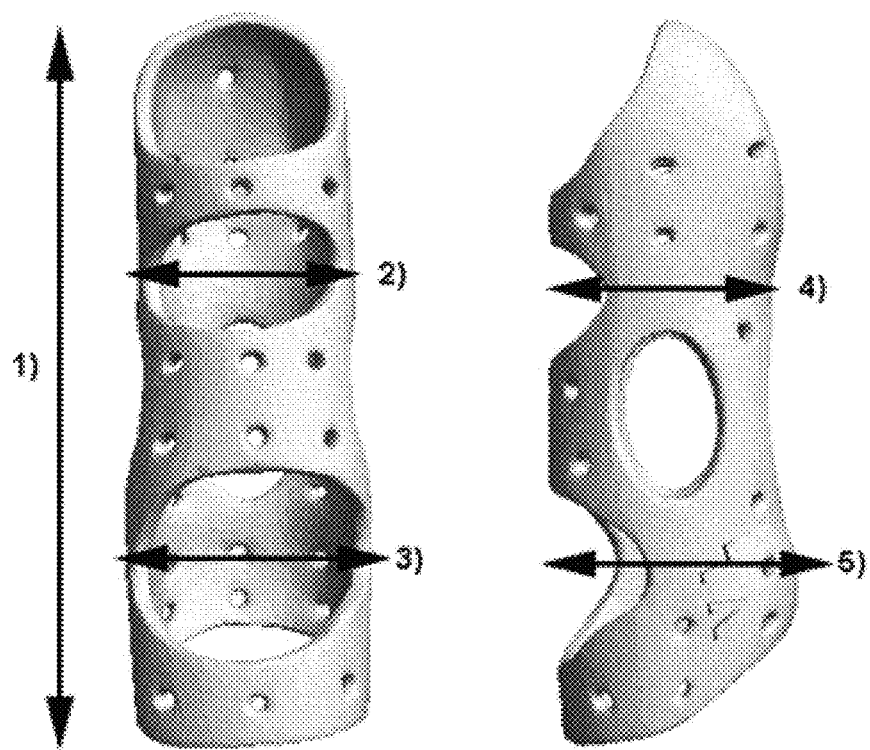
Figure 11D:
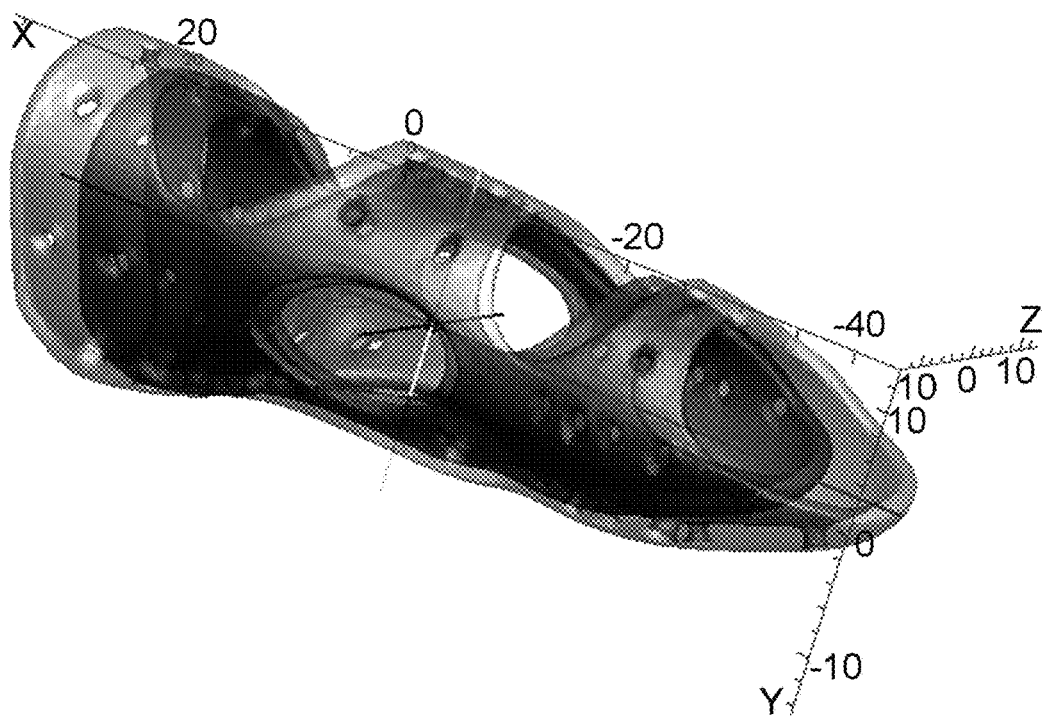

FIG. 11C shows points at which measurements are taken in relation to a patient to which the splint is to be fitted. In this example, the measurements relate to: (1) length of the finger, from fingertip to mid-way between knuckle 2 and knuckle 3; (2) width of knuckle 1; (3) width of knuckle 2; (4) height at knuckle 1; and (5) height at knuckle 2. FIG. 11D shows an affine warp according to the measurements obtained in relation to FIG. 11C.

Figure 11E:
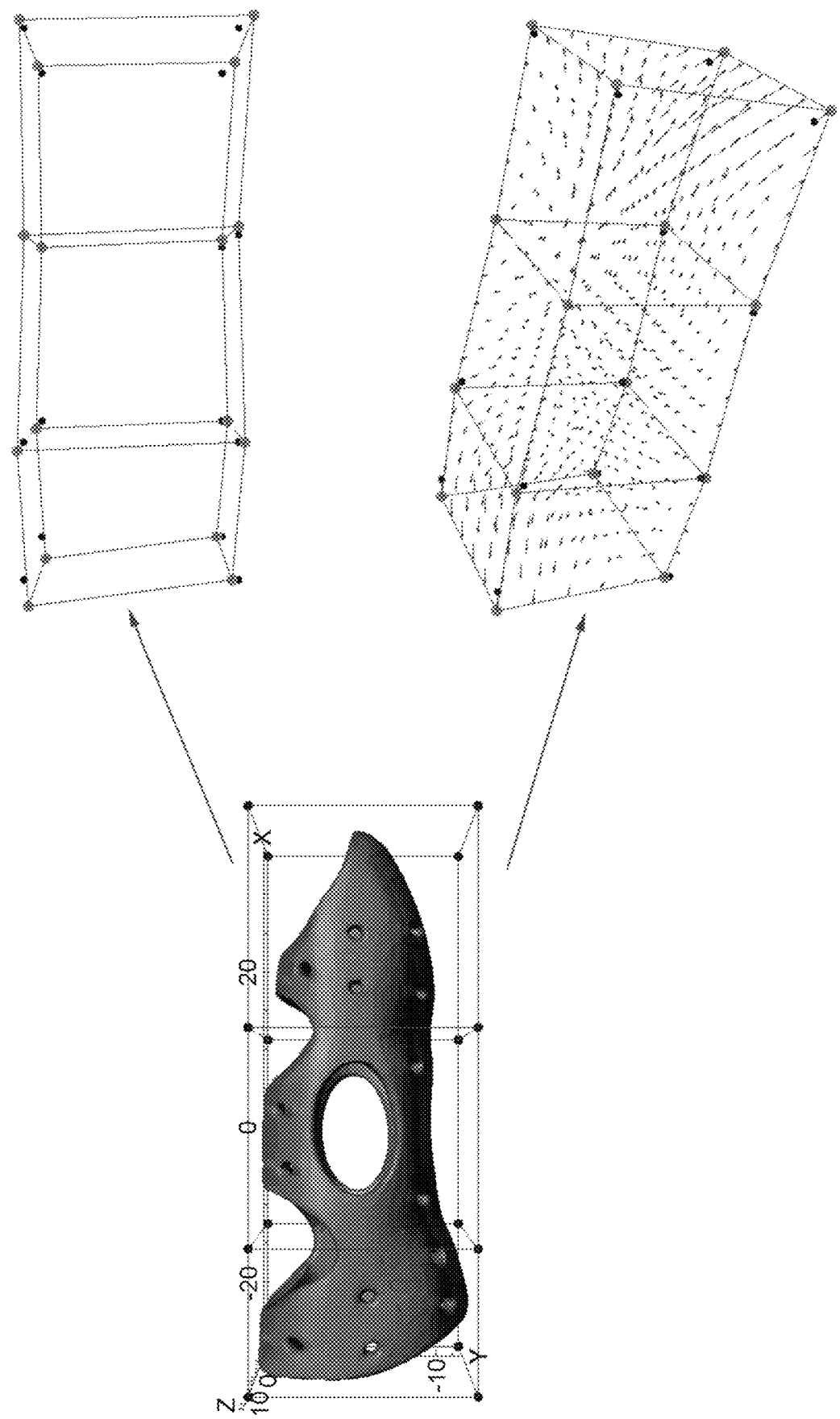
Figure 11F:
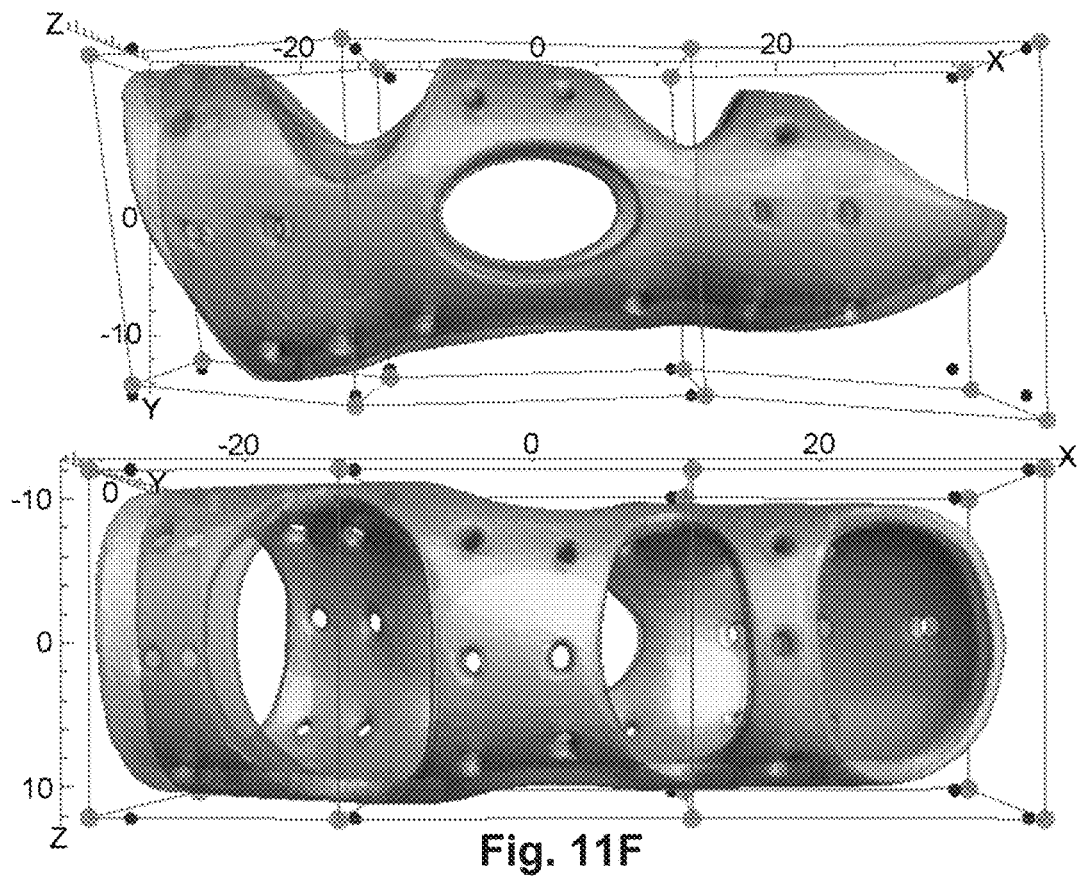
Figure 11G:
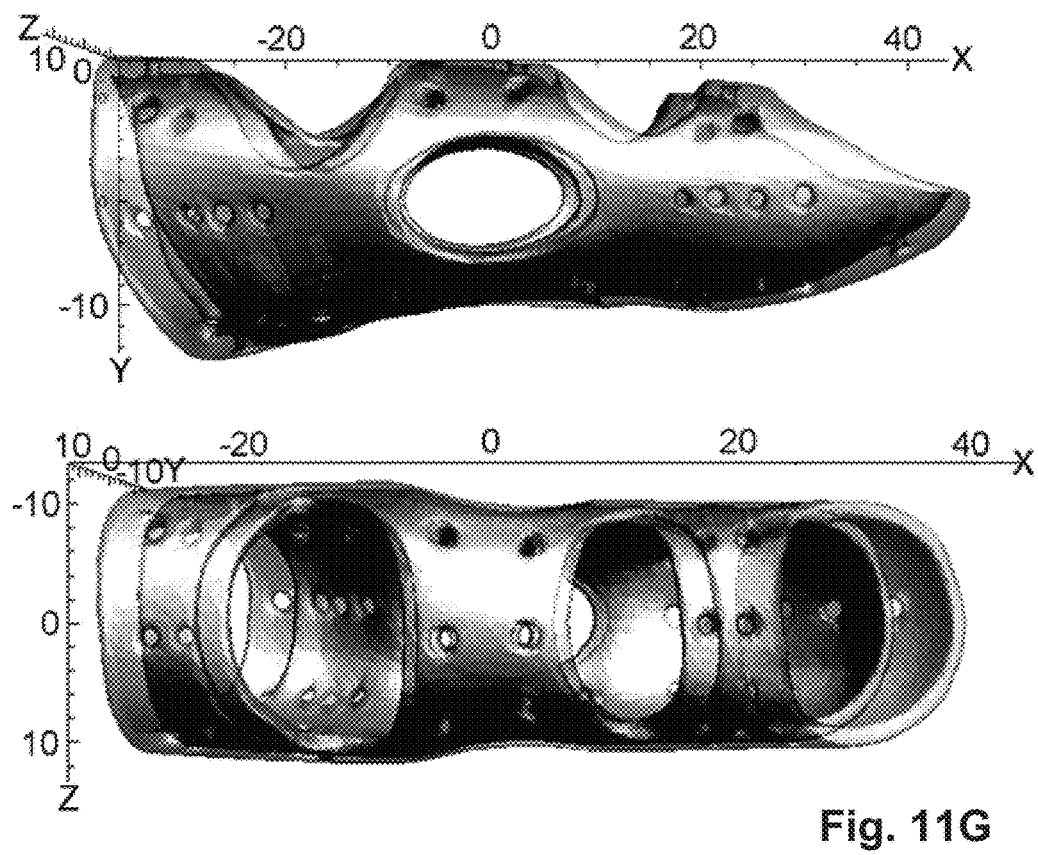

FIG. 11E illustrates establishment of a grid that is based on the patient measurements/parameters. The grid is altered so that dimensions of the grid (including tolerances) match those of the patient parameters. Further, a warping interpolation function is calculated to achieve the parametric changes, represented by the vector field in the lower right of FIG. 11E. FIG. 11F shows application of the warping interpolation function to the affine adjusted device to achieve a final, customised device. The final device is shown in FIG. 11G. It is to be noted that the final device maintains the structure of the base device, but has a customised, patient-specific geometry.

Figure 15:
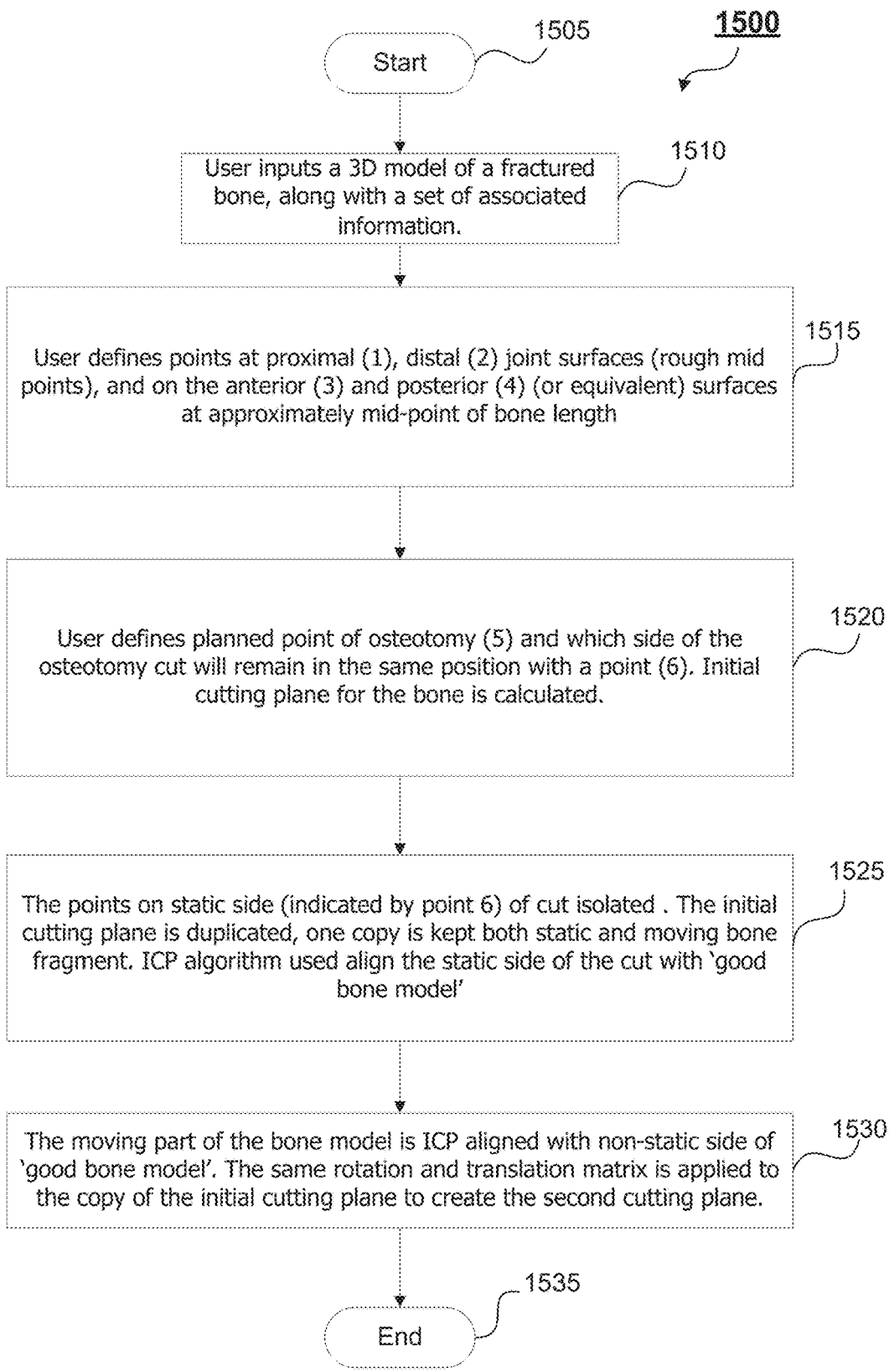
FIG. 15 is a flow diagram illustrating a method relating to fracture and/or osteotomy cases.

FIG. 15 is a flow diagram illustrating a method 1500 relating to fracture and/or osteotomy cases. The method 1500 begins at a Start step 1505 and proceeds to step 1510, in which a user inputs a 3D model of a fractured bone, along with a set of associated information. The associated information may include, for example, a name of the bone, age and sex of the patient, and whether the bone is from the left or right hand side of the skeleton of the patient.

Control passes to step 1515, in which the user defines points at proximal (1), distal (2) joint surfaces (rough mid points), and on the anterior (3) and posterior (4) (or equivalent) surfaces at approximately mid-point of bone length. In a following step 1520, the user defines a planned point of osteotomy (5) and which side of the osteotomy cut will remain in the same position with a point (6). An initial cutting plane for the bone is calculated.

Step 1525 isolates points on a static side of the cut (point 6). The initial cutting plane is duplicated, with one copy kept for each of the static and moving bone fragments. An Iterative Closest Point algorithm (ICP) algorithm is used to align the static sign of the cut with a model of a "good bone". The rotation and translation achieved from the ICP algorithm is applied to the moving bone fragment.

In step 1530, the moving part of the bone model is ICP aligned with the non-static side of the "good bone model". The same rotation and translation matrix is applied to the copy of the initial cutting plane to create a second cutting plane. Control passes to an End step 1535 and the method 1500 terminates.

There are many different ways to create the "good bone model" referred to in relation to the method 1500 of FIG. 15. One approach is to use "good anatomy" on the opposite side of the patient's body. Thus, if a patient has fractured the right ulna, use the un-fractured left ulna to create a model of a good bone model for the right ulna. A CT scan can be used to create an initial model of the left ulna, which can then be mirrored across the sagittal midline of the body (or equivalent plane) and then ICP superimposed on the fixed (proximal) bone fragment. The moving (distal) fragment of the 'broken' bone can then be aligned to the distal part of this mirrored good anatomy.

In a scenario in which a CT scan of the broken bone only is available, it is possible to use a model from a stored atlas of bones. "Atlas" bone models provide average bone shape models for a particular size, body mass, age, and sex. Thus, based on the particulars of the patient, an atlas bone is selected that can then be warped using an affine (length, depth, and width), radial basis, as rigid as possible or other warp function to match that of the broken bone anatomy. For very bad breaks, the length can be estimated by the addition of the fragment lengths. The warped atlas bone can then be ICP aligned with the static (proximal) bone fragment, with the distal part of the warped atlas model acting as the guide for the remaining fragment(s) of bone.

Where digital planar x-rays of the broken anatomy only are available: measurements can be taken from the x-ray (estimates of lengths, widths and depths) for the bone (taking into account the distortion/magnification factor of x-ray source—sensor, this information is included in the digital copy of the x-ray) and be used to construct an affine, radial basis, as rigid as possible or other warp function for an "atlas" bone. The surface of the warped atlas bone can be used directly to drive the planning and warp of a customised cutting and/or drilling jig and the warp of generic device to the customised shape.

An alternative method using a 3D reconstruction of the pathological anatomy only is to either take landmarks by hand from the good region of the anatomy, or to ICP fit the good region to an atlas bone and then use a known (calculated as proportion of the normal points depending on the proportion of the anatomy affected by the trauma/pathology) subset of the points of this good region to create a novel eigenshape space of the specimens in the anatomical database. The eigenscore of the patient's bone within this shape space can then be used to create a whole eigenshape bone that would closely match the good part of the patient's anatomy and act as a guide for the positioning of the remaining fragment(s) of bone.

DESCRIPTION OF EMBODIMENTS

Various embodiments of the present disclosure will now be described. The CAD work flow starts with the following user interactions.

1) The user defines what type of procedure is being modelled. In this example, the following set of procedures is available for selection by the user:
   a. Fracture fixation by plate with no re-alignment of bone fragments;
   b. Fracture fixation by plate with re-alignment of bone fragments;
   c. Fracture fixation by Inter-medullary (IM) nail with no re-alignment of bone fragments;

d. Fracture fixation by Inter-medullary (IM) nail with re-alignment of bone fragments;
e. Single joint re-surfacing;
f. Total joint arthroplasty;
g. External splint, support or orthotic;
h. Cervical plate;
i. Inter body cage, for vertebral body fusion;
j. Plate with flange; and
k. True 3D custom.
2) The user imports into the software a 3D reconstruction of the pathological body part. This reconstruction is obtained through greyscale thresholding DICOM data (usually CT or MRI) to produce a boundary representation isosurface of the body part.
3) The user imports into the software the parametric or isosurface (triangulated vertices) representation of the base device to be customised and the device's associated predefined points for projection (if applicable).

Cervical Spinal Inter-Vertebral Body Fusion Devices

For cases of chronic vertebral disc degeneration, where the vertebral disc height is reduced, pressure can be put on the nerve roots exiting the spinal cord at this level. This pressure can lead to numbness, tingling in the tissues where the nerves end and/or localised pain around the spine.

One method for alleviating symptoms, and preventing the issue from occurring again, is to perform an inter-vertebral body fusion. In this procedure, the diseased disc between the two vertebral bodies is partially/completely removed, the level is distracted (the disc height is restored) and the two opposing vertebral bodies are fused. Options for orthopaedic devices to facilitate fusion include posterior rods and screws, an anterior plate, and inter-vertebral body cage (or spacer). Frequently, combinations of these devices are used.

The examples below relate to customisation of generic orthopaedic devices that are commonly used to achieve cervical (neck) spine fusions. The orthopaedic devices are an anterior cervical plate and an inter-vertebral body cage. These devices are commonly used in conjunction with one another. However, fusion is not always achieved.

The examples below use two different implementations of the methods set out in the present disclosure to achieve different objectives. The cervical plate is customised to parameters (measures) using a warping interpolation function (a thin plate spline in this instance). Whereas the inter body cage is customised for the specific morphology of the patient using an as rigid as possible warping function.

Cervical Plate

Figure 12A:
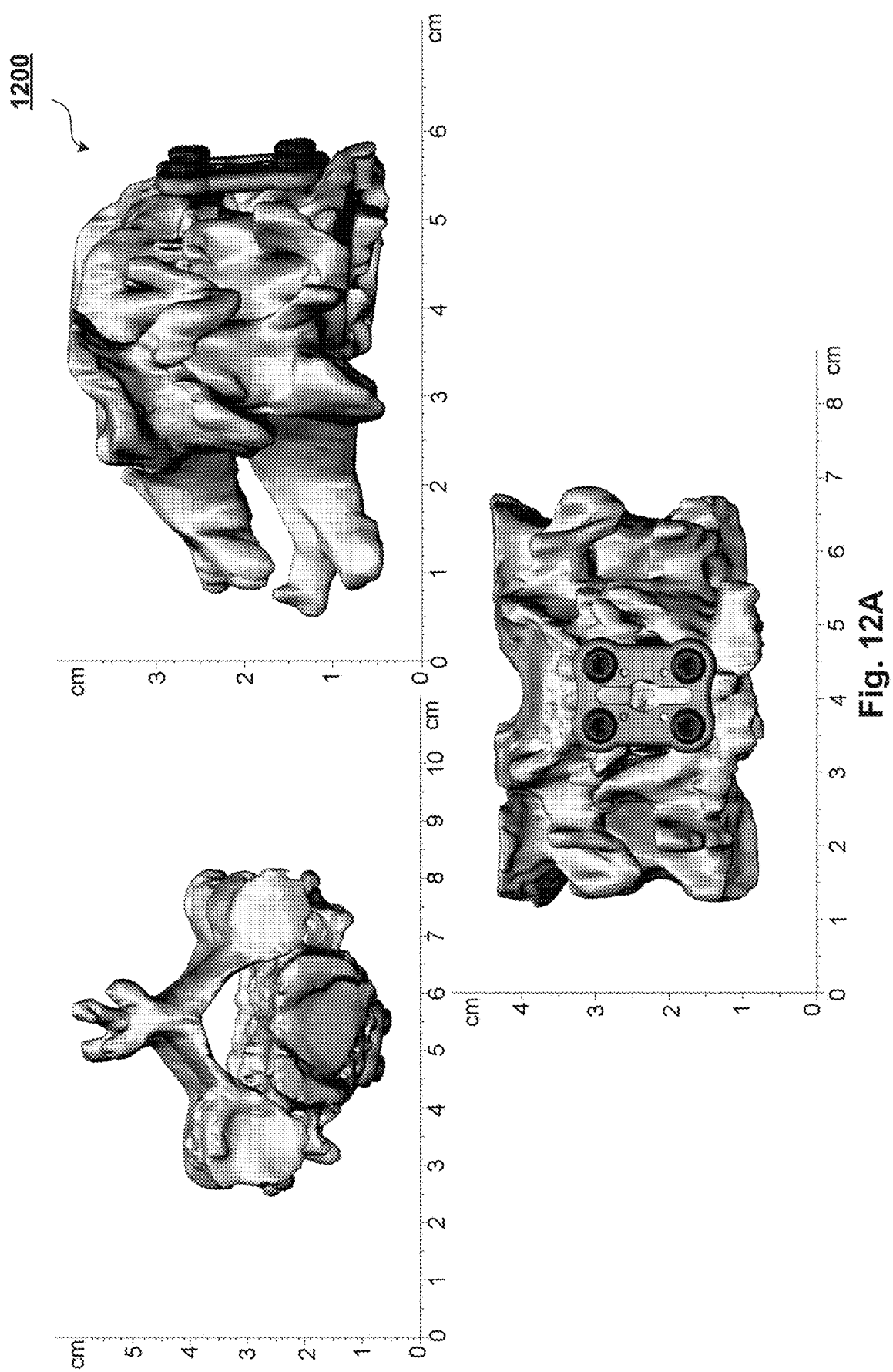
FIGS. 12A to 12H illustrate generation of a customised anterior cervical plate used to stabilise two cervical vertebrae.

FIGS. 12A to 12H illustrate application of the method to an anterior cervical plate used to stabilise, and with the intention of fusing, two cervical vertebrae. In such cases, a loss in disc height can lead to a pinching of the nerves exiting the spinal canal laterally via the foramina. Anterior plates, such as those shown in FIG. 12A attached to vertebrae, can help stabilise the degenerative level, restore disc height, and widen nerve exists. Anterior cervical plates are frequently attached to the vertebral bodies, and held in position, by screws, as shown in FIG. 12A. These screws pass through the cortical bone (outer shell) of the vertebral bodies and into the cancellous, or spongy, bone inside the vertebral body.

In many patients with degenerative vertebral discs, boney degeneration also occurs. This includes the formation of bone spurs (apparent in FIG. 12A), as well as loss of bone density and mineral content in some areas of the vertebra. Loss of highly mineralised, good quality bone is often observed in the vertebral bodies of degenerative spines, particularly in elderly and osteoporotic patients. Poor quality bone inside the vertebral body can pose a problem for the efficacy and longevity of plate attachment as the screws can work loose within the poor quality cancellous (spongey) bone. This process can be accelerated by poor plate placement, poor plate fit, or poor plate design.

The anterior cervical plate shown in FIG. 12A is flat by design. A flat plate can accelerate the micro motion in the screws, that lead to the screws eventually loosening and the plate loosing efficacy, as the plate is held further away from the vertebral body laterally than it is medially. This can increase the effective lever arm exerted on the screws by the plate, causing the screws to work loose more rapidly than if the lateral aspects of the plate were closer to the cortical surface of the vertebral bodies.

Further, if, during implantation, the surgeon uses the screws to 'pull' the plate into contact with the cortical bone of the vertebral body, then residual strain energy will be stored in the plate. This strain energy is transferred to the screws in the form of a 'pull out' force, causing the screws to back out of the vertebral body and the plate to lose its stabilising function.

Therefore, maintaining close proximity of the lateral aspects of the plate to an anterior surface of the vertebral body is desirable to minimise potential moment arms and pull out forces. As the anterior aspects of the vertebral bodies are curved, a curved plate could have advantages over a straight plate. Even more advantageous would be a plate with two curves: a lateral (width way) curve to accommodate the curvature of the vertebral body and a second superior-inferior (long ways) curve to accommodate the (remaining) disc and/or boney rim to the vertebral body endplate. These curves can be measured from either an individual patient, or average values could be obtained from an anatomical study and/or database.

Much time and effort may have gone into the design history and design master file of the plate. The method of the present disclosure is adapted to modify and update the existing base design of the straight plate to encompass two curves of different radii, whilst retaining all of the design features of the original plate (the base part).

The following example shows how this can be achieved using the method described in the present document. Although the specific example given is for the modification of a cervical plate, it should be noted that this aspect of the method disclosed herein could be used to introduce curves to any designed part, including those outside of the medical device industry, such as those used in automobile, aeronautical, consumer goods, jewellery, orthotic, clothing and protective clothing/equipment, and other industries.

Figure 12B:
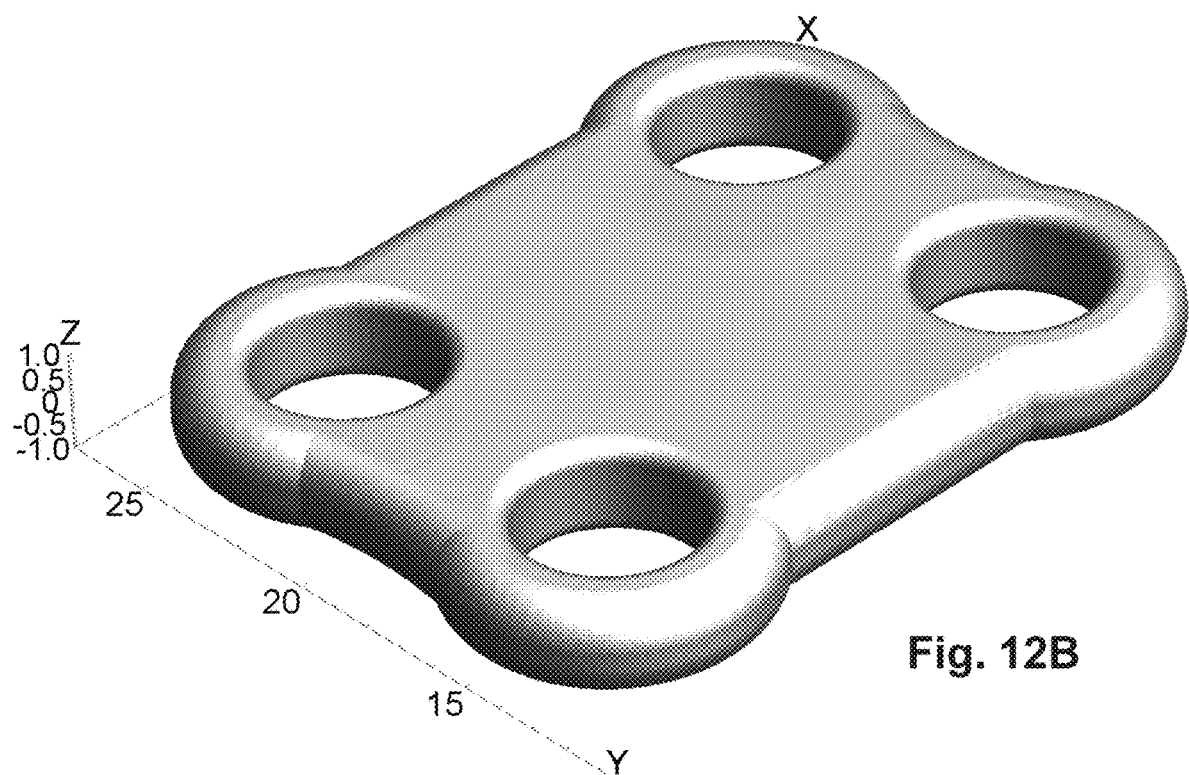

FIG. 12B shows a simplified generic base flat cervical plate design, relative to the plate shown in FIG. 12A.

Figure 12C:
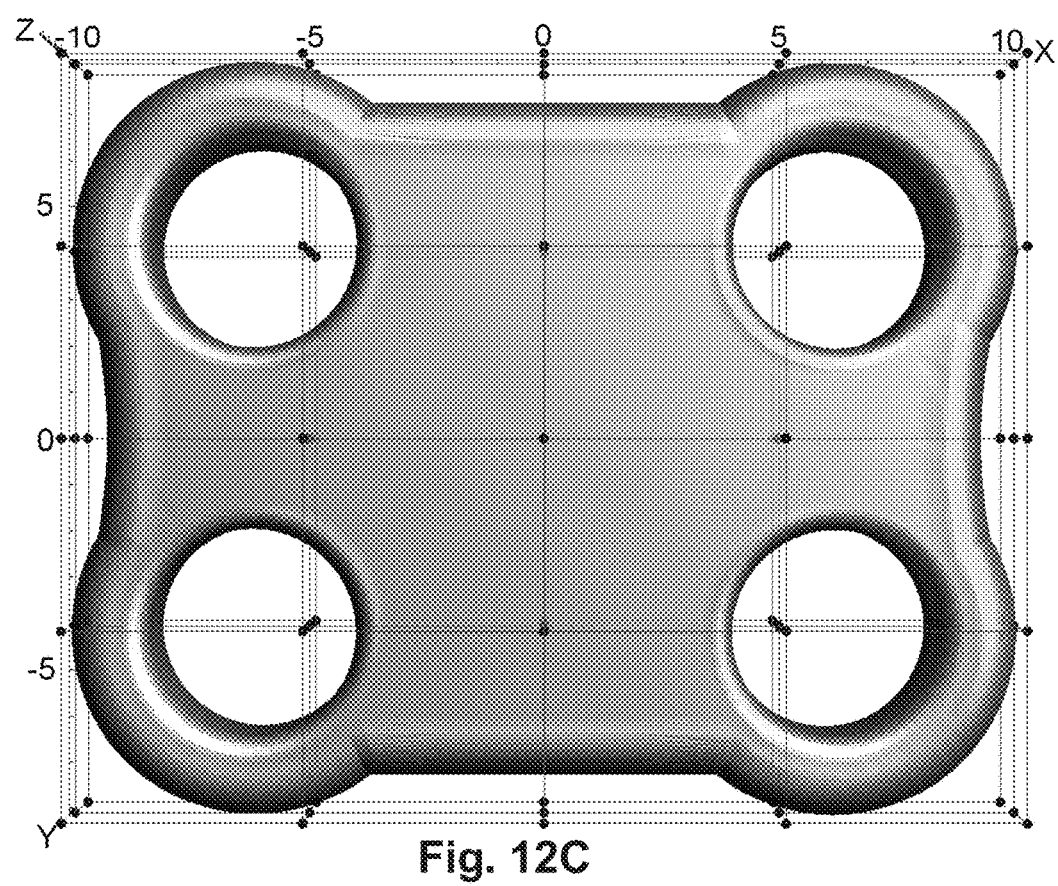

FIG. 12C shows the plate of FIG. 12B, with an accompanying grid of points. This grid of points is generated by using the maximum and minimum x,y,z coordinates of the device once the device has been aligned with the global coordinate system. A user can then specify how many rows of points should be used in all three axes. In the case shown in FIG. 12C, there are five rows/columns used for both x and y axes, with three being used for the z axis.

Figure 12D:
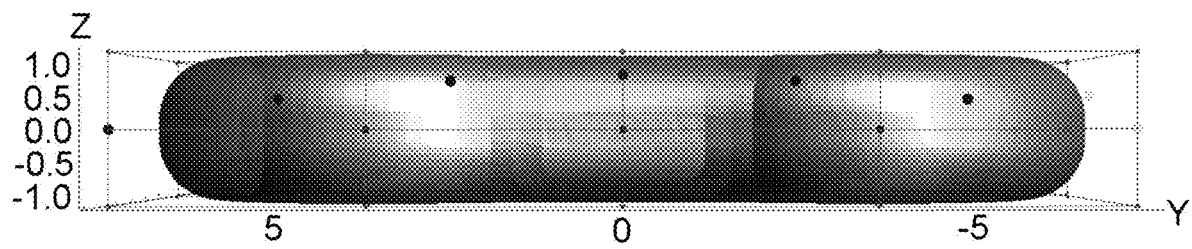
Figure 12E:
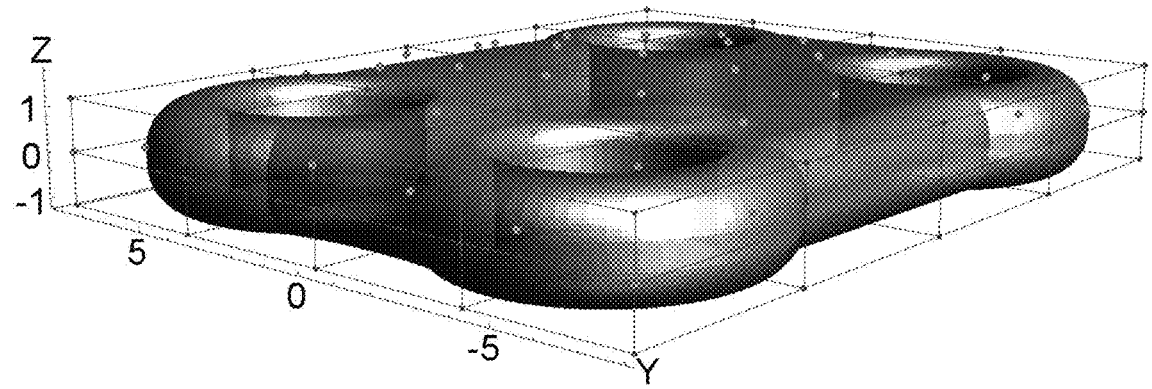

The user then specifies the curvature to be used on the respective x and y axes. The curvatures may be defined by a radius of the curve or the height of the maximum point of curvature, if the radius is not known. These curves are used to project the midline of z-axis points until those projected points match the defined curve, as shown in FIG. 12D. This is done in both x and y axes to form one set of target points that encompass both x and y axis curves, as shown in FIG. 12E.

Figure 12F:
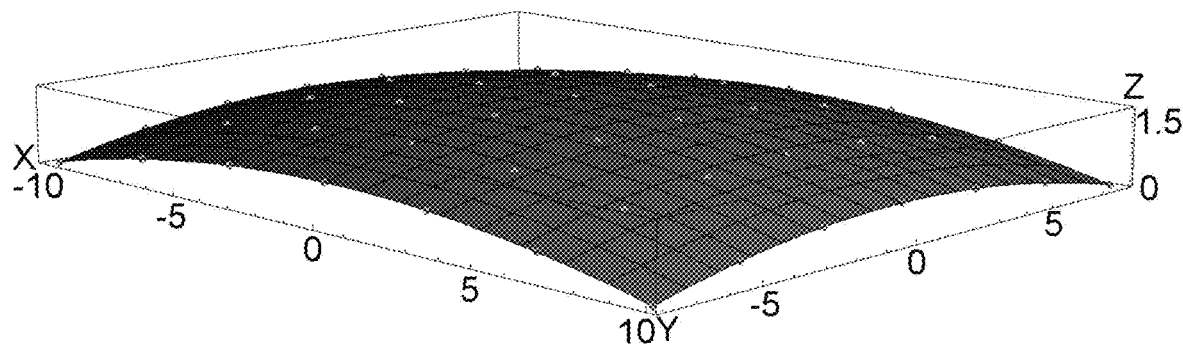
Figure 12G:
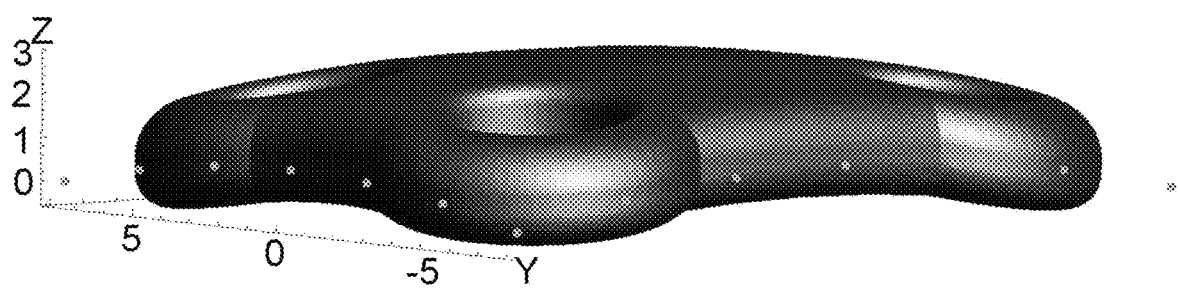

A warping function is then defined by these target points, shown in FIG. 12F. Once defined, the warping function is then applied to the original plate. This results in a customised plate that incorporates different x and y axis curves, but maintains all of the design features (for example surface edge fillets) of the original flat device, as shown in FIG. 12G.

Figure 12H:
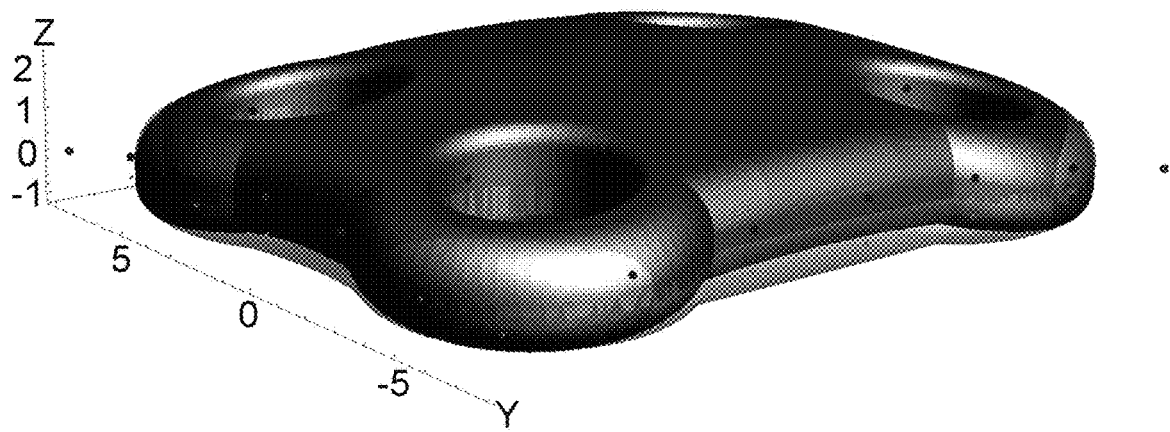

FIG. 12H shows the customised plate with differing x and y axis curves overlaid with the original flat plate. Note that the overall length and width dimensions remain constant, and that the degree of curvature in the final customised plate follows exactly that of the target points, which were created by the user defined curvatures in the x and y axes.

This example shows how the method of customisation can be applied to a mechanical device with user defined parameters controlling the customisation process. The resulting customised device maintains the design features of the original device, but now has additional design features, which in this example relate to horizontal and longitudinal curvature.

The same method could be used, for example, to customise the degree of curvature of an Intermedullary (IM) femoral, tibial, or humeral long nail. In the case of the Femoral IM long nail, these currently come with set radii of curvature, typically one of 2 metres, 1.5 metres, or 1 metre radius of curvature. However, these curvatures will not fit all patients, with curvatures having a radius that is too large impinging on the anterior cortex of the medullary canal, causing localised stress risers in the bone, potential bone remodelling, and pain.

The method specified here for the creation of a customised cervical plate can be used to customise the curvature of an IM long nail to better fit a patient. The patient's bone curvature may be calculated from a 3D reconstruction of a CT scan, or from measurements made on planar x rays.

The curvature in the IM long nails could be achieved by a number of different methods, including using a manual bending device, a bending device with numerical control over the degree of bend achieved, robotic bending, additive manufacturing, and CNC milling.

Cervical Cage

Inter (vertebral) body cages are used as 'spacers' to restore inter-vertebral body height. The central hole is often 'packed' with material such as bone 'crunch' (autograph or allograft; 'ground up' bone), sometimes used in conjunction with bone morphogenesis protein (BMP to help stimulate bone growth), or demineralised bone. All of these aim to maximise the likelihood of a successful fusion: where bone grows from the two end plates of the opposing vertebral bodies to unite in the middle. However, fusion is not guaranteed (see FIGS. 13B 1 & 2, the white line between the two vertebral bodies in 13B 2 indicates the lack of fusion).

Figure 13A:
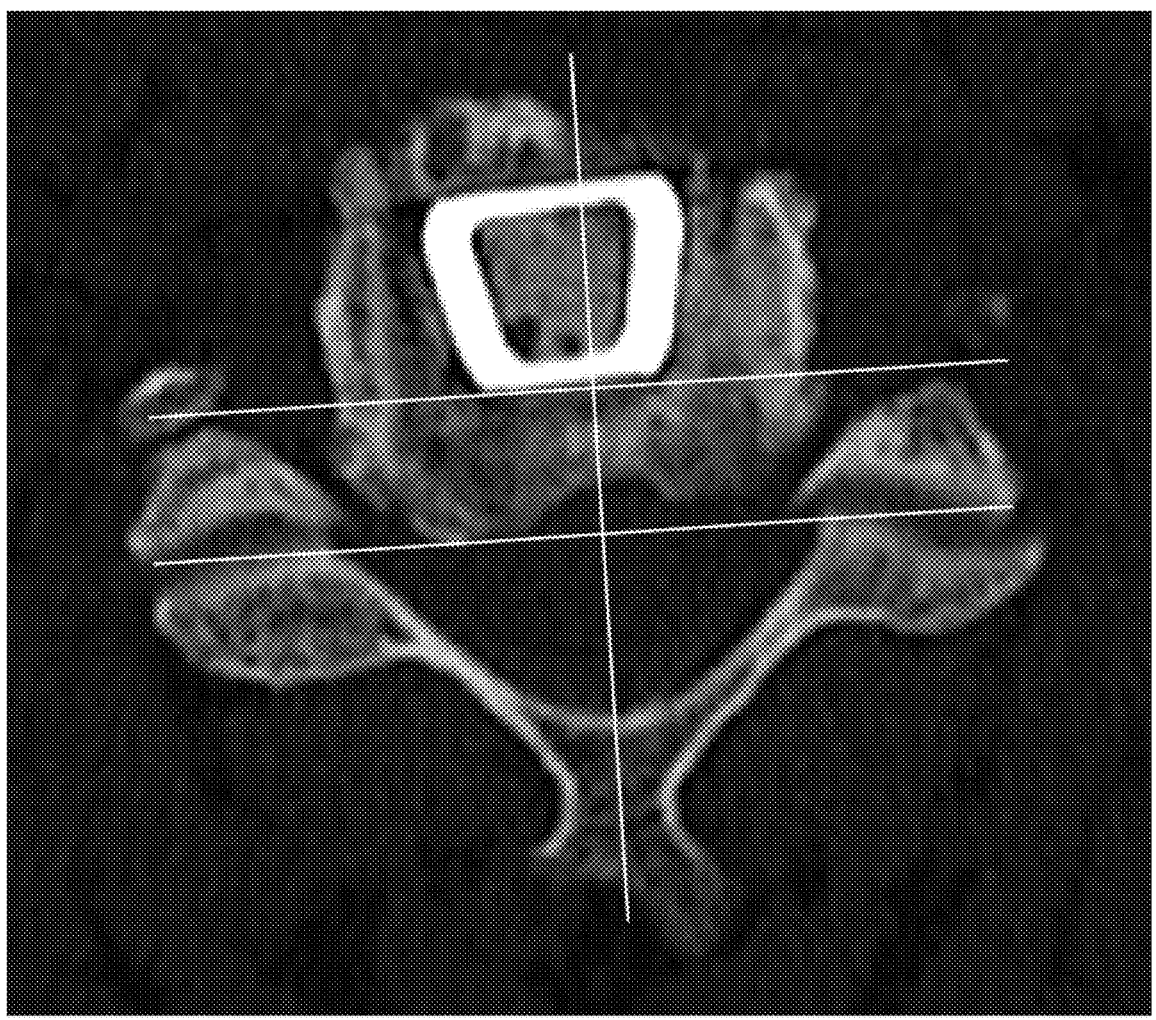
FIGS. 13A to 13K illustrate generation of a customised intervertebral body cage.
Figure 13B:
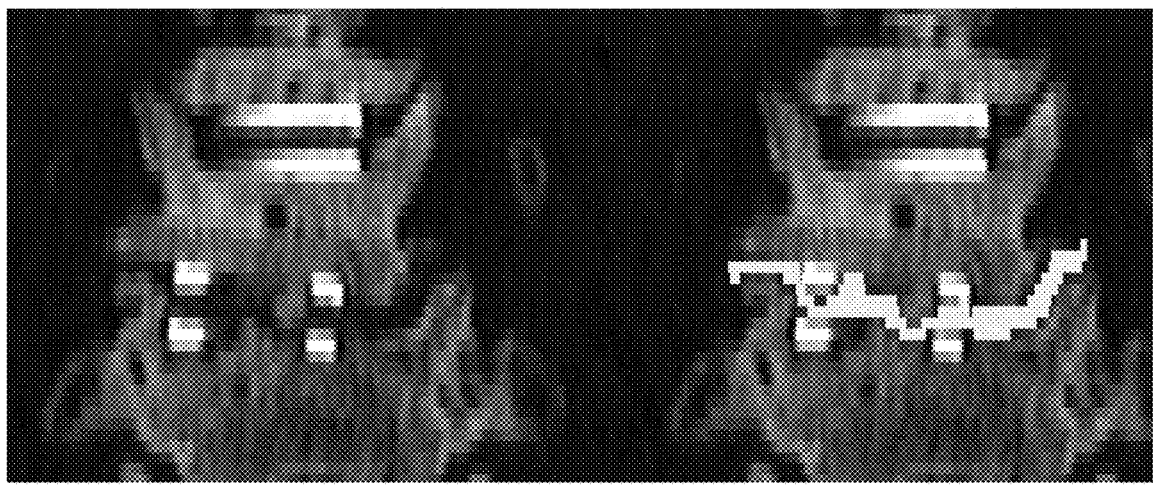

Currently, the cervical cages are difficult to place precisely, often ending up skewed and/or not centralised with respect to the spinal anatomy (see FIG. 13A). This is not a critical issue, but will affect how the force is distributed through the cage to either endplate.

Figure 13C:
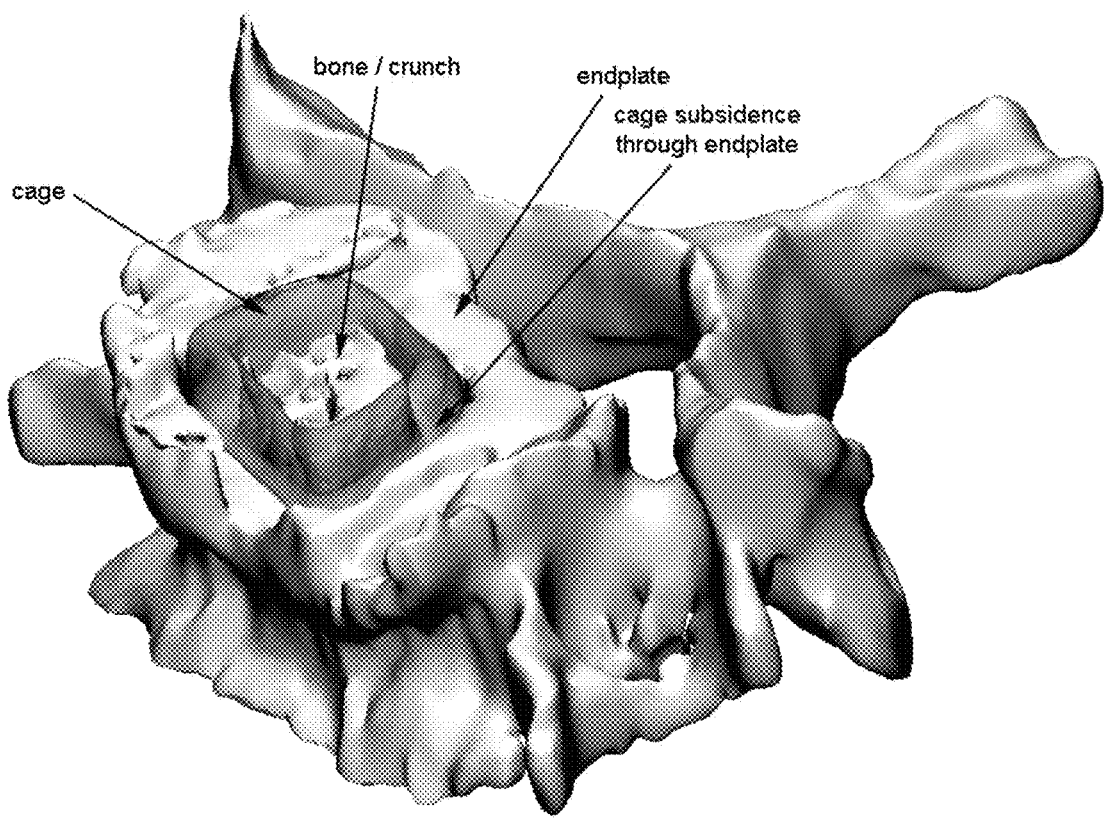
Figure 13D:
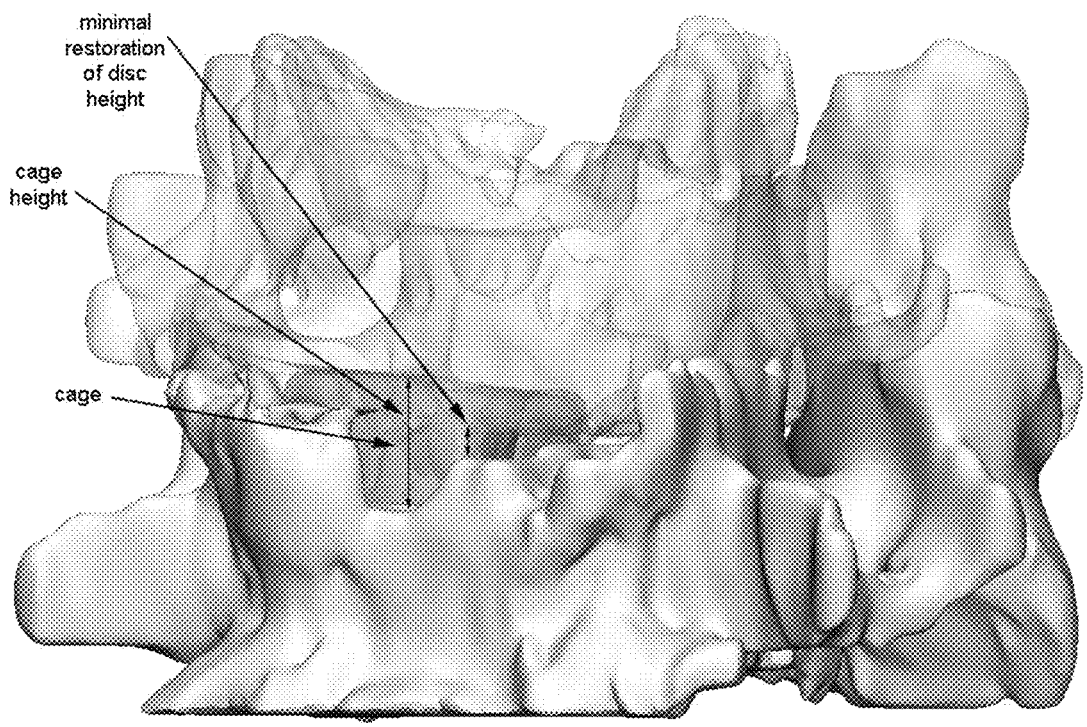

More of an issue is subsidence of the cages through the endplates into the vertebral bodies, see FIG. 13C. Subsidence is an issue, because as the cage subsides into the opposing vertebral bodies, so the inter-vertebral body height reduces, as shown in FIG. 13D. This can negate the main goal of the surgery, being to restore inter-vertebral body height and thereby increase the space for the nerve roots to exit the spinal cord.

Before placing the cages between the endplates, surgeons will frequently 'prep' the endplate bone. Prepping includes scouring and/or burring of the endplate. This serves to debride the endplates of soft tissues that would otherwise prevent bone-bone union and to activate the bone so that the bone starts to grow through and around the cage. However, if too much of the endplate bone is removed and/or disrupted during the prepping, the biomechanical integrity of the endplate can be compromised. This is particularly a concern in older, osteoporotic patients, where there is reduced bone mineral density in the vertebral bodies beyond the endplates.

Therefore, having a good fit between patient anatomy and device geometry is essential, as this will:

a) maximise the contact surface area of the device to the endplates, thereby minimising 'hot spots' of high stress (stress=force/area) that may cause the endplate bone to fail and the cage to subside into the vertebral body; and b) allow for better positioning of the plate, as the plate will naturally 'slot' into the desired/planned place within the surrounding patient anatomy. This will lead to a reduction in the incidence of un-planned 'off axis' loads being applied to the cage, which again can increase the likelihood of cage subsidence.

Figure 13E:
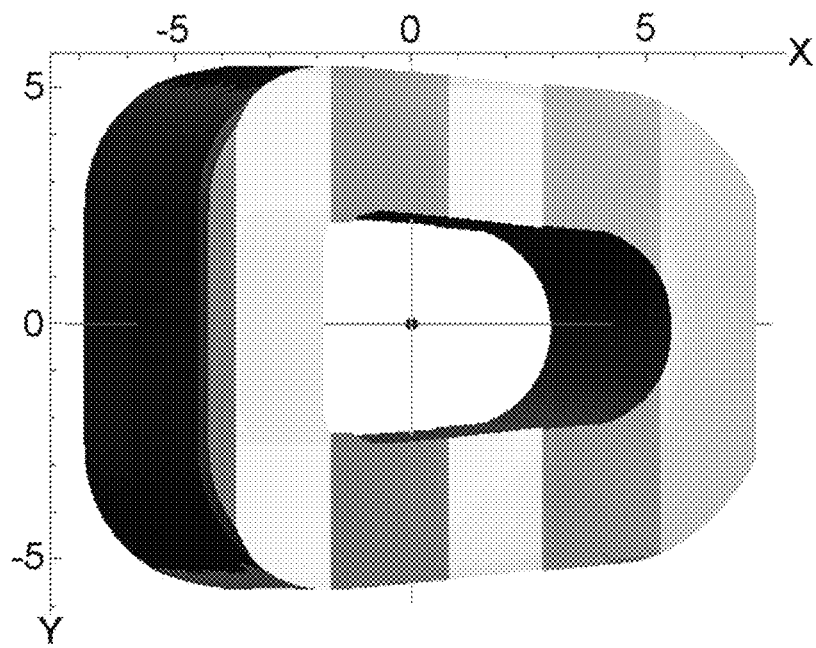
Figure 13E:
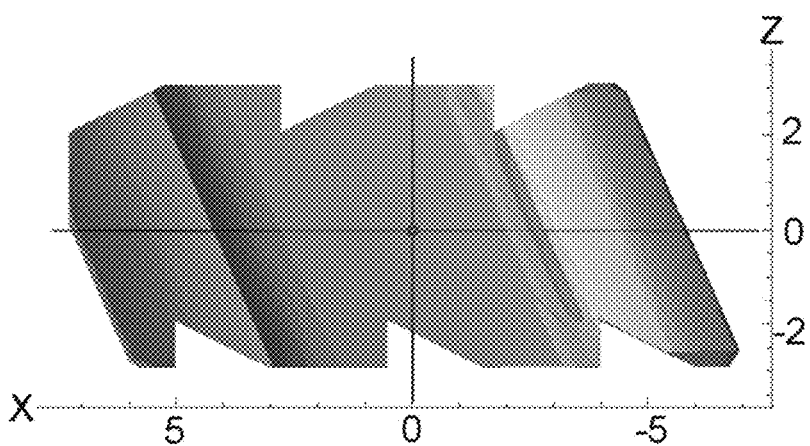
Figure 13E:
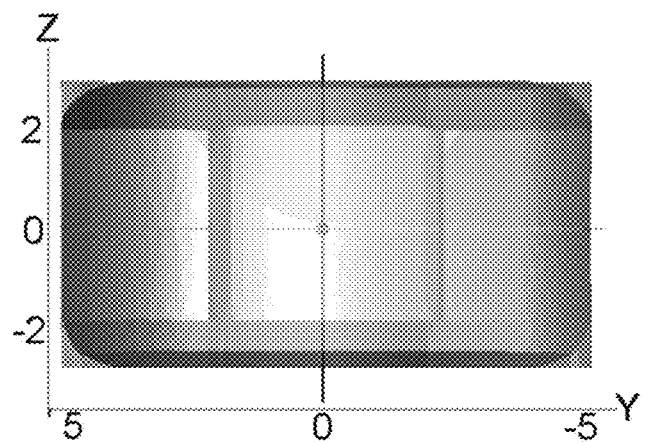

The method detailed herein allows for an inter-body cage device, or original/base geometry as shown in FIG. 13E, to be customised to fit a patient's specific anatomy. The example given here modifies the generic cage shown in FIG. 13E to fit a cervical spine of a dog.

Figure 13F:
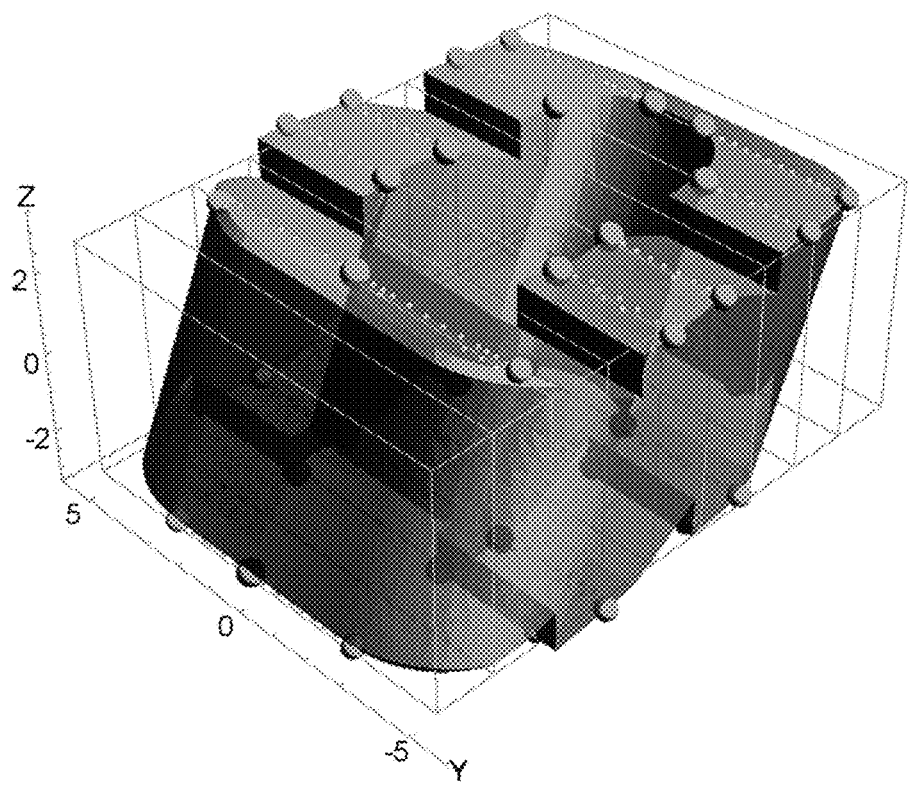
Figure 13F:
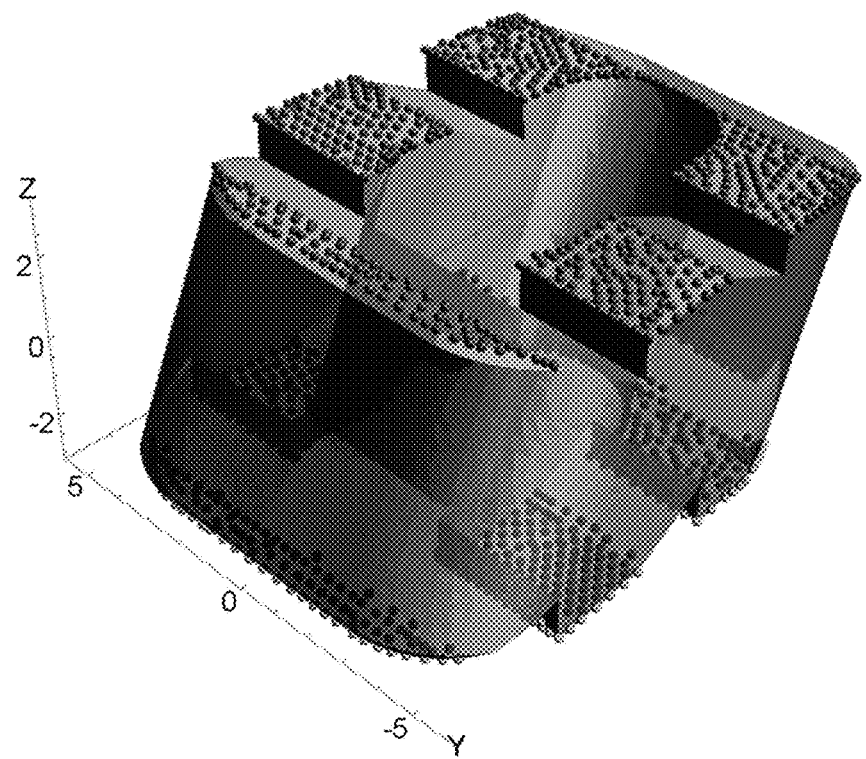

A first step selects points on the flat superior and inferior surfaces of the base device, which in this example is a generic cage. FIG. 13F shows two methods for selecting points. The upper image shows a grid approach, which selects grid lines intersecting the flat surfaces of the cage. Points at the extreme extents of the cage surface geometry are then automatically selected. On the lower image of FIG. 13F, all of the points on the superior and inferior surfaces of the cage are selected. This produces an accurate customisation, but most likely this number of points will unnecessarily slow the customisation process down without giving a notably better outcome, particularly when accounting for 3D printer tolerances and the unpredictability of the slight endplate shape alterations made by the surgeon burring.

Another method for point selection is by the user via a graphical user interface (GUI). Such a method of point selection is less favourable, due to the potential for unstandardized results.

Yet another method for point selection is for the generic device geometry file to have an associated file containing the positions of predetermined points. This associated file is loaded into the computer program at the same time as the generic geometry file, and all operations affecting the position of the device are also applied to the points. In this way, the points will maintain their predefined position to the original device geometry.

Figure 13G:
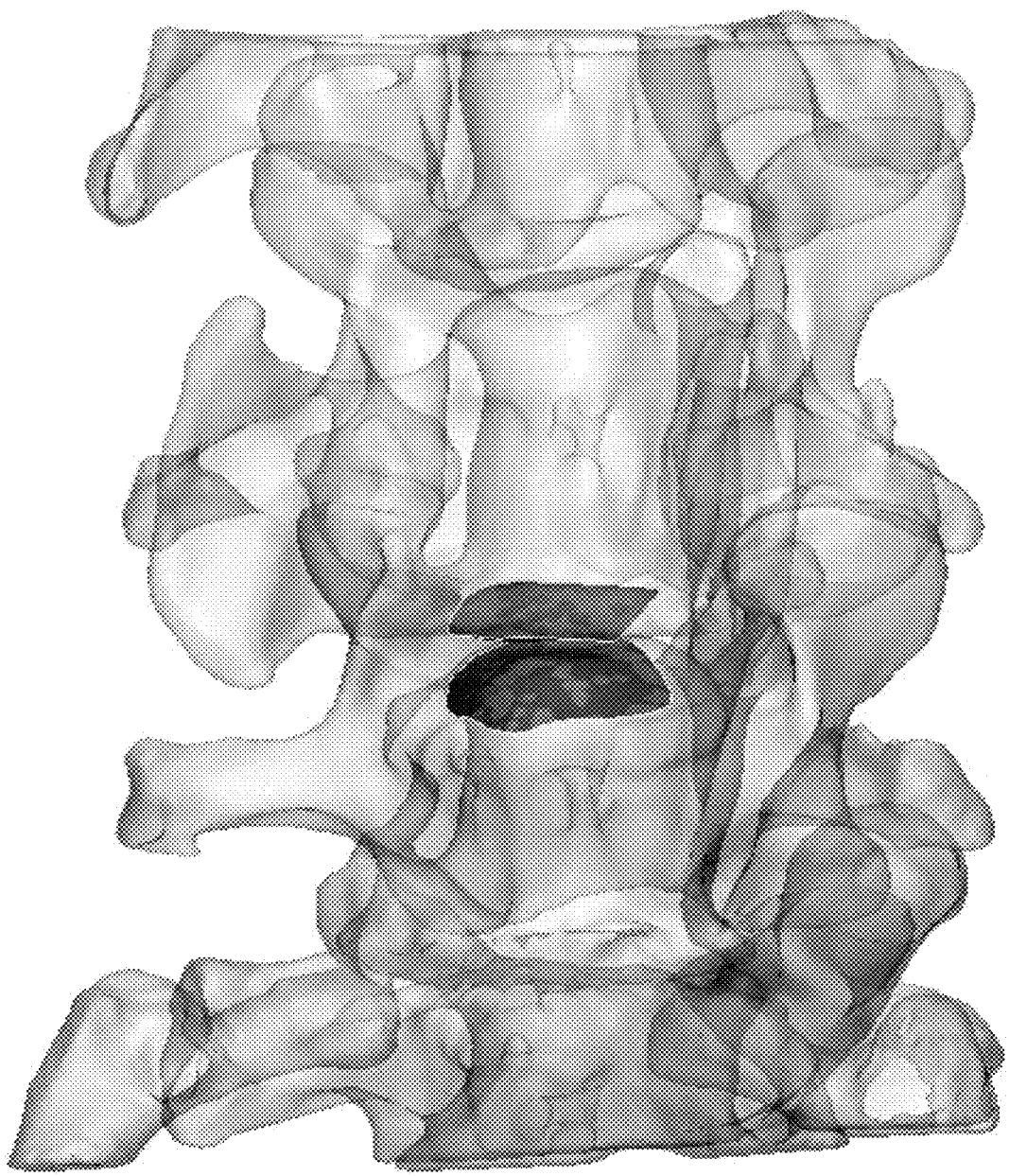
Figure 13H:
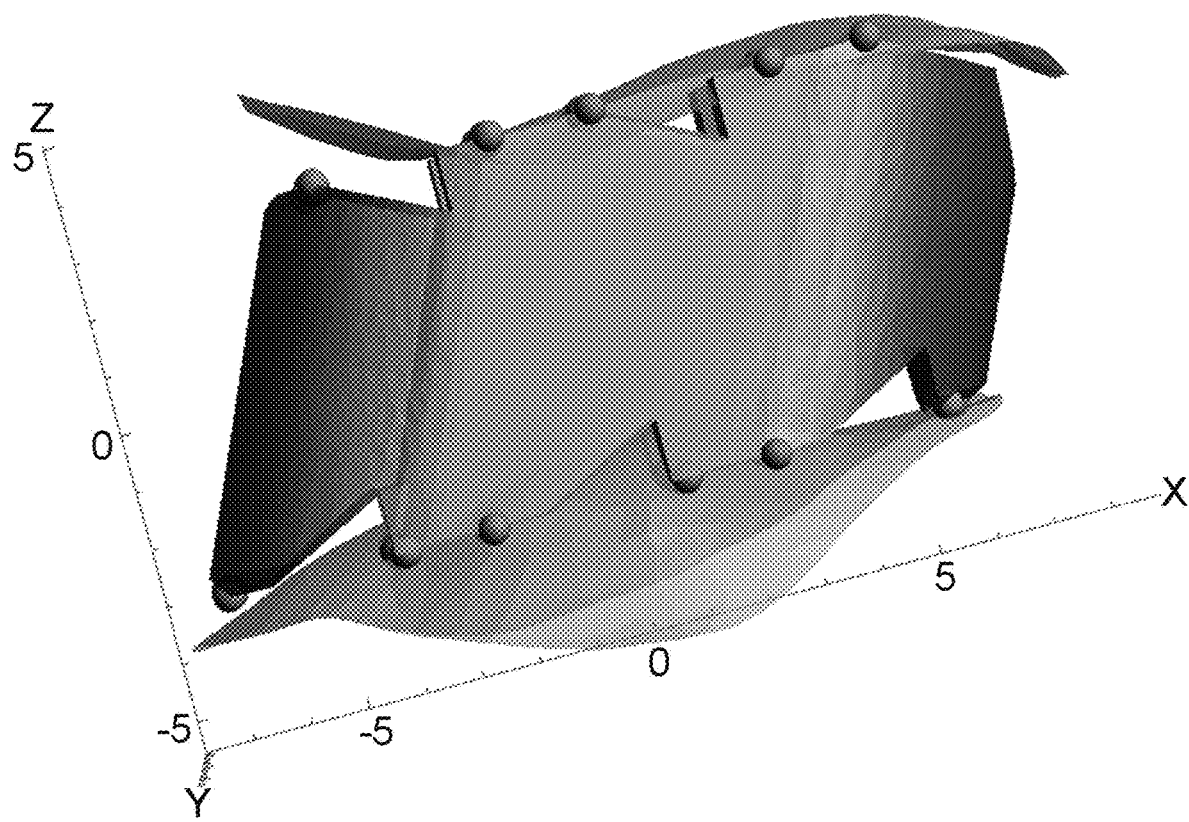

The endplates of the opposing vertebral bodies are isolated from a 3D surface reconstruction of the patient's cervical spine (shown as dark areas in FIG. 13G), which in this case is a Doberman (dog). The cage with picked points is manipulated until the cage lies between the two endplates. Slight overlapping of the cage with the endplates is to be expected. If the cage is notably too big in one or more planes, an initial affine warp can be performed to correct this. FIG. 13H shows a side on view of the inter-body cervical cage in between the two endplate surfaces of the adjacent vertebrae (see FIG. 13G). FIG. 13H also shows the original point positions.

Figure 13I:
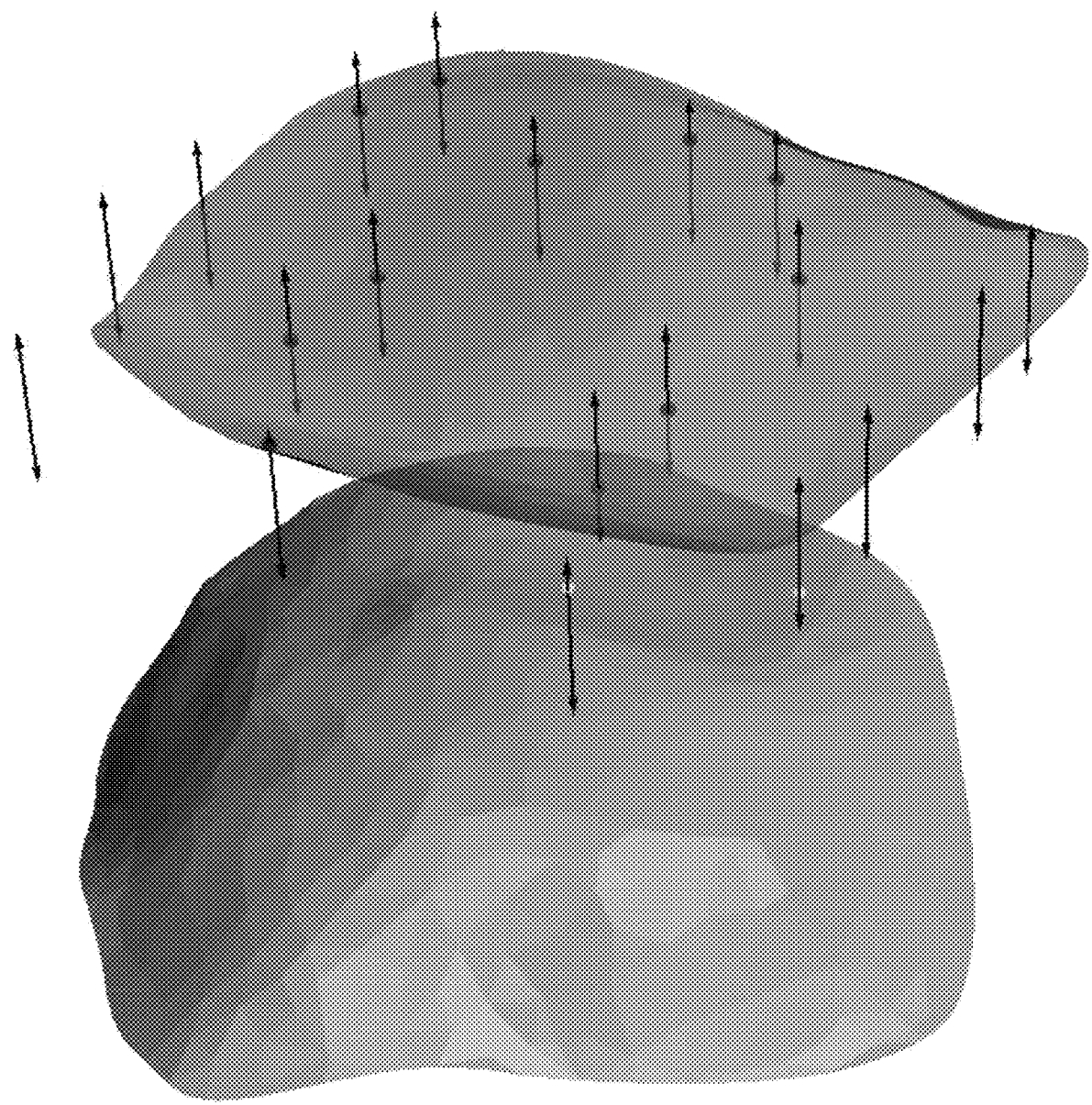

Once the cage is in the desired position between the vertebral body endplates, the points are projected along the projection vectors (dark arrows in FIG. 13I) until the projected points intersect the endplate geometry. The point of intersection is used to define a new 'target position' for the points (dark points in FIG. 13I). For points that do not intersect the endplate, a function based on the position of the closest endplate point can be used to calculate a suitable position (light grey points in FIG. 13I).

In this case, a moving frames linear optimisation or an As Rigid As Possible warping interpolation function is suitable for customising the base device. The function is defined based on the repositioning of the original points (light grey in FIG. 13J) to their 'target' locations (black in FIG. 13J).

Figure 13J:
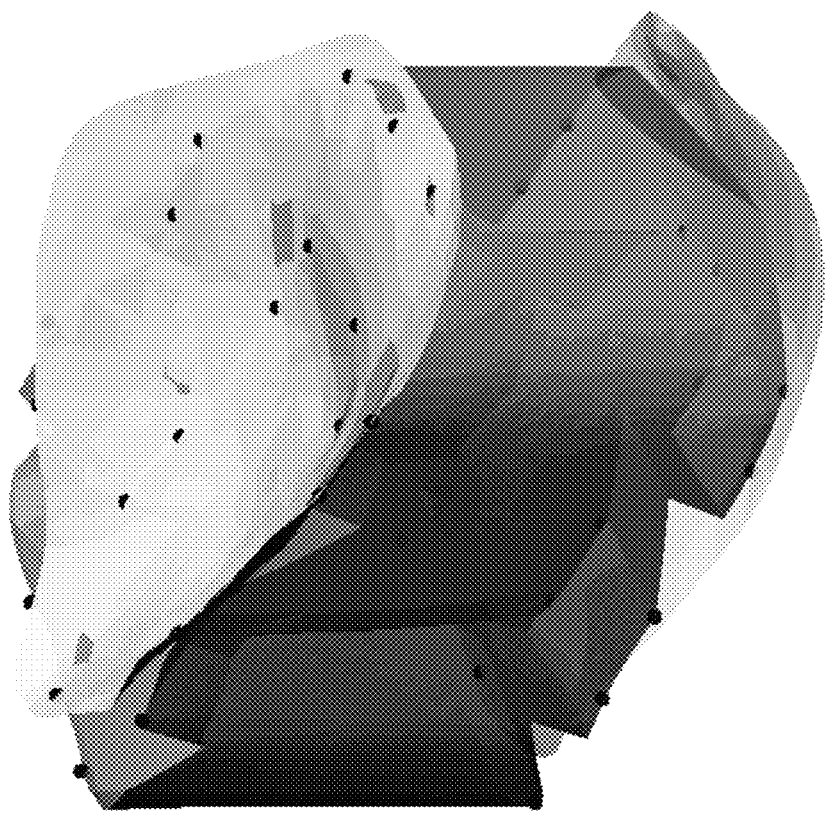
Figure 13J:
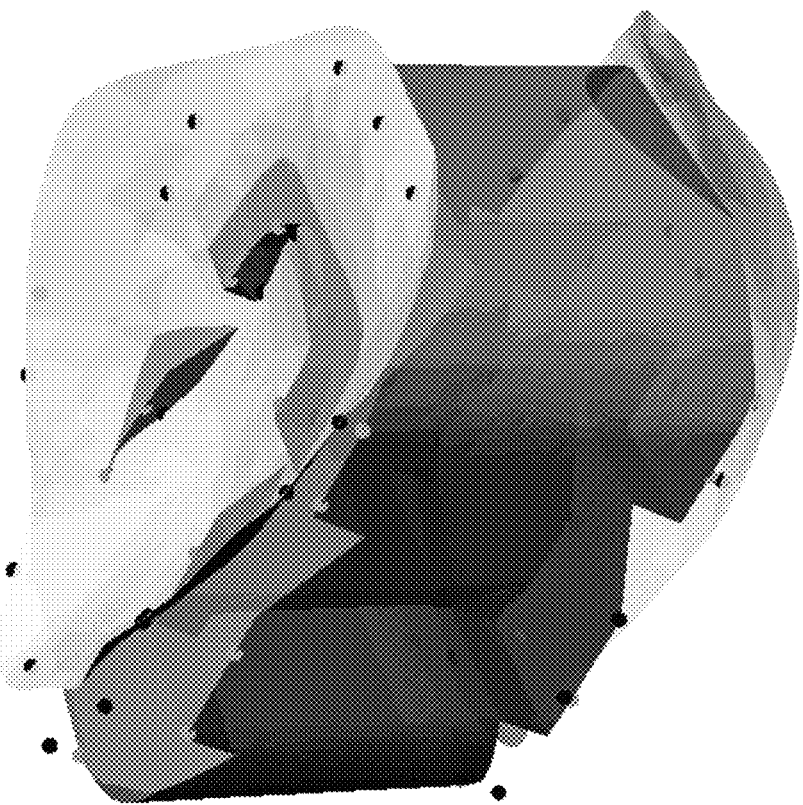
Figure 13K:
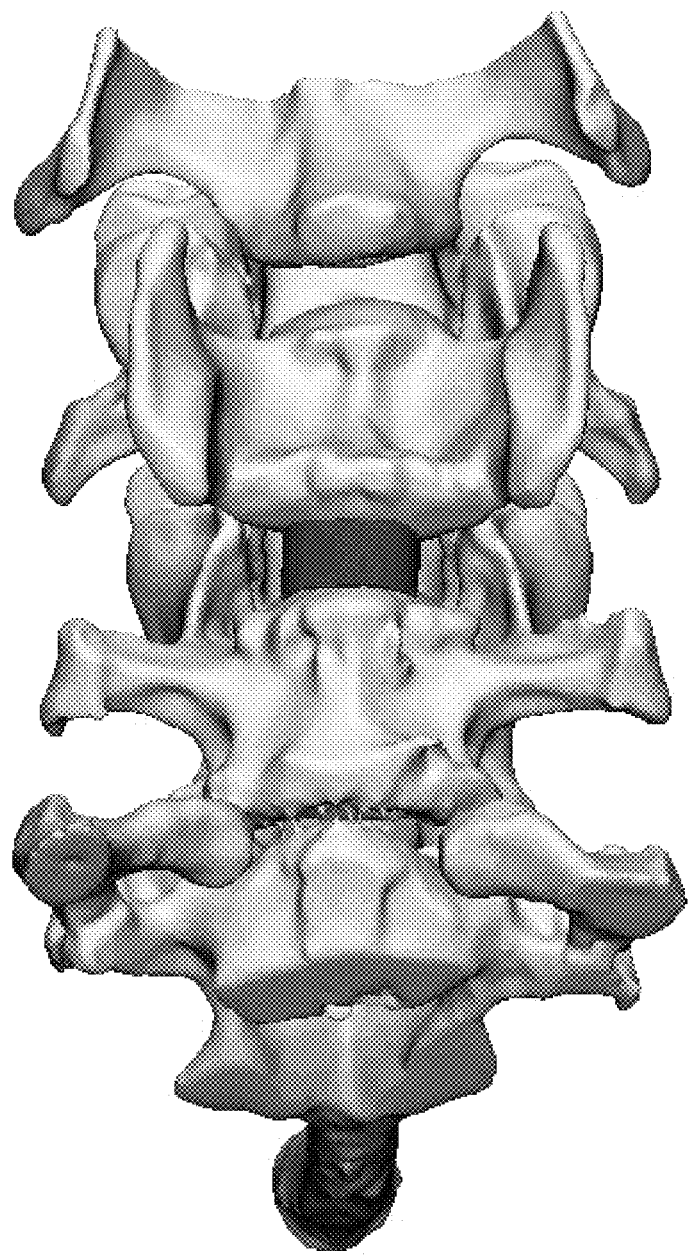

Once the warping function is established, the function is applied to the base model to create the customised device geometry (as shown in the right hand image of FIG. 13J). The customised device fits the endplate spacing and geometry well, as shown in FIG. 13K. Note how the customised geometry will help guide the device into its desired position during surgery, and help to hold the device in this position after the surgery.

The same method for customisation of original base geometry can be used in cases where there are not two opposing endplates, such as the customisation of a child's plagiocephalic head corrective helmet, or any other 3D geometry (see FIGS. 17C-H and FIGS. 18A-E and the description below).

Figure 14A:
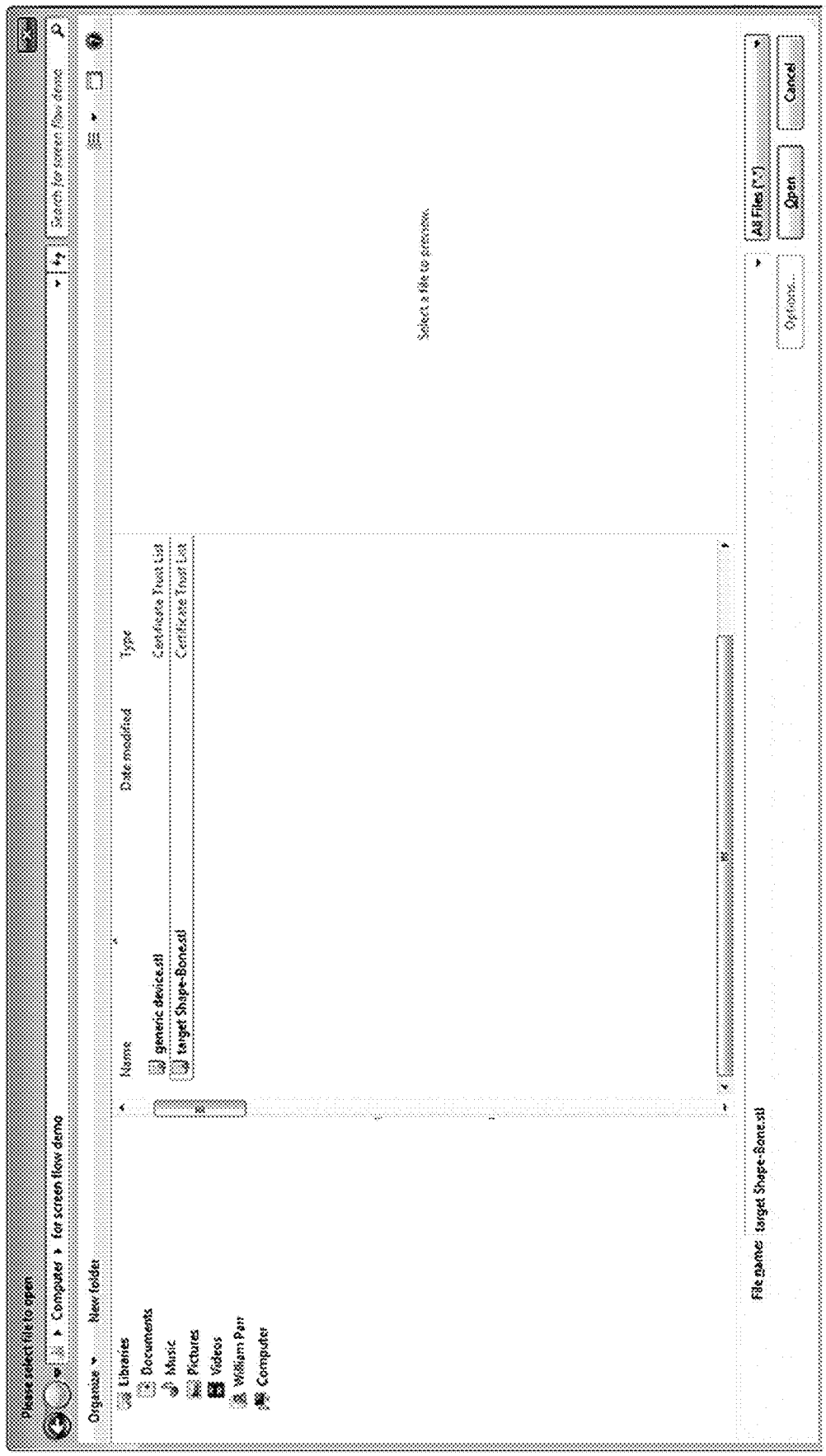

FIGS. 14A to 14H show screenshots of a graphical user interface (GUI) that can be accessed by a user to customise a base model. In the example of FIGS. 14A to 14H, the base model relates to a plate for a fracture, or osteotomy, fixation. FIG. 14A presents the user with an initial screen from which the user can select or upload a computer model of a generic base plate to be used in the surgical operation and a computer model of a target shape, which in this example is the bone to which the plate is to be attached.

Figure 14B:
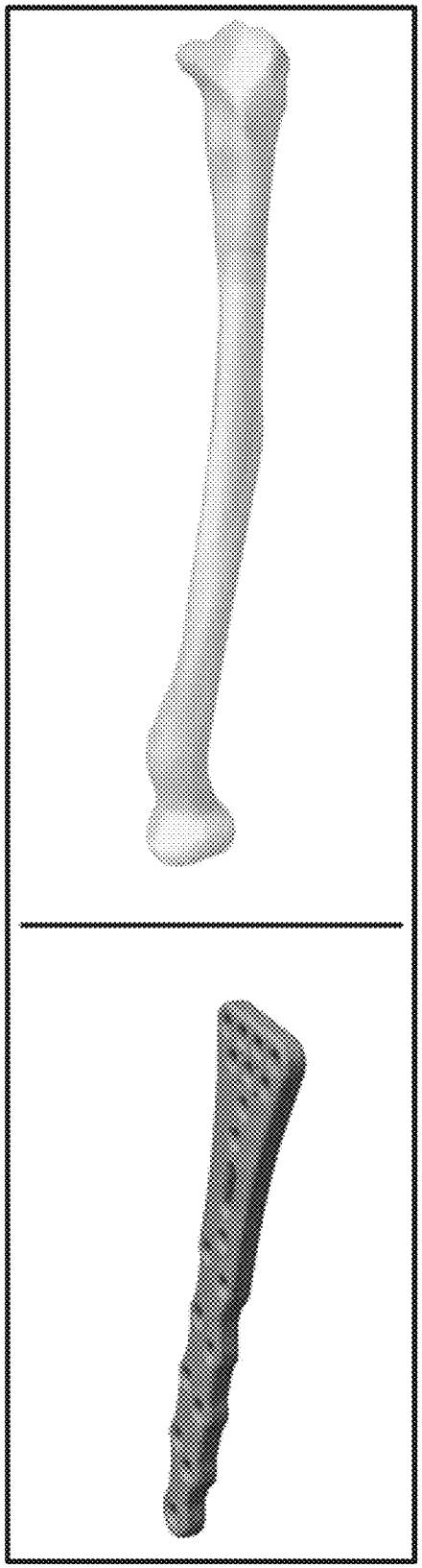
Figure 14C:
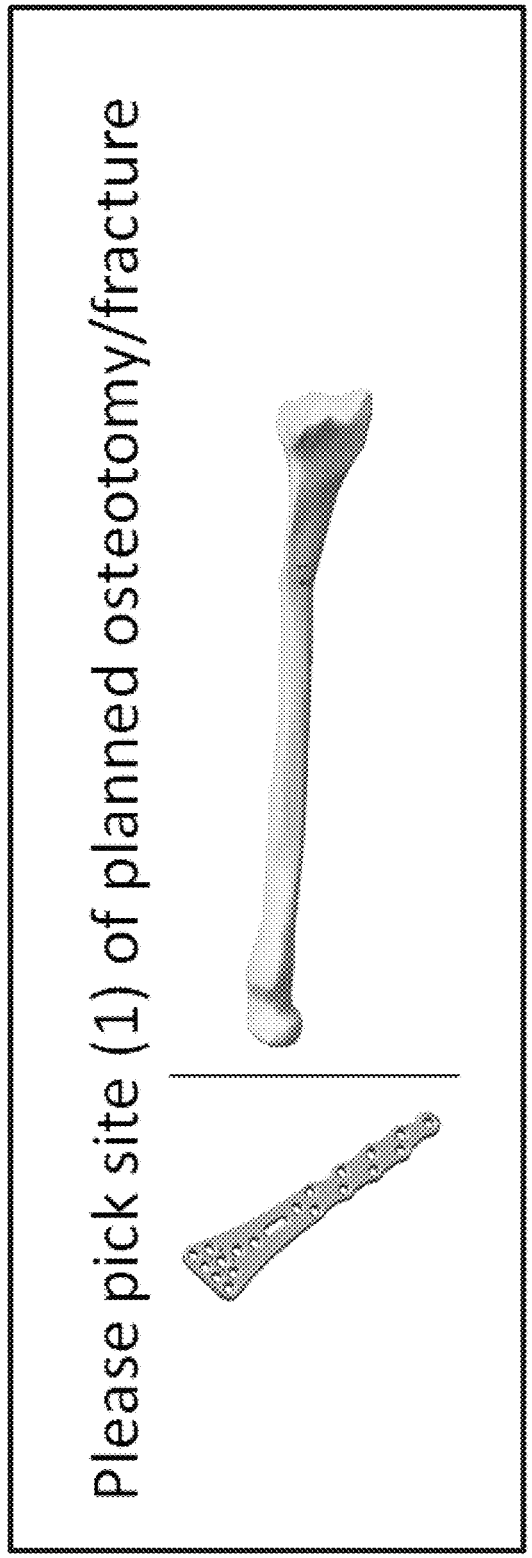

FIG. 14B shows a split screen arrangement, in which the selected base plate is shown on the left hand side of a screen and the target bone is shown on the right hand side of the screen. FIG. 14C presents the user with an image and instructions to pick a site (1) of the fracture or (future) osteotomy, where the plate is to be attached.

Figure 14D:
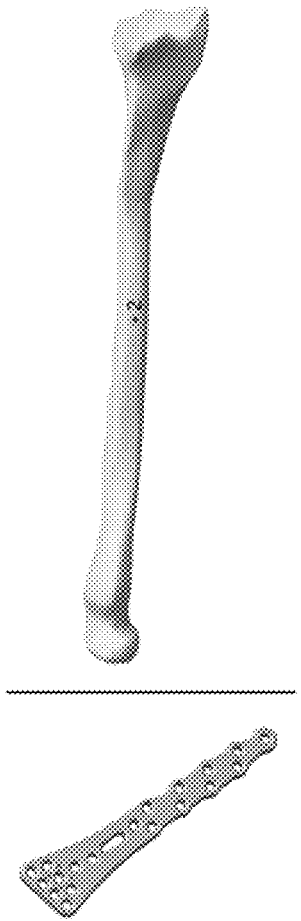
Figure 14E:
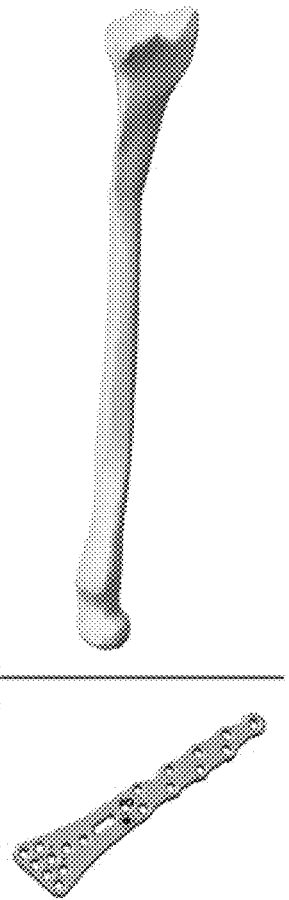

For fracture/osteotomy cases where the bone fragments will be re-aligned, user chooses an additional point (2) on the side of the fracture/osteotomy that will remain fixed. This is shown in FIG. 14D. FIG. 14E instructs the user to select a point (3) on the surface of the device that will face towards the bone (the bottom surface). This point must be on the planar surface of the plate.

Based on the selected points, the computer program implementing the customisation calculates inertial/principal axes for the device. The centroid, or mean p, of a point set P with N points is calculated as:

$$\mu_p = \frac{1}{N_p} \sum_{i=1}^{-N_p} p_i \qquad \text{Eqn (1)}$$

The vector matrix is centred at x,y,z=0,0,0 by subtracting $\mu_p$ from each of the 3D points making up the boundary representation of the matrix:

$$(x_p\mu_p, y_p\mu_p, z_p\mu_p) = (x_p, y_p, z_p) - (x_{\mu_p}, y_{\mu_p}, z_{\mu_p}) \qquad \text{Eqn (2)}$$

A square matrix (SM) is calculated as the covariance of the transposed centred matrix (M):

$$SM = Cov(M^T) \qquad \text{Eqn (3)}$$

The eigenvectors (Evecs) of SM are calculated:

$$(Escores_1, Evals_1, Evecs_1) = \text{SingularValueDecomposition}(SM) \qquad \text{Eqn (4)}$$

The eigenvectors (Evecs1) of this matrix are checked using the right hand rule and the orientation of the PC axes that have the minimum rotation angle is selected. The resulting vectors are the Principal, eigen, or inertial, axes of the device.

Either the normal vector of point (3) is calculated (using Eqn(5)), or a user defined projection vector, or the normalised global z-axis (0,0,1) are used as a projection vector. The normal vector ($v_n$) for a point (p1) that is in a triangular polygon with points p2 and p3 is given by the cross product of the vectors $v_{12}$ (p2−p1) and $v_{13}$ (p3−p1):

$$v_n = \text{cross}(v_{12}, v_{13}) \qquad \text{Eqn (5)}$$

The magnitude of this vector ($v_n$) is given by:

$$v_{mag} = \sqrt{v_{nx}^2 + v_{ny}^2 + v_{nz}^2} \text{ or } \sqrt{v_n \cdot v_n} \qquad \text{Eqn (6)}$$

$V_n$ can be normalised to a unit vector (magnitude=1) by:

$$\text{normalised } v_n = \frac{v_n}{\sqrt{v_n \cdot v_n}} \qquad \text{Eqn (7)}$$

The generic plate for customisation is automatically aligned to the global coordinate system axes by:
a) translation of the device's centroid to the global x,y,z 0,0,0 (as in Eqn(1) & Eqn(2)); and
b) rotation around point (3) so that normal vectors of points (1) and (3)*−1 are aligned.
This is achieved by:

$$(Escores_2, Evals_2, Evecs_2) = \text{SingularValueDecomposition}(v_{npt3}^T \cdot v_{npt1}) \qquad \text{Eqn (8)}$$

$$\text{RotMat} = Evecs_2 \cdot \text{IdentityMatrix}(3) \cdot Escores_2^T \qquad \text{Eqn (9)}$$

where RotMat is a 3×3 rotation matrix that will achieve the desired alignment when the dot product of RotMat is calculated for all of the points in the device. That is, for each point ($P_x$ being any given point in the device) the following is calculated:

$$P_x \cdot \text{RotMat} \qquad \text{Eqn (10)}$$

The user is asked whether the orientation of the plate is correct, if not, rotate plate by 180 degrees around point (3) in the global z-axis (Eqn (11)) by calculating the dot product of each point and the rotation matrix:

$$z\text{-axis RotMat} = \begin{matrix} \cos\theta & -\sin\theta & 0 \\ \sin\theta & \cos\theta & 0 \\ 0 & 0 & 1 \end{matrix} \qquad \text{Eqn (11)}$$

where θ=180°*(Pi/180) (i.e., θ is in radians).

If the guide orientation is still not correct, the user can adjust the position by rotating around x,y,z in global/screen/inertial axes:

$$x\text{-axis RotMat} = \begin{matrix} 1 & 0 & 0 \\ 0 & \cos\theta & -\sin\theta \\ 0 & \sin\theta & \cos\theta \end{matrix} \qquad \text{Eqn (12)}$$

$$y\text{-axis } RotMat = \begin{matrix} \cos\theta & 0 & \sin\theta \\ 0 & 1 & 0 \\ -\sin\theta & 0 & \cos\theta \end{matrix} \qquad \text{Eqn (13)}$$

where θ is user specified either by inputting numerical values for rotations, or by adjusting on screen slider bars for x,y,z rotations. The plate is then correctly aligned with the global coordinate system. The fracture/osteotomy site of the target bone is then aligned, using a similar method, with respect to the plate, in the desired position relative to the plate, within the global coordinate system. FIG. 14F shows a screenshot presented to a user to verify the relative positioning of the target shape and device with one another. Core TPS warping for plates, flanges, guide base surfaces (see FIG. 6, FIG. 7, FIG. 9)

In this example, the source points for the device are defined. These source points are either stored in a file accompanying the original device file or alternatively the source points can be defined by a standardised grid calculated from the bounding box of the device (see 605 of FIG. 6A). As a further alternative, the source points can be defined as an equidistant subset of points that lie in plane with point (3), or the source points can be selected by the user via interaction with the graphical user interface. The grid algorithm includes points at PC axes extremes and mid points (see 605 of FIG. 6A).

All of these source points are assigned the normal vector of point (3) and projected by transDist (Eqn (14) below) until the points intersect polygons on the bone surface (Eqn (15) and Eqn (16) below).

$$\text{transDist} = \text{norm}(v_{npt3})*(k*v_{mag}(\text{bone}PC3)) \qquad \text{Eqn (14)}$$

Vectors are constrained to have a maximum projection of a constant, k, *bone z axis (Eqn (14)) bounding box magnitude (see 610 of FIG. 6A). In cases where the projected point 'misses' the target morphology (for example, the target morphology is not reached by the magnitude of the projection vector set by the user or by Eqn (14)), a function is used to place the target point. This function is a combination of a position on the projection vector and the nearest point orthogonal to the projection vector on the target morphology.

The point of intersection ($pt_{int}$) of the normal vector ($v_n$) and a triangular polygon can be written as.

$$pt_{int} = a*(v_n + p_1) \qquad \text{Eqn (15)}$$

where $v_n$ is the normal vector of $p_1$, or as in the case here, the normal vector of pt(3), a is a scalar magnitude which is found, in conjunction with s and t, by solving the equality of the parametric equation for a triangle, given by three corner coordinates ($tp_1, tp_2, tp_3$), and a for where 0<s<1 and 0<t<1.

$$a*(v_n + p_1) = = (tp_1*(1-t)*s) + ((tp_2*t*(s+tp_3))*(1-s)) \qquad \text{Eqn (16)}$$

The triangle in which the point is located can be found in a number of ways. Solving the equality for every polygon in the boundary representation will give the answer, but is computationally very inefficient. A more computationally efficient method is to use a nearest function to calculate which point on the target surface is closest to the $p_1 + v_n$. This point will be the corner of a number of triangles. It can then be determined through which of the triangles the vector passes and the point of intersection (Eqn (16)) of the vector and the triangle surface. This is the 'target point' location (615 of FIG. 6a).

A warping interpolation function is then calculated by fitting all of the source point positions to their target positions. These are the known points that allow the interpolation function to be established. This function could, for example, be a thin plate spline function such as in Eqn (17), as shown in 620 of FIG. 6B:

$$\text{distance}^2 * \log[\text{distance}] \qquad \text{Eqn (17)}$$

The thin plate spline dictates the warping effect on the base part (device) points that lie in between the source (control) points. The thin plate spline is a distance function that calculates the distance of a base part (device) point from the source (control) points.

Different functions control how base part (device) points that lie in between the source point positions are warped.

These functions are interpolative functions because they calculate the new, or warped, position of a device point depending on how far the point is from a control point. In this way, the functions can calculate the new positions of device points that are in between the control points. Hence, the functions are termed warping interpolation functions.

The results of the function on the base part (device) points vary through the space spanned by the function, according to the proximity of the base part points to the source points. The functions described here are therefore abstracted from the base part (device) itself, depending only on the source and target points, which are separate from the base part.

As the warping interpolation functions are abstracted from the base part (device), where different devices are required to fit the same target morphology, the same warping interpolation function can be used. For example, a jig that positions bone fragments or cut parts in the desired post-operative position could use the same warping function as the plate that will be used to fix these parts in the desired position.

Another use of the term interpolation, within the field, is to describe how missing (bone) regions can be replaced. In this use of the term a model of the normal, or correct, bone anatomy is superimposed, or aligned with, the pathological, or missing, anatomy. The missing region of the bone is then filled in by interpolating between the opposing edges of the missing bone according to the superimposed good bone model. In such an example, interpolation is used to correct pathological or missing bone anatomy, with the interpolation using the bone anatomy. The interpolation is therefore specific to the pathological, or missing, anatomy and cannot be generalised, or applied to another bone/model.

Warping and interpolation terminology are also used in the field to describe a different process to that described in the present disclosure. In this alternative use of warping and interpolation, a bone model may be altered in shape, or 'warped', to fit a region of a patient bone that has a defect of missing part in another region. This model can either be statistically defined, for example as an 'atlas' bone model from a bone database, or by mirroring the opposite side of the patient's own anatomy if this anatomy is normal.

The altered bone model can then be used to replace the defect or missing bone. This replacement of the defect or missing bone may then be used as the starting point for modelling a device to fit the defect or missing region.

Alternatively, the altered bone model can also be used to aid in selecting the best fitting device from a database of generic devices. This method could be used to select the generic device, or base part, for the customisation method presented in the current disclosure, but is not a necessary, nor integral, part of the method disclosed here.

The alternative use of interpolation in the field is different from the use of interpolation in the present disclosure, where the warping of (target) space in between source (control) points is calculated by interpolation of the warp at the known (source) points.

As an example, in the case of a missing region of the cranium, the part of the altered, or warped, statistical bone model may be used to begin the production of a custom cranial metal or polymer plate. In such a case, the statistical model is used to define the thickness, curvature and outline shape that a plate would need to be an effective replacement for the damaged or missing bone region. This part of the statistical model can then be isolated, for example by a Boolean intersection or subtraction, from the remainder of the statistical cranial model. Computer Aided Design (CAD) methods can then be used to adapt this isolated part of the shape into a CAD model of a plate suitable for manufacture and implantation, for example by adding flanges with screw holes for attachment of the plate to the bone surrounding the defect. This is termed a 'bottom-up' customised device design process, as the design of the device starts from the bone surface, or a model of the bone surface, shape and adapts this shape to become a device that can be manufactured.

This is a different use of warping to the present disclosure. In the present disclosure a warping function that alters the shape of space is established based on points, or measurements, that are abstract, or separate, from the bone or an already existing device (base part). This warping function is then applied to a pre-existing generic medical device (the base part) to achieve a customised shape of this device that fits the patient, or target, anatomy.

Another way to alter, or warp, the shape of a device is through a shear, or affine warp, of space. This is achieved through different scaling factors being applied to the different axes, for example to length, width and depth axes, of a shape. Differential scaling of the length, width and depth of a shape will result in an 'affine' shape change. This is a more simple, and limited, shape change than that described in the present disclosure. This is because the affine method of shape warping is constrained, within each axis, to apply a uniform distortion of the shape for the entire length of that axis.

Once the warping interpolation function is calculated, the new (warped) positions of the original (base) device's points are calculated by resolving the interpolation function for each of the point start positions (FIG. 625). For guide & locking plate warping, pre-defined areas (drill holes, screw holes, cutting saw blade cutting guides) are prevented from non-rigid transformations and scaling (i.e., such areas are allowed to translate and rotate, but not scale or warp shape).

The warped device is then checked for collision/intersection with bone (if points of device lie inside bone envelope, then iteratively translate device points in by −0.1*transDist (Eqn (14))*pt3 normal vector (by vector subtraction from each point in the device) until collision is resolved), as shown in 630, 635, 640 of FIG. 6C.

Figure 14G:
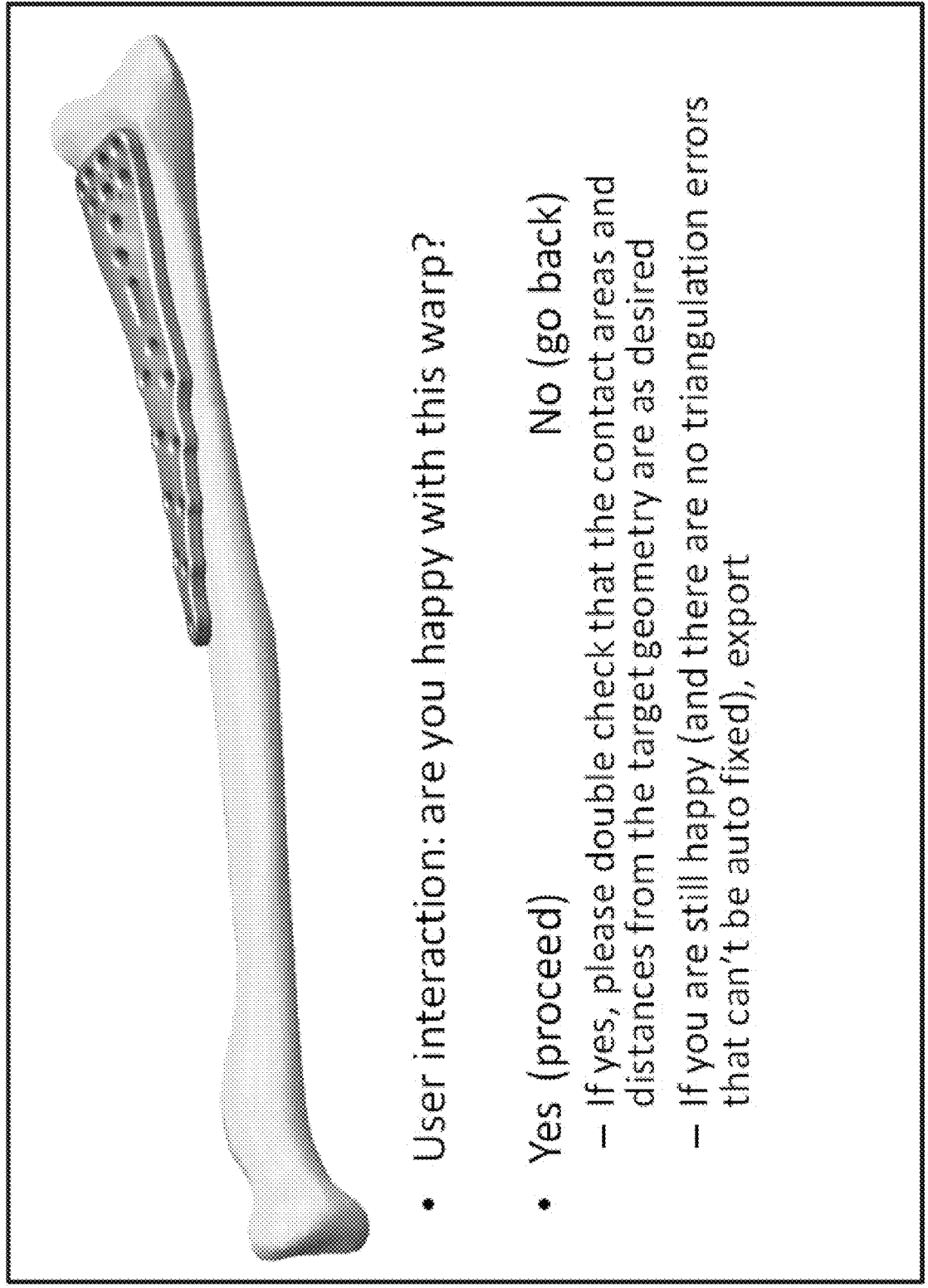
Figure 14H:
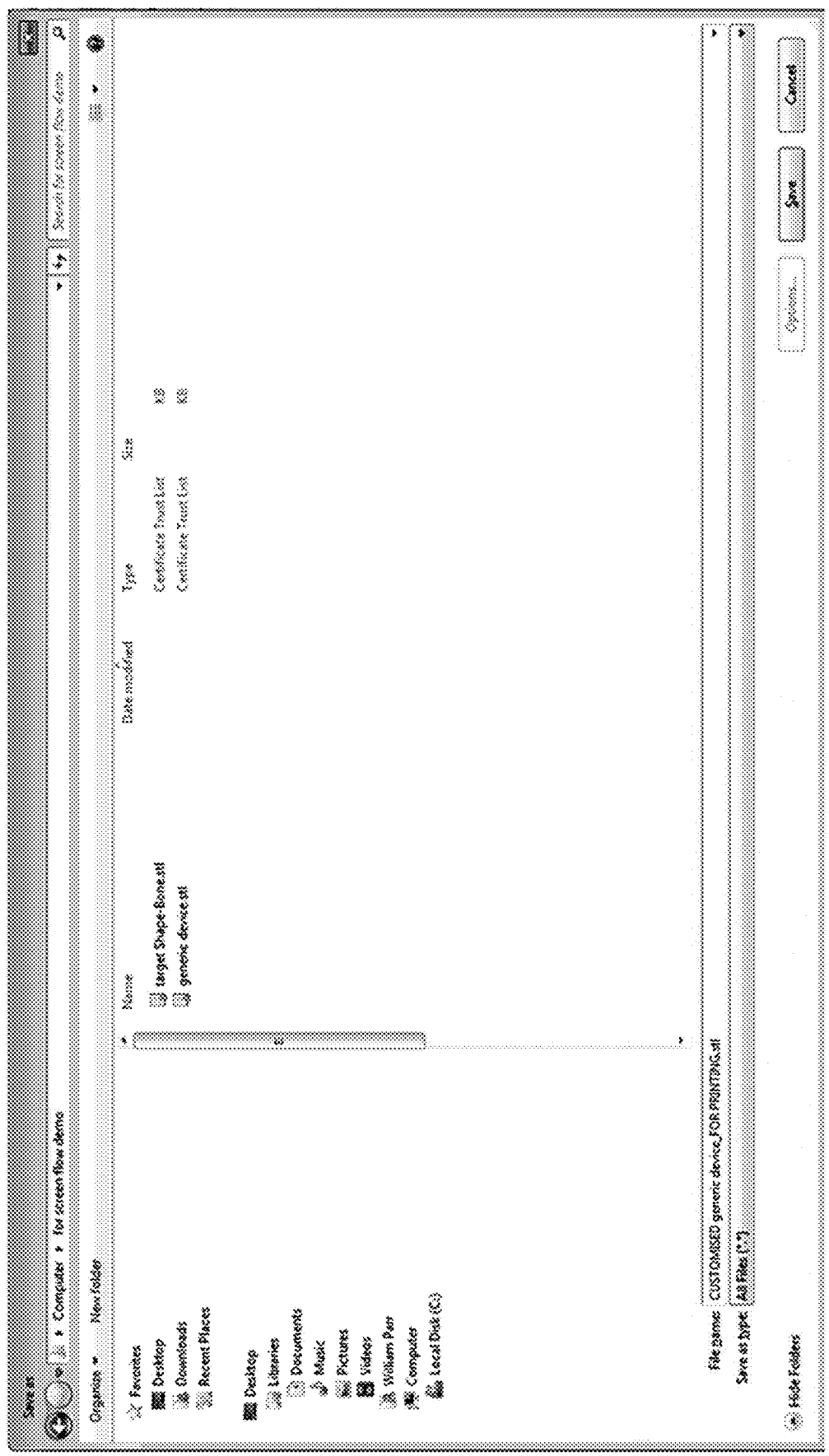

The following checks are then performed on the resulting warped device: a) check the triangles are valid, and b) prompt user to confirm result is ok (shape, distance from bone, amount of contact between device and bone). FIG. 14G is a screenshot presented to a user to confirm satisfaction with the presented warp. On acceptance of the result, pop up an export directory window, as shown in FIG. 14H, and export as .stl or .wrl file format for 3D printing.

Bone and device are moved back to the original position of the bone and orientation by vector addition of the translation vector that translated the bone to 0,0,0 and the dot product of the reverse of the rotation matrix that aligned the bone surface point (3) normal with the global z axis.

Core Method for User Measurement (Parameter) Customisation of Device (e.g., Splints, Orthotics, Braces, Plagiocephaly Helmets from Measurements of yhe Child's Head, Protective Clothing, Cutting/Drilling Guides, See FIGS. 11A-C)

In this example, a device is aligned with centroid at global x,y,z=0,0,0 with x axis=length, y axis=width, z axis=depth of device (see Eqns (1) to (10) above and FIGS. 11A and 11B). A user then enters predefined measurements, as shown in FIG. 11C. The method alters a predefined generic device design grid at each measurement level is to match user-defined measurements and establishes a radial basis interpolation field (FIGS. 11D and 11E).

All device coordinate points are resolved to a new warped position in the radial basis interpolation function and the user checks results (FIGS. 11F and 11G). The triangles are then checked and the model is exported as .stl file for 3D printing or other computer manufacturing process.

Core Method For Parametric Customisation Of Device (e.g., Adding Parametric Curves to a Cervical Fusion Plate or Inter-Medullary, IM, Long Nail, See FIGS. 12A-12H)

In this example, the method aligns a device with the device centroid at global x,y,z=0,0,0 with x axis=length, y axis=width, z axis=depth of device. The user then enters predefined curve parameters/measurements. These parameters can be in the form of curve radius, or in the form of 3 points on the desired curve perimeter, or in the form of the distance at the mid (high) point of the curve from a flat surface/plane on which the two ends of the device are resting.

The defined curve parameters are used to create either an arc, or a curved plane (for two simultaneous curves), which are used to create the target point positions (see FIG. 12E and FIG. 12F). All device coordinate points are resolved to new warped position by the warping interpolation function, which is determined by the source and target points (FIG. 12G). The user checks the result (FIG. 12H). The model is checked, or validated, for 3D print suitability (intersecting triangles, non-manifold edges, holes in the boundary surface are check for and fixed), and the model is exported as .stl for 3D printing.

This validation of the 3D model for print suitability is different from a validation of the model by virtual testing, for example by Finite Element Analysis (FEA). The validation of the model is purely a validation that the model produced is suitable for 3D printing in that the model does not include any surface (triangle) errors that mean the model would not be printable. Once this validation has occurred, then the model could be also be entered into FEA, once volume meshed, for virtual testing. However, FEA testing of a model is not novel, and not an inherent part of the present disclosure.

Core Method for Unstructured (True 3D, i.e., Not Plane, Curve or Grid Structured Points) Source and Target Point Customisation of Device (e.g., Customisation of an Intervertebral Body Cage, See FIGS. 13A-13K)

The device is aligned with centroid at global x,y,z=0,0,0 with x axis=length, y axis=width, z axis=depth of device. Target morphology is aligned with centroid at global x,y,z=0,0,0 with x axis=length, y axis=width, z axis=depth of device. Device/target position and alignment are adjusted, if needed, so that device and target are aligned as desired/so as to achieve effective projection of device source points to target morphology (see FIG. 13H).

Source points are projected until intersection with target morphology. This projection of the points can be in any orientation, i.e., using any direction of projection vector. The point of intersection of projection vector with target morphology is the target point position. In cases where the projected point 'misses' the target morphology (for example, the target morphology is not reached by the magnitude of the projection vector set by the user or by Eqn (11)), a function is used to place the target point. This function is a combination of a position on the projection vector and the nearest point orthogonal to the projection vector on the target morphology (see FIG. 13I).

The warping interpolation function is formed using, for example, a moving frames linear optimisation or an As Rigid As Possible method. All device coordinate points are resolved to new warped positions by the interpolation function (see FIG. 13J). The user checks results (see FIG. 13K), the model is checked for 3D print suitability, and then the model is exported as .stl for 3D printing or other suitable file for CAM.

Core Method for Unstructured (True 3D, i.e., Not Plane, Curve or Grid Structured Points) Source and Target Point Customisation of Device (e.g., Customisation of a Child Plagiocephaly Corrective Helmet from a Surface Reconstruction of the Child's Head, See FIGS. 18A-18E).

The device is aligned with centroid at global x,y,z=0,0,0 with x axis=length, y axis=width, z axis=depth of device. In this case, the device is a plagiocephaly 'helmet' that, as the base device, has the shape of a 'normal' child's head. This 'normal' head shape could be acquired from a database of child head shapes, which would be age and sex matched to that of the plagiocephalic child, and serves as the 'source' morphology. The 'target' morphology is aligned with centroid at global x,y,z=0,0,0 with x axis=length, y axis=width, z axis=depth of device. In this embodiment, the target morphology is the child's plagiocephalic head shape.

This head shape could be acquired using a number of different methods including surface scanning (structured light, photogrammetry or laser), CT or MRI scanning or by adjusting the shape of generic head shape to match measured parameters, such as lengths or circumferences (see above descriptions of this method).

Figure 18A:
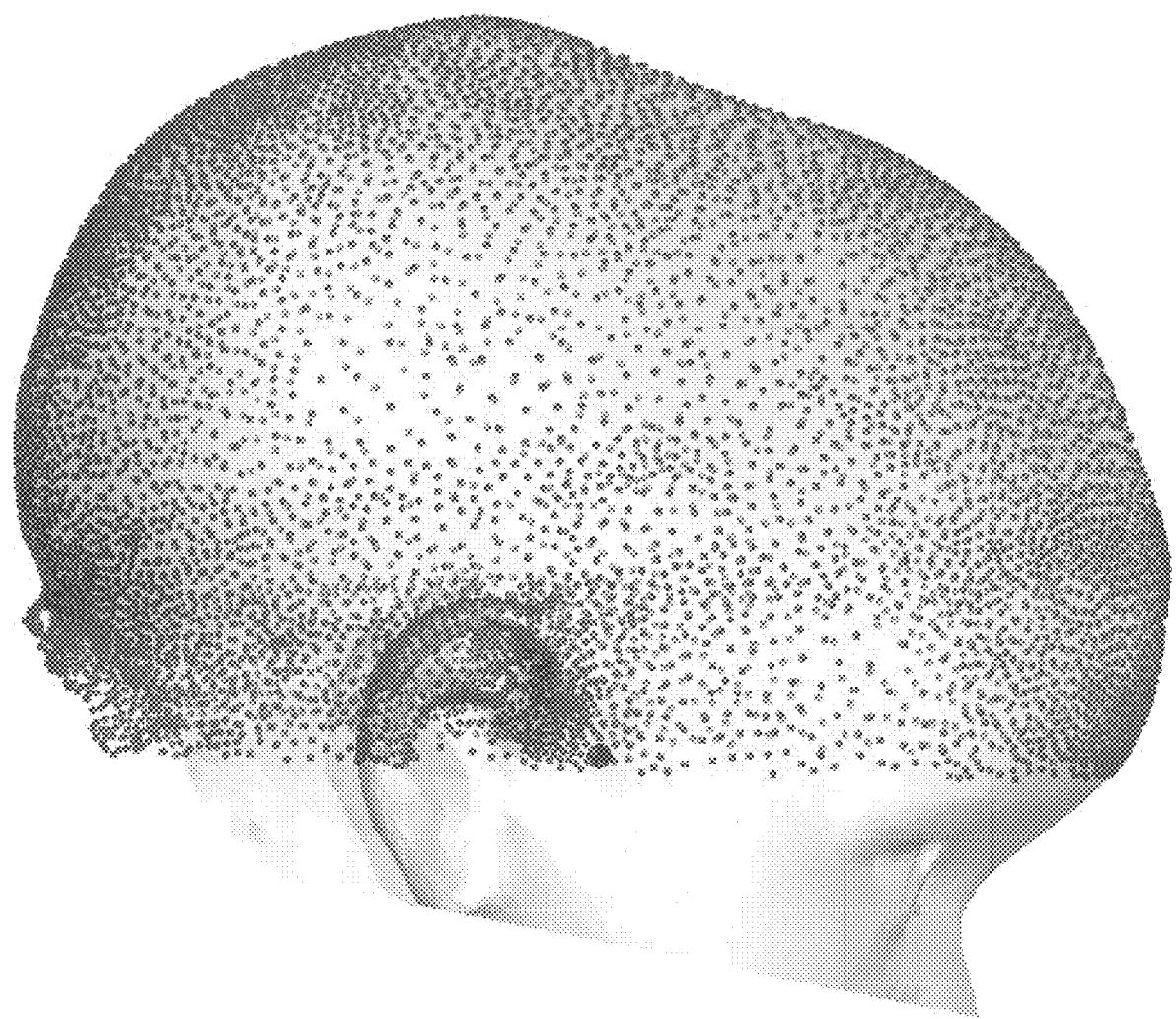
FIGS. 18A to 18E show a 3D warp of a plagiocephaly helmet, illustrating the method as applied to a shape correcting external device.

FIG. 18A shows the alignment of the plagiocephalic, or target, head shape with the global coordinate system. The black point slightly anterior to the ear shows the coordinate system x,y,z=0,0,0 (FIG. 18A). In this embodiment, only the points greater than z=0 are needed (these are shown dark grey in FIG. 18A). The target position and alignment are adjusted, if needed, so that device and target are aligned as desired/so as to achieve effective projection of device source points to target morphology.

Figure 18B:
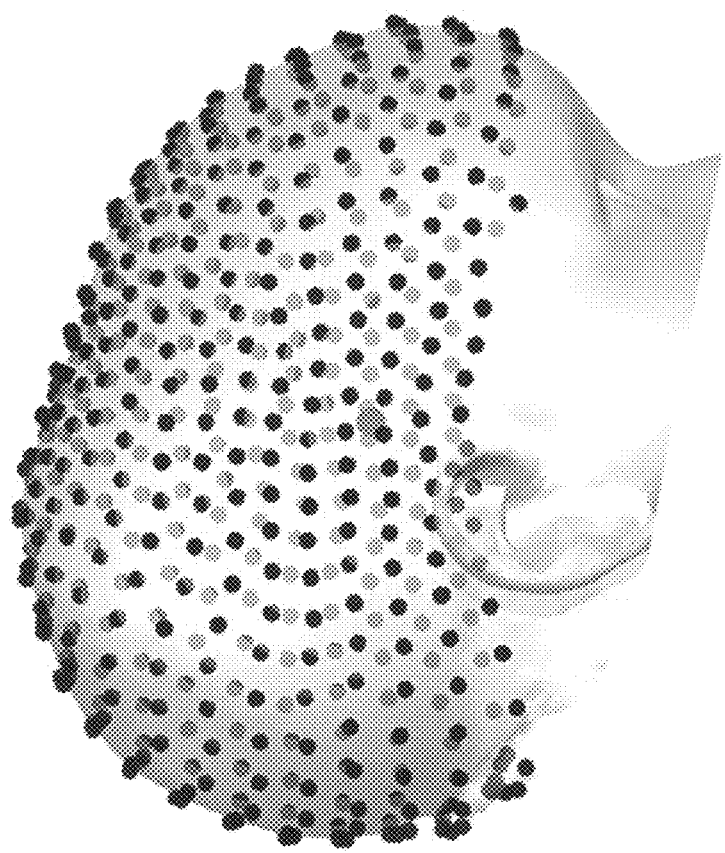
Figure 18B:
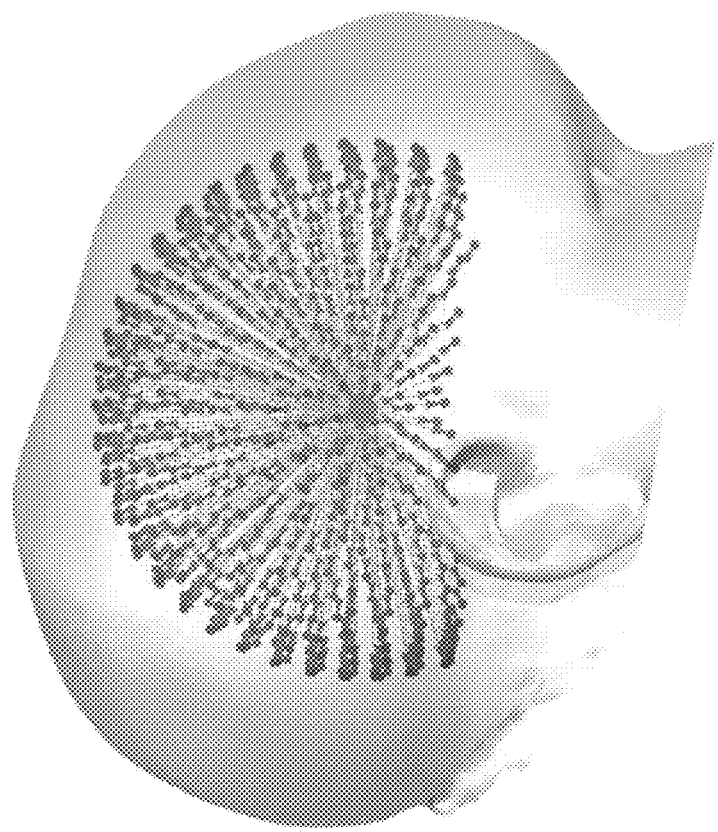
Figure 18C:
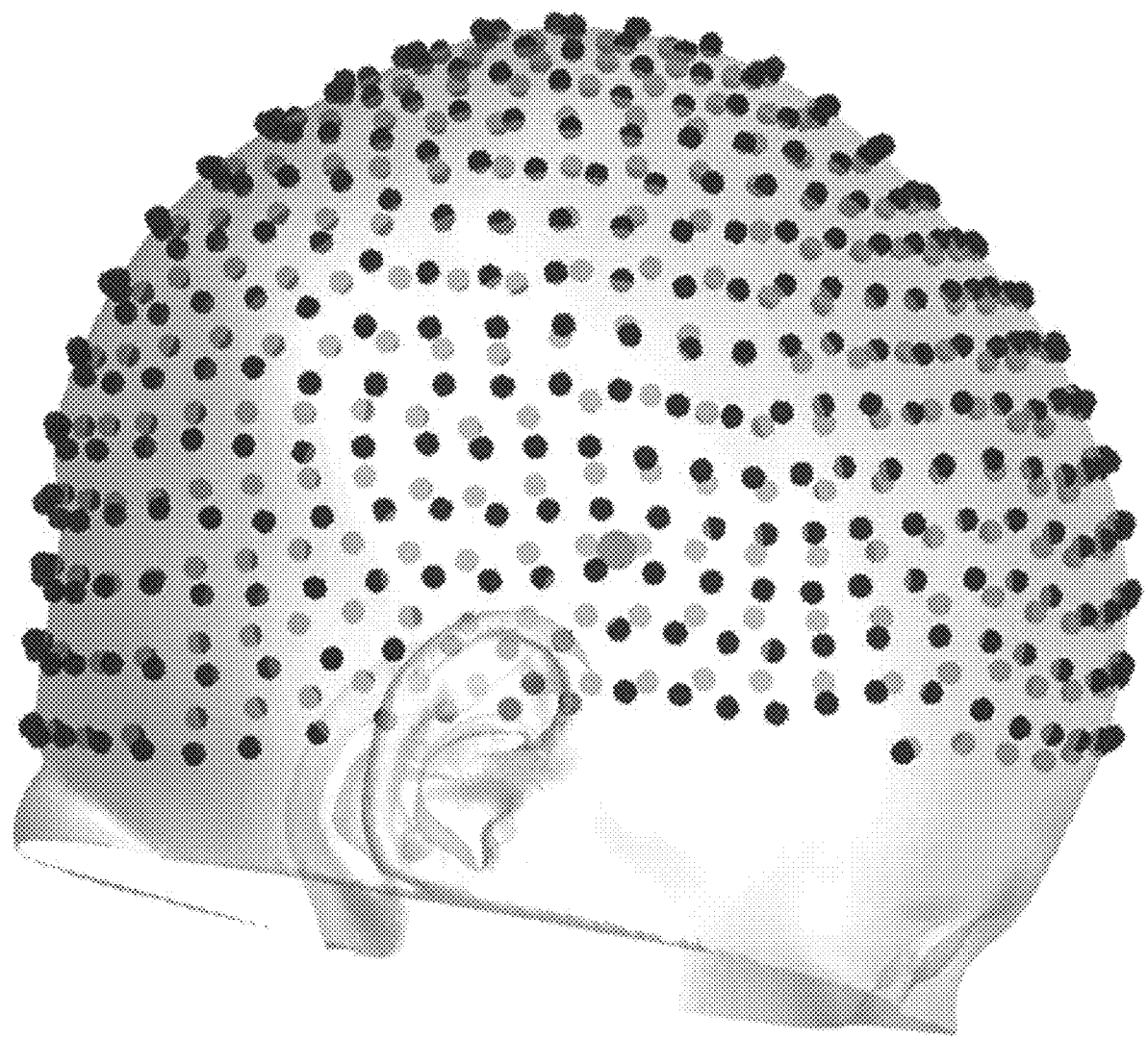

Source points are projected radially from a point inside the dark grey points shown in FIG. 18A until intersection with target morphology, as shown in FIG. 18B. FIG. 18B shows the point for radial projection as a large point slightly anterior and superior to the ear. The position of this point could be determined using a number of different methods. In the present embodiment, the centre point of a sphere fitted to the multitude of small dark grey points shown in FIG. 18A was used. The larger black points are the points of intersection of the projected points and the surface. The point of intersection of projection vector with target morphology is the target point position.

In cases where the projected point 'misses' the target morphology (for example, the target morphology is not reached by the magnitude of the projection vector set by the user or by Eqn (11)), a function is used to place the target point. This function is a combination of a position on the projection vector and the nearest point to the projection vector on the target morphology.

This process is repeated for the normal head morphology (see FIG. 18C), with these points representing the source points (as the device, in this instance has a normal head shape).

Figure 18D:
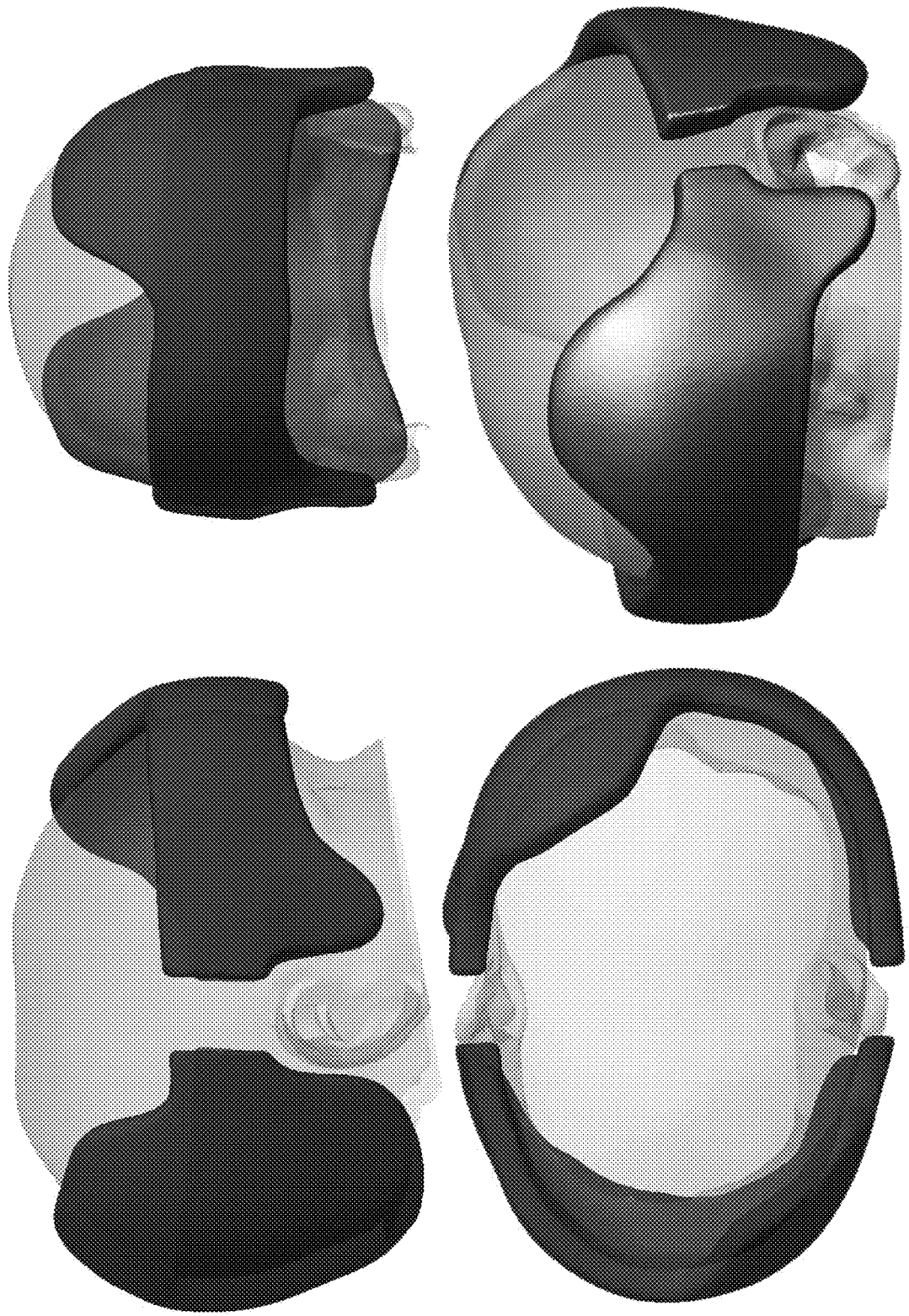

The warping interpolation function is formed using an 'As Rigid As Possible' method. All device coordinate points are resolved to new warped position by the interpolation function. The warped shape of the plagiocephaly helmet (fitted to a cranial synostotic head shape) is shown in FIG. 18D. The two halves of the helmet may be held together by adjustable straps that span the 'gaps', above the ears. These allow a certain degree of adjustment in the helmet.

The user checks results, the model is checked for 3D print suitability, and then the model is exported as .stl for 3D printing or other appropriate file format for CAM.

Figure 18E:
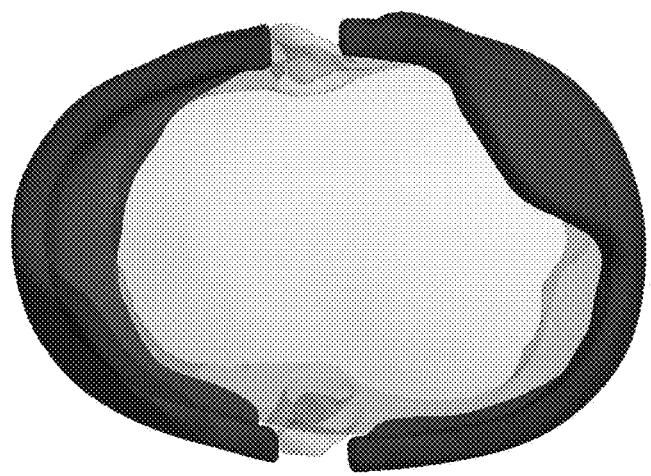
Figure 18E:
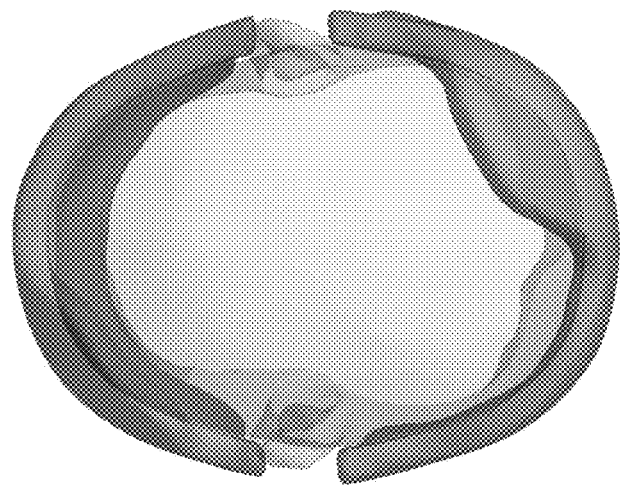
Figure 18E:
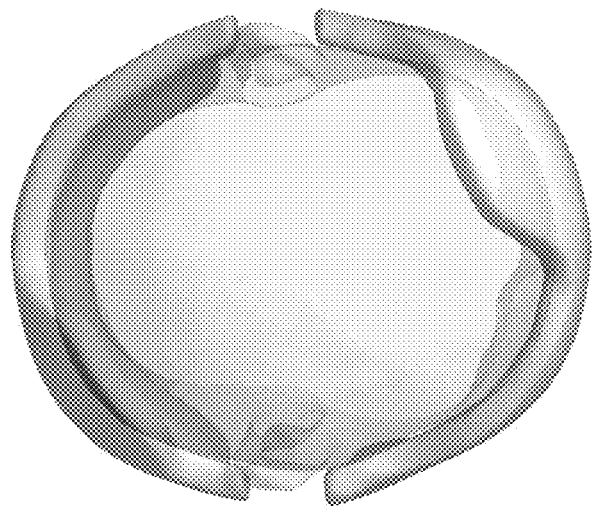

For corrective embodiments, such as the plagiocephaly corrective helmet described here, the method described here enables intermediate points between the extremes of start and normal shapes to be realised as the base/generic and warped devices maintain the same point number and connectivity. For instances where a corrective device may be used for a number of months, it may be desirable to produce a number of device shapes between the source and target shapes, to guide more effectively and comfortably, the patient's morphology. FIG. 18E shows an example of this with the top (dark grey) device representing the starting head, and helmet, shape and the bottom (light grey) device representing the normal head, and helmet, shape. The middle shape in FIG. 18E represents the head and helmet shape half way in between these two (start and end) shapes.

For a corrective device such as the helmet, shown in FIG. 18E, the first shape of helmet manufactured may, for example, be ¼ of the normal shape (i.e., ¼ of the way between the start shape and the normal shape), with a second helmet being ½ of the normal shape (as shown by the middle shape in FIG. 18E), a third helmet being ¾ of the normal shape, and the fourth helmet being the normal shape shown at the bottom of FIG. 18E. The comfort and degree of pressure applied to the cranium can be controlled by the use of variable thickness, density and stiffness foam, which can be replaced as the head alters shape.

In another embodiment, the method disclosed here can be used to calculate and cut, for example using a computer controlled cutting device, different shaped blocks of foam that can be attached to the inside of a normal shape helmet. These foam blocks would apply differing pressures to the cranium to guide the shape correction.

EXAMPLES OF APPLICATION OF THE METHOD OF THE PRESENT DISCLOSURE

The method of the present disclosure may have many applications in many different industries. In relation to the medical field, the following applications, at least, are contemplated.
  a) Fracture fixation by plate with no/minimal re-alignment of bone fragments.
    Examples: 1) metacarpal fracture and fixation with small plate, and
    2) mandibular condyle fracture.
  b) Fracture or osteotomy fixation by plate with re-alignment of bone fragments
    Example: 1) radius case shown in FIGS. 6A to 6C.

c) Fracture fixation by Inter-medullary (IM) nail with minimal/no re-alignment of bone fragments
   Examples: 1) femoral Inter Medullary (IM) nail with head and neck components, and
   2) humeral IM nail.
d) Fracture or osteotomy fixation by Inter-medullary (IM) nail with re-alignment of bone fragments
   Examples: 1) femoral Inter Medullary (IM) nail, and
   2) humeral IM nail.
e) Single joint re-surfacing
   Examples: 1) hip femoral head, and
   2) humeral head.
f) Total joint arthroplasty
   Examples: 1) hip,
   2) knee,
   3) ankle, and
   4) shoulder.
g) Inter body spacer
   Example: 1) cervical/thoracic/lumber inter vertebral body spacer.
h) External splint, support or orthotic
   Examples: 1) finger splint 1, finger splint 2,
   2) ankle brace, and
   3) foot orthotic.
i) Plate or cup with flanges
   Examples: 1) acetabular cup with flanges, and
   2) plate with flanges.
j) Prosthesis socket
k) Plagiocephaly helmet

INDUSTRIAL APPLICABILITY

The arrangements described are applicable to the computer aided design and computer aided manufacturing industries and particularly for the medical, biomedical, automotive, and aeronautical industries.

The foregoing describes only some embodiments of the present invention, and modifications and/or changes can be made thereto without departing from the scope and spirit of the invention, the embodiments being illustrative and not restrictive.

In the context of this specification, the word "comprising" and its associated grammatical constructions mean "including principally but not necessarily solely" or "having" or "including", and not "consisting only of". Variations of the word "comprising", such as "comprise" and "comprises" have correspondingly varied meanings.

As used throughout this specification, unless otherwise specified, the use of ordinal adjectives "first", "second", "third", "fourth", etc., to describe common or related objects, indicates that reference is being made to different instances of those common or related objects, and is not intended to imply that the objects so described must be provided or positioned in a given order or sequence, either temporally, spatially, in ranking, or in any other manner.

Although the invention has been described with reference to specific examples, it will be appreciated by those skilled in the art that the invention may be embodied in many other forms.

I claim:

1. A method for forming a digital model of a customised medical device from a digital model of a base device having an accompanying set of points, the method comprising the steps of:
   defining a curved plane based on predefined curve parameters, wherein the predefined curve parameters include at least a x-axis curvature and a y-axis curvature;
   projecting points from said set of points to match the curved plane in order to form a set of target points;
   defining a warping function based on the target points; and
   applying said warping function to said digital model of said customised medical device that incorporates the different x-axis and y-axis curvatures.

2. The method according to claim 1, wherein triangulated point correspondence between said base device and said customised medical device is maintained in order to retain original design features of the base device.

3. The method according to claim 2, wherein said original design features of the base device are selected from the group consisting of: drill holes, screw holes, cutting guides, edge fillets, hemi-spherical cup geometry, locking screw threads, planar slits, cylindrical drill guide holes, and thickness.

4. The method according to claim 1, wherein the x-axis or y-axis curvature is one of: (i) a radius of a curve, or (ii) a height of maximum point of curvature.

5. The method according to claim 1, wherein the x-axis or y-axis curvature is based on a target anatomical shape.

6. The method according to claim 1, wherein the base device is one of a bone fixation plate, an intermedullary nail, or a rod.

7. The method according to claim 6,
   wherein the base device is a rod and the digital model of the customised medical device is used as an input to a computer aided manufacturing device to fabricate a customised device,
   wherein the computer aided manufacturing device is one of: a bending device with numerical control over a degree of bend achieved; a robotic bending device; an additive manufacturing device; and a CNC mill.

8. The method according to claim 1,
   wherein the digital model of the customised medical device is used as an input to a computer aided manufacturing device to fabricate a customised device,
   wherein the computer aided manufacturing device is selected from the group consisting of: 3D printers, computer numerical control (CNC) mills, CNC lathes, CNC bending, CNC hole punching, CNC routing, CNC sawing, and CNC hydraulic presses.

9. The method according to claim 8, wherein the base device is a rod and the method includes the further step of:
   manually bending a rod to produce a customised device, based on the digital model of the customised device.

10. A customised bone fixation plate made according to the method of claim 1, wherein:
    said x-axis curvature is along a lateral axis of said plate to accommodate curvature of a vertebral body; and
    said y-axis curvature is along a longitudinal axis of said plate to accommodate at least one of disc and bony rim to a vertebral body endplate.

11. The plate according to claim 10, wherein said original design features of the base device are selected from the group consisting of: drill holes, screw holes, cutting guides, edge fillets, hemi-spherical cup geometry, locking screw threads, planar slits, cylindrical drill guide holes, and thickness.

12. A curved rod made according to the method of claim 1, wherein:
    said x-axis curvature is along a lateral axis of said rod to accommodate curvature of a spine of a patient; and
    said y-axis curvature is along a longitudinal axis of said rod to accommodate curvature of the spine of the patient.

13. A method comprising the steps of:
uploading a first digital model of a generic base device to a computing device;
utilising a graphical user interface associated with said computing device to:
- select a site on a second digital model of a target shape for placement of the generic base device;
- orient said first digital model of said generic base device within a co-ordinate system; and
- align the second digital model of the target shape within the co-ordinate system;

projecting a set of source points on the first digital model of the generic base device to intersect a surface of the second digital model of the target shape at a set of target points;
calculating a warping interpolation function by fitting the source points to corresponding locations of the target points; and
applying the warping interpolation function to all points of the first digital model of the generic base device to produce a third digital model of a customised device.

14. The method according to claim 13, wherein the first digital model of the generic base device has a set of design features, and
further wherein the warping interpolation function preserves those design features by rotating and translating points of the first digital model corresponding to those design features in accordance with the warping interpolation function, said warping interpolation function being constrained from applying non-rigid transformations and scaling to the points of the first digital model corresponding to those design features.

15. The method according to claim 14, wherein said design features are selected from the group consisting of: drill holes, screw holes, cutting guides, edge fillets, hemispherical cup geometry, locking screw threads, planar slits, cylindrical drill guide holes, and plate thickness.

16. The method according to claim 14, wherein the points of the first digital model of the generic base device corresponding to the design features are stored in conjunction with the first digital model of the generic base device.

17. The method according to claim 14, wherein the points of the first digital model of the generic base device corresponding to the design features are selected by a user through interaction with the user interface.

18. The method according to claim 13, wherein the warping interpolation function is utilised to smooth anatomical geometry to create a smooth geometry in the customised device.

19. The method according to claim 18, wherein the warping interpolation function utilises a rigid warping function.

* * * * *